(12) United States Patent
Yang

(10) Patent No.: US 7,320,864 B2
(45) Date of Patent: Jan. 22, 2008

(54) METHODS OF USING MOLECULAR CONSTRUCTS FOR DETECTION OF BIOCHEMICAL REACTIONS

(75) Inventor: Jiacheng Yang, Hillsboro, NJ (US)

(73) Assignee: BioArray Solutions Ltd., Warren, NJ (US)

( * ) Notice: Subject to any disclaimer, the term of this patent is extended or adjusted under 35 U.S.C. 154(b) by 44 days.

(21) Appl. No.: 11/411,584

(22) Filed: Apr. 26, 2006

(65) Prior Publication Data

US 2006/0234284 A1 Oct. 19, 2006

(51) Int. Cl.
*C12Q 1/68* (2006.01)
*C12Q 1/00* (2006.01)
*C07H 21/02* (2006.01)
*C07H 21/04* (2006.01)

(52) U.S. Cl. ............... 435/6; 435/4; 536/23.1; 536/24.3

(58) Field of Classification Search ............ 435/4, 435/6; 536/23.1, 24.3
See application file for complete search history.

(56) References Cited

U.S. PATENT DOCUMENTS 6,316,186 B1   11/2001   Ekins

FOREIGN PATENT DOCUMENTS

| EP | 1394270 | 3/2004 |
|----|---------|--------|
| WO | WO 96/02558 | 2/1996 |
| WO | WO 96/30392 | 10/1996 |
| WO | WO 96/41011 | 12/1996 |
| WO | WO 98/20153 | 5/1998 |
| WO | WO 98/53093 | 11/1998 |
| WO | WO 99/41273 | 8/1999 |
| WO | WO 99/51773 | 10/1999 |
| WO | WO 02/14864 | 2/2002 |
| WO | WO 03/058196 | 7/2003 |

OTHER PUBLICATIONS

Koch et al., "PNA-Peptide Chimerae," Tetrahedron Letters 36 : 6933-6936 (1995).*
Niemeyer et al., Oligonucleotide-directed self-assembly of proteins: semisynthetic DNA—streptavidin hybrid molecules as connectors for the generation of macroscopic arrays and the construction of supramolecular bioconjugates, Nucleic Acids Research, vol. 22: 5530-5539 (1994).
Niemeyer et al., DNA-Directed Immobilization: Efficient, Reversible, and Site-Selective Surface Binding of Proteins by means of Covalent Can Stretavidin conjugates, Analytical Biochemistry 268, 54-63 (1999).
European Search Report, Dec. 16, 2003.
Partial European Search Report, Mar. 19, 2004.

* cited by examiner

*Primary Examiner*—Ethan Whisenant
(74) *Attorney, Agent, or Firm*—Eric P. Mirabel

(57) ABSTRACT

The present invention relates to molecular constructs and methods of their use in detecting biochemical reactions. In particular, the invention relates to a molecular construct having a capture portion and a substrate portion, where the capture portion isolates the construct from a sample medium, and the substrate portion enables the construct to be acted upon and undergo a physical change which can be detected and measured. These molecular constructs may be used in diagnostic assays, genetic screening for potential risks of certain diseases in individuals, and drug discovery and toxicogenomics, using high throughput screening of compounds.

7 Claims, 41 Drawing Sheets

SEQUENCE LISTING

```
<160> NUMBER OF SEQ ID NOS: 10

<210> SEQ ID NO 1
<211> LENGTH: 16
<212> TYPE: PRT
<213> ORGANISM: Homo sapiens
<300> PUBLICATION INFORMATION:
<301> AUTHORS: Cheng, et al.
<302> TITLE: A synthetic peptide derived from p34cdc2 is a specific and
      efficient substrate of src-family tyrosine kinases
<303> JOURNAL: J. Biol. Chem.
<304> VOLUME: 267
<305> ISSUE: 13
<306> PAGES: 9248-9256
<307> DATE: 1992-05-05
<309> DATABASE ENTRY DATE:
<313> RELEVANT RESIDUES: (2)..(16)

<400> SEQUENCE: 1

Cys Lys Val Glu Lys Ile Gly Glu Gly Thr Tyr Gly Val Val Tyr Lys
1               5                   10                  15

<210> SEQ ID NO 2
<211> LENGTH: 18
<212> TYPE: PRT
<213> ORGANISM: Homo sapiens
<220> FEATURE:
<221> NAME/KEY: PEPTIDE
<222> LOCATION: (12)..(12)
<223> OTHER INFORMATION: Tyr (Y) is phosphorylated
<300> PUBLICATION INFORMATION:
<301> AUTHORS: Baldwin, et al.
<302> TITLE: Phosphorylation of gastrin-17 by epidermal growth
      factor-stimulated tyrosine kinase.
<303> JOURNAL: Nature
<304> VOLUME: 301
```

```
<305> ISSUE: 5899
<306> PAGES: 435-437
<307> DATE: 1983-02-03
<309> DATABASE ENTRY DATE:
<313> RELEVANT RESIDUES: (2)..(18)

<400> SEQUENCE: 2

Cys Glu Gly Pro Trp Glu Glu Glu Glu Ala Tyr Gly Trp Met Asp
1               5                   10                  15

Phe Lys

<210> SEQ ID NO 3
<211> LENGTH: 15
<212> TYPE: PRT
<213> ORGANISM: Rous sarcoma virus
<300> PUBLICATION INFORMATION:
<301> AUTHORS: Casnellie, et al.
<302> TITLE: Phosphorylation of synthetic peptides by a tyrosine protein
      kinase from the particulate fraction of a lymphoma cell line
<303> JOURNAL: Proc. Natl. Acad. Sci. USA
<304> VOLUME: 79
<305> ISSUE: 2
<306> PAGES: 282-286
<307> DATE: 1982-01
<309> DATABASE ENTRY DATE:
<313> RELEVANT RESIDUES: (2)..(15)

<400> SEQUENCE: 3

Cys Arg Arg Leu Ile Glu Asp Ala Glu Tyr Ala Ala Arg Gly Lys
1               5                   10                  15

<210> SEQ ID NO 4
<211> LENGTH: 15
<212> TYPE: PRT
<213> ORGANISM: Homo sapiens

<400> SEQUENCE: 4

Lys Val Glu Lys Ile Gly Glu Gly Thr Tyr Gly Val Val Tyr Lys
1               5                   10                  15

<210> SEQ ID NO 5
<211> LENGTH: 30
<212> TYPE: PRT
<213> ORGANISM: Artificial Sequence
<220> FEATURE:
<223> OTHER INFORMATION: PNA-Caspase 3 dual-labeled peptide chimera

<400> SEQUENCE: 5

His His His His His His Asp Glu Val Asp Ala Lys Cys Cys Cys
1               5                   10                  15
Cys Cys Cys Cys Cys Cys Cys Cys Cys Cys Cys Cys Cys
            20                  25                  30

<210> SEQ ID NO 6
<211> LENGTH: 10
<212> TYPE: PRT
<213> ORGANISM: Artificial Sequence
<220> FEATURE:
<223> OTHER INFORMATION: Green A color-encoded bead

<400> SEQUENCE: 6

Ala Ala Ala Ala Ala Ala Ala Ala Ala Ala
1               5                   10

<210> SEQ ID NO 7
<211> LENGTH: 10
<212> TYPE: PRT
<213> ORGANISM: Artificial Sequence
```

```
-continued

<220> FEATURE:
<223> OTHER INFORMATION: Green B color-encoded bead

<400> SEQUENCE: 7

Ala Ala Gly Gly Ala Gly Ala Gly Ala Ala
1               5                   10

<210> SEQ ID NO 8
<211> LENGTH: 4
<212> TYPE: PRT
<213> ORGANISM: Artificial Sequence
<220> FEATURE:
<223> OTHER INFORMATION: Functional moiety of PNA chimera I

<400> SEQUENCE: 8

Asp Glu Val Asp
1

<210> SEQ ID NO 9
<211> LENGTH: 4
<212> TYPE: PRT
<213> ORGANISM: Artificial Sequence
<220> FEATURE:
<223> OTHER INFORMATION: Functional moiety of PNA chimera II

<400> SEQUENCE: 9

Val Glu Ile Asp
1

<210> SEQ ID NO 10
<211> LENGTH: 4
<212> TYPE: PRT
<213> ORGANISM: Artificial Sequence
<220> FEATURE:
<223> OTHER INFORMATION: Functional moiety of PNA chimera III

<400> SEQUENCE: 10

Ile Glu Thr Asp
1
```

METHODS OF USING MOLECULAR CONSTRUCTS FOR DETECTION OF BIOCHEMICAL REACTIONS

FIELD OF THE INVENTION

The invention generally relates to molecular biology and biochemistry. The invention provides molecular constructs and methods of use in detecting biochemical reactions, either individually or as a plurality.

BACKGROUND OF THE INVENTION

Biochemical reactions within cells define cellular function and activity. These reactions include a complex interplay between receptor ligand interactions and enzymatic reactions, which orchestrate the signaling and activities of a cell. Physiological conditions influence the activity levels of enzymes and proteins mediating these reactions.

For example, modifications of amino acid residues on peptide chains play an important role in the regulation of protein function in cells. Transfer of phosphate groups, methyl groups or carbohydrates induces conformational changes in protein substrates, which in turn results in changes in protein function. These reactions are usually reversible. Protein modification involves particular classes of enzymatic activities. For example, methylation is generally catalyzed by a family of enzymes, known as methyltransferases. Protein methylation regulates membrane attachment of cytosolic proteins and contributes to prevention of C-terminal proteolytic degradation of peptides. For example, most G proteins are methylated. The methylated cysteine residue is located at or near the carboxyl terminus of G proteins may facilitate attachment of the peptides to the membrane for signal transduction (Rando, *Biochim Biophys Acta* 1300(1):5-12 (1996), Hrycyna, *Pharmacol. Ther.* 59(3):281-300 (1993)). Histidine at position 73 on several kinds of actin is also methylated. It has been shown that methylation is required for maintaining proper conformation of actin molecules (Yao, *J. Biol. Chem.* 274(52):37443-9 (1999)). Methylation of lysine residue in the S-1 region of myosin results in decreased ATP binding in myofibrine contraction (Bivin, *Proc. Nat'l Acad. Sci USA* 91(18):8665-9 (1994)). It has also been shown that methylation of membrane proteins may contribute to the development of cardiovascular disease in diabetic patients (Schaffer, *Mol. Cell Biochem* 107(1):1-20 (1991)). In addition, methylation reduces protein-RNA interaction in nuclear proteins (Kim, *Amino Acids* 15(4):291-306 (1998)), and selectively modulates SH3 domain-mediated protein-protein interactions (Bedford, *J. Biol. Chem,* 275(21):16030-6 (2000)).

Similarly, carbohydrates can be transferred to side chains of specific asparagine, serine, or threonine residues in many secreted proteins or proteins displayed on cell-surfaces. The transfer of a carbohydrate to asparagine at position 2181 on human coagulation factor V results in impaired interaction between factor V and phospholipid membranes (Nicolaes, *Biochemistry* 38(41):13584-91 (1999)). Large carbohydrates, known as polysaccharides, are formed by linking many sugar monomers.

SUMMARY OF THE INVENTION

The present invention relates to molecular constructs having a capture portion and a substrate portion. The capture portion serves to isolate the construct from the sample being tested, while the substrate portion provides a reactive site for determining the presence or activity level of a target molecule of interest. In a preferred embodiment, the molecular construct comprises a peptide-nucleic acid (PNA) as a capture portion and a peptide or protein as a substrate portion. Alternative preferred substrate portions comprise non-peptide molecules, such as for example, fatty acids, steroids, sugars, co-factors and other entities which act on or are substrates for target molecules of interest.

The present invention also relates to methods of using the molecular constructs. Methods for detecting one or multiple enzyme activities are provided by measuring the modified substrate portions of the molecular construct, which in turn is indicative of one or more enzyme activities in a sample. Similarly, methods for detecting analytes in a cell, a cell population or in a tissue sample are also provided.

Molecular constructs of the present invention having a peptide-nucleic acid (PNA) capture portion are particularly beneficial over those in the prior art. Hybridization of PNA to complementary nucleic acid sequences are more specific and occur with higher affinity because of the uncharged nature of the PNA backbone. PNA-nucleic acid sequence hybridization is much better because of various PNA characteristics that nucleic acids, such as DNA or RNA, do not possess. PNA is stable over a wide range of pH and low ionic strength conditions. These properties make PNAs especially suitable for use in the detection assays of the present invention.

There is a need for an assay for detection and analysis of biochemical reactions that is accurate, both time and cost efficient, and capable of screening one or a plurality of reactions with great sensitivity. Therefore, it may be useful to have a method to detect one or more biochemical reactions that is easy to use, highly specific, accurate, and sensitive for screening biochemical reactions in order to prevent and/or treat diseases, preferably human diseases that may be induced virally, bacterially, and parasitically.

DETAILED DESCRIPTION OF THE INVENTION

Figure 1:
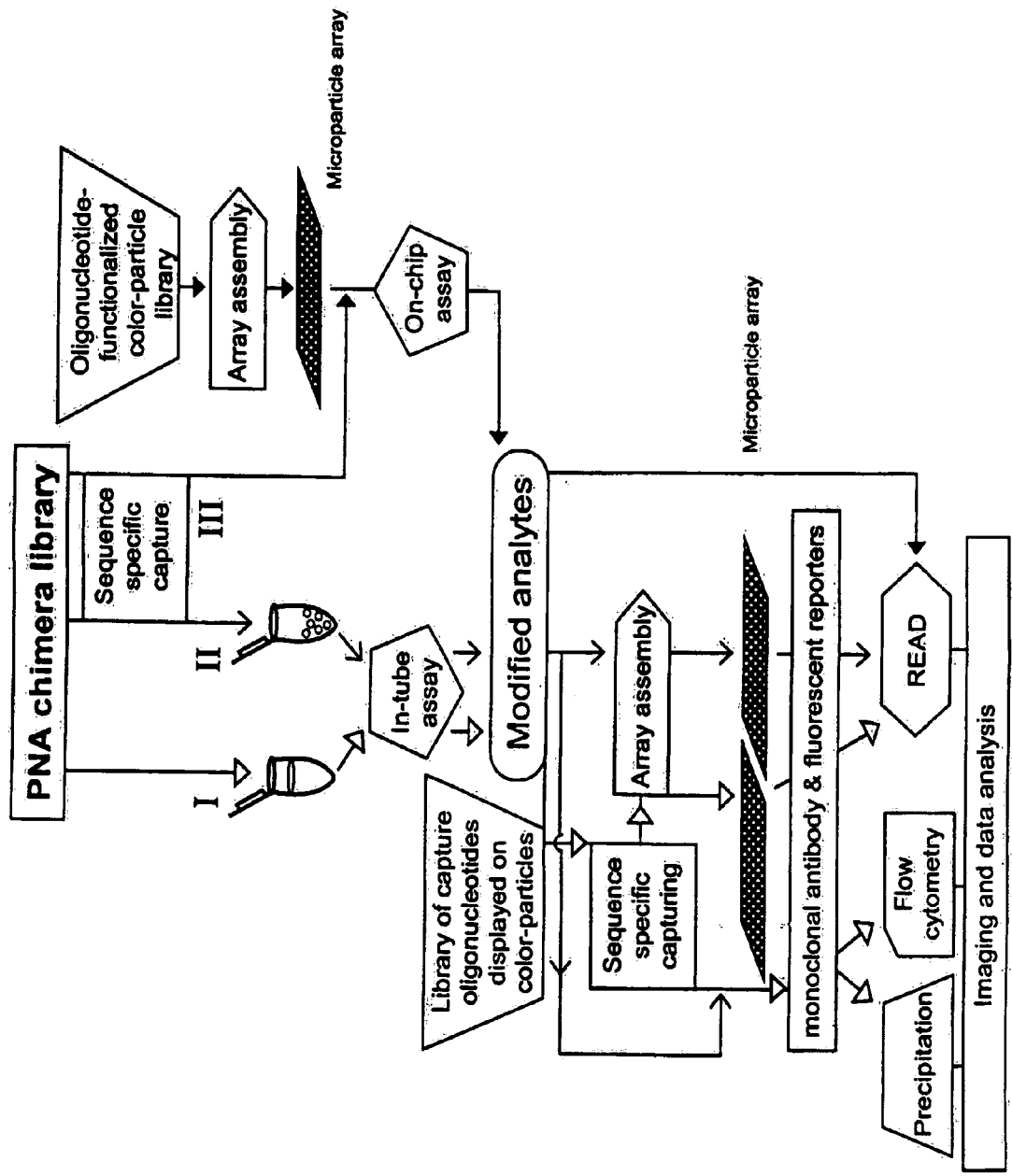
FIG. 1 shows an example of detecting microparticles using methods by LEAPS or direct deposition, followed by detection on the arrays using READ, flow cytometry, and precipitation methods.

The invention relates to a molecular construct comprising a capture portion and a substrate portion. The capture portion allows the construct to be isolated from a mixture of molecules, and preferably comprises a nucleic acid or nucleic acid derivative. The substrate portion allows the construct to be acted upon and undergo a change, which can be measured or detected. The change may be a physical one such as a chemical modification or a cleavage or addition to the substrate portion. Alternatively the change may be the binding of a ligand or cell to the substrate portion of the construct.

The molecular constructs of the invention may be PNA-peptide chimerae comprising covalently-linked components, including a PNA oligomer, and one or more derivative forms of PNA (such as for example pPNA), a linker, and a synthetic peptide or other substrate portion. The PNA portion of the chimera (which can be linear or in bis-format) serves as an anchor for capturing the complex to a complementary oligonucleotide, which is immobilized on a solid support. The base-sequence of the PNA anchoring domain provides a unique tag to the analyte of the substrate domain of the chimera. The solid support may have defined physical characteristics. In addition, the solid support may be optically or chemically encoded.

The substrate portion of the chimera serves as a functional/substrate component participating in biochemical assays. The substrate portion of the molecular construct comprises a molecular structure, which acts as a ligand or enzyme substrate in a biochemical reaction. For example, proteins or peptides may be used as a substrate for enzymatic reactions or provide ligand-binding sites. Peptides may also be useful in detecting ligand-receptor reactions. Proteins may be used as substrates to isolate cell-populations having specific cell-surface markers. Alternatively, enzyme cofactors may form all or part of the substrate portion of the chimera, such as, for example, ATP, cAMP, GTP or the like. Similarly, fats, steroids and/or fatty acids may form the substrate portion of the chimera, in that these molecules also may be modified during biochemical reactions and thus may be measured using the present invention. Carbohydrates may also form all or part of the substrate portion of the chimera. These molecules include, for example, simple sugars, starches, polysaccharides, proteoglycans, and the like.

The substrate portion may be modified to contain one or more moieties, such as detectable labels or enzyme cleavage recognition moieties, such as phosphate groups, sugar groups, methyl groups, or the like. In one embodiment, the substrate portion of the chimera contains one or more fluorescent tags. These tags may be combined with the use of polyhistidine, biotin, digoxygenin tags or the like. By using a single-labeled substrate portion, enzyme digestion eliminates the tag from the digested substrates. By using a double-labeled substrate portion, enzyme digestion eliminates the quenching dye from the substrates resulting in emission of fluorescence from the second dye remaining on the cleaved product. By using a substrate portion with one detectable tag plus an internal polyhistidine tag, enzyme digestion eliminates the fluorescent dye. In addition, detectable signal from the uncut substrates can be normalized to detect signal generated from the internal polyhistidine tag. These embodiments are illustrated in detail in Examples 10, 14, 16, and 17, which demonstrate that such molecular constructs can provide quantitative information regarding enzyme activities of interest. In another embodiment, the substrate portion of the chimera contains one or more phosphate groups or other moieties of interest, which may act as part of the enzyme cleavage site for a phosphatase or other enzymes of interest.

The constructs of the invention can be used in methods for detecting changes in the substrate portion. Methods disclosed herein can be used to determine protein-protein interactions, ligand-receptor binding, protein modification, protein expression, and enzymatic activity in cell-free and cell-based formats. The method of the invention can also be used to isolate cells bearing specific cell surface markers. These methods may be used for a variety of purposes. The constructs may be used in genetic screening analyses, in diagnoses, treatment and/or prevention of disease, in drug discovery and in toxicogenomics assays for diseases or conditions, such as but not limited to those related to cancer, parasite infections, neuronal disorders, hematopoietic disorders, muscoskeletal disorders, cardiovascular disorders, lymphatic disorders, respiratory disorders, endocrine disorders, and gastrointestinal disorders.

Generally, the methods of use for the molecular constructs of the invention react the PNA-substrate chimera with proteins, ligands, or enzymes in a test sample. This reaction may be carried out in homogeneous solution or the capture portion of the chimera may be pre-immobilized on a solid matrix prior to the reaction. This reaction modifies the substrate portion of the chimera, if the test reaction takes place on the surface of the sample. If the biochemical reaction was carried out in solution, the chimera is then captured to an oligonucleotide-functionalized solid support in a sequence-specific manner. In one embodiment, color-encoded microparticles are used as the solid support. Microparticles may be assembled using methods known in the art, such as LEAPS or direct deposition. LEAPS is a technology known as Light-controlled Electrokinetic Assembly of Particles near Surfaces and is a process for on-demand fabrication of particle arrays for multianalyte molecular analysis. LEAPS is described in detail in U.S. Pat. No. 6,251,691 and WO 97/40385, which are incorporated herein, in toto, by reference. After the biochemical reactions are performed, the chimerae are captured to complementary DNA oligonucleotide sensors on the solid surface. The identity of the chimerae is then determined according to the code of the carrier's surface (such as the color code of the beads) in subsequent detection and data analysis. Following capture, the chimerae on the surface may be detected directly according to methods known in the art. Non-limiting examples of such methods include precipitation reactions, peroxidase or fluorescent dyes, labeled antibody, ligand-binding detection, or flow cytometry. Modified substrate portions of the molecular constructs may be detected by one of several possible formats known in the art, such as, for example, Random Encoded Array Detection (READ) (WO 97/40385) of assembled particles, flow cytometric detection of particle suspension, precipitation on spatially defined solid surfaces, or the like.

DNA oligonucleotides displayed on a solid surface serve as sensors for sequence specific capture of the anchoring domain (i.e. capture portion) of the PNA chimerae in multiplexed assays. The oligonucleotides with defined base sequences may contain other modifications, such as spacer sequences, chemical groups, ligand(s) and/or labels, to facilitate coupling, hybridization and/or detection. The solid surface may also contain defined chemical groups for coupling. Coupling of oligonucleotides to the solid surface may be a direct or indirect coupling. Specific methods for coupling are known in the art. In preferred embodiments, oligonucleotide coupling may be achieved via biotin-NeutrAvidin mediated indirect coupling, or amine-tosyl mediated direct coupling.

In one embodiment of the invention, the capture portion of the molecular construct comprises a peptide-nucleic acid (PNA). PNAs are analogs of DNA with a peptide-like backbone. The PNA backbone consists of repeating N-(2-aminoethyl) glycine residues linked by amide bonds. Unlike DNA and RNA, PNA does not contain any pentose and phosphate groups. The uncharged nature of the PNA backbone allows hybridization of PNA to complementary DNA or RNA sequence with much higher affinity and specificity than do other nucleic acids materials. In addition, PNA and bis-PNA can also hybridize to DNA in a sequence specific fashion to form a local DNA/DNA/PNA triplex. Characteristics of PNAs, and processes for synthesis of the molecules have been previously disclosed in, for example, WO 92/20702, to Buchardt et al., on Nov. 29, 1992, which is incorporated herein in toto, by reference. Since PNA hybridization is very specific, PNA probes may be shorter than DNA probes in hybridization assays. PNA is stable over a wide range of pH and conditions of lower ionic strength may be used. In addition, PNA is a synthetic compound that does not exist naturally. Therefore, both proteases and nucleases cannot recognize the polyamide backbone of PNA molecules. This property makes PNAs especially suitable for use in hybridization assays using cell lysates or cells or tissues.

PNAs of the PNA-substrate chimera are preferably 10-25 bases in length, more preferably about 15 bases. The first one or two bases at the N-terminus of the molecule are spacers conjugated with other molecules. The rest of the PNA oligomer serves as a probe mediating the sequence-specific capture of the chimera to the oligonucleotide immobilized on a solid support. The PNA portion of the chimera may be single-stranded or may be a bis-PNA. Bis-PNA, also referred to as a "PNA clamp" contain two stretches of PNA oligomers joined together through a flexible "hairpin" linker. Upon hybridization, the bis-PNA forms a triplex structure with complementary DNA.

Figure 2:
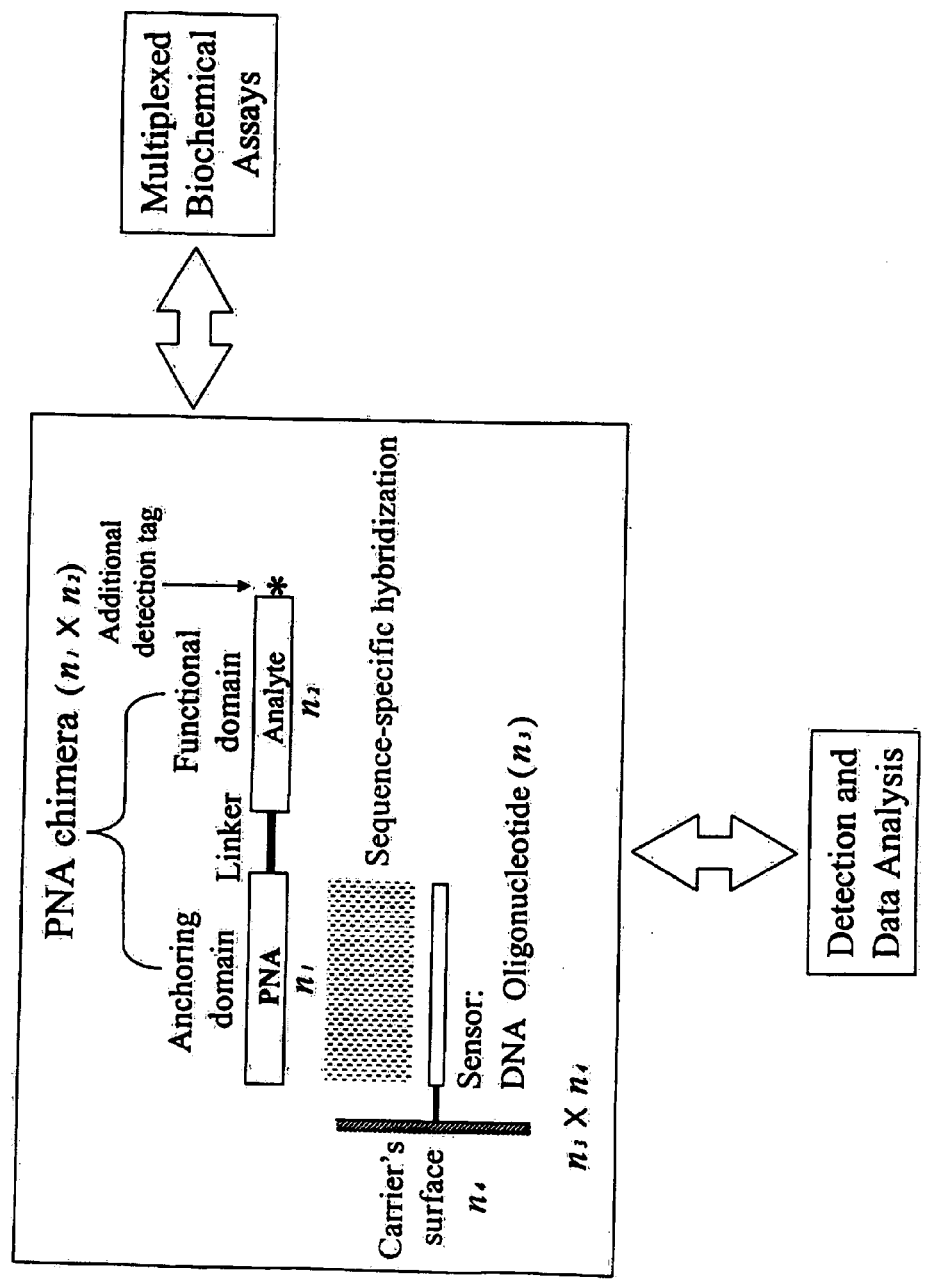
FIG. 2 shows a schematic illustration of PNA-analyte chimerae used in multiplexed assays immobilized to a carrier's surface.

PNAs have a much higher sequence-specific binding affinity and specificity to their complementary DNAs than DNA-DNA and DNA-RNA hybridization. When used in multiplexed assays, the anchoring domains of PNA chimerae hybridize to their complementary DNA oligonucleotide sensors that have been immobilized on the defined surface of the carrier of interest (FIG. 2). The DNA oligonucleotide sensors preferably contain a defined base sequence that is complementary to one of the PNA anchors (i.e. capture portions) of the PNA chimera library. Immobilization of the oligonucleotide to the carrier's surface may be accomplished according to methods known in the art, which may be either directly linked to the surface by means of a chemical reaction, such as a reaction between the amine group and a tosyl group, or indirectly coupled to the surface via linker molecules, such as binding of biotinylated oligonucleotides to avidin, streptavidin, or NeutrAvidin on the surface. The DNA oligonucleotide sensor may contain spacer molecules, labels, tags or other reactive groups to facilitate immobilization, hybridization, or detection. The carriers preferably contain defined spatial and color characteristics for decoding of the immobilized oligonucleotides. In a preferred embodiment, the carrier may comprise a microparticle. When there are $n_3$ types of DNA oligonucleotide sensors and $n_4$ types of color-encoded beads, a library of ($n_3 \times n_4$) oligonucleotide-functionalized carriers may be synthesized. Each type of oligonucleotide-functionalized microparticle preferably captures only one type of PNA chimera in the multiplexed assays.

In one embodiment of the invention, the molecular construct comprises a PNA-substrate chimera. This embodiment comprises a PNA conjugated to a polypeptide via a linker molecule. PNA oligomers can be synthesized by methods known in the art. Examples of such method include Boc chemistry, and Fmoc chemistry (Nielsen, P. E., Egholm, M, *Peptide Nucleic Acids: Protocols and Applications*, pp. 21-50, Horizon Scientific Press, 1999), which is incorporated herein in toto by reference.

In another embodiment of the invention, the substrate portion of the chimera is preferably a peptide, such as a substrate for an enzyme. One preferred class of enzymes particularly suitable for the multiplexed form of the present invention are enzymes which are part of a family of related enzymes, such as kinases, caspases, phosphatases, transferases, proteases, nucleases, and the like. For the non-multiplexed form of the present invention, any biochemical reaction which utilizes a substrate can be measured, wherein the substrate or active site can be conjugated to capture portion of the chimera. For polypeptide substrates, amino acid sequences for substrate peptides are generally available in the prior art.

In the present invention, one preferred method of conjugation incorporates a cysteine at the terminus of the peptide, e.g. the N-terminus of the peptide during its synthesis. The sulfhydryl group on the side chain of the cysteine residue may be used in conjugation of the peptide to a linker molecule during synthesis of the chimera. In addition, a lysine may be added to another terminus of the peptide for biotinylation used for detection in certain multiplexed biochemical assays. A heterobifunctional cross-linker may be used in the synthesis of a PNA-peptide chimera. Succinimidyl-4-(N-maleimidomethyl)cyclohexane-1-(carboxy-6-aminocaproate), also known as LC-SMCC, is one of the heterobifunctional cross-linkers that reacts with the sulfhydryl group and amine-group of analytes of interest. As is known in the art, the NHS ester of the LC-SMCC first reacts with the amine group on the N-terminus of PNA oligomer, at pH 7-8, resulting in activation of the PNA molecule. The maleimide group of the LC-SMCC then reacts with the sulfhydryl group of the peptide, pH 6.5-7.5, forming a functionalized PNA-peptide chimera. The synthesized PNA-peptide chimerae are purified and concentrated using various methods known in the art. Accordingly, a library of PNA-substrate chimerae may be synthesized for multiplexed biochemical assays. In a PNA-substrate chimera library, each peptide may be conjugated to a unique PNA oligomer. However, a given set of PNA oligomers may be used in the construction of several sub-libraries of PNA-substrate chimerae.

Although it is not necessary, a preferred embodiment of the present invention uses a linker in the conjugation of PNA and substrate. The cross-linker appears to provide a more flexible structure, in that it serves as a steric hinge for the PNA and the substrate portion of the chimera. The additional flexibility provided by the linker may facilitate enzyme substrate interactions as well as PNA-oligonucleotide hybridization. In addition, nanoparticles may be used as linkers in the synthesis of PNA chimerae. PNA and peptide substrates may be sequentially or simultaneously conjugated to the surface of the particles. When magnetic nanoparticles are used as linkers, the resulting PNA-substrate chimerae may be purified or enriched on demand in assays.

Detection of the modified PNA-substrate chimera may be accomplished in a variety of ways. If a single type of PNA-substrate chimera is employed, any means of detection known in the art is appropriate. If a multiplexed assay is used, then a plurality of populations of chimerae is used. In this assay, the capture portion of a given chimera population preferably corresponds to a single type of substrate portion so that after the biochemical reaction is completed, the specific modified chimera can be sorted and identified based upon its corresponding sequence, i.e., known anchor sequence. The capture of these populations of chimerae is accomplished by way of hybridization of the chimerae to a plurality of surfaces, each containing thereon an oligonucleotide which is complementary to a given capture portion of a PNA-substrate chimera. The plurality of surfaces may comprise multiple different solid matrixes, or may be a single solid surface wherein sections of the surface contain specific individual types of oligonucleotides. Multiple different solid matrices may be in the form of particles, such as magnetic particles, microparticles, nanoparticles, organic or inorganic polymers, metal or ceramic membranes, and the like. These may be modified in some way to distinguish between populations, such as by color, ionic charge, shape or reflective index, or their chemical or physical characteristics. The particles may also be physically separated to distinguish between populations. If a single solid matrix is preferred, examples include arrays or microarrays, wherein the different populations of chimerae are hybridized to discrete sections of the array.

In one embodiment of the invention, oligonucleotides are immobilized onto color-encoded microparticles. These oligonucleotides serve as probes to hybridize the target complementary capture portions of the PNA-substrate chimerae from solution, for detection. Based on sequence-specific hybridization, the color codes of the microparticles can be used to decode signal from a specific peptide in multiplexed biochemical assays. The oligonucleotide probes preferably contain 15 to 50 nucleotides. A functional group, such as, an amine group may optionally be incorporated at the end of the oligonucleotide for immobilization. Alternatively, the terminal nucleotide of the probes may be biotinylated or labeled appropriately. Procedures for synthesis of these modified oligonucleotides are known in the art. In certain situations, it may be desirable that the oligonucleotide probes have unique base sequences.

The surface of the color-encoded microparticles may carry defined chemical groups for immobilization of biomolecules used in multiplexed biochemical assays. The chemical groups may include, for example, epoxy, tosyl, amine, carboxyl, chloromethyl, aldehyde groups or other chemical groups. Specific chemical processes for generating activated chemical groups on the surface of particles is known in the arts; e.g. *Polymer Colloids: A Comprehensive Introduction*, edited by Fitch, R. M., Academic Press (1997). Oligonucleotides, DNA fragments, RNA molecules, synthetic peptides, recombinant proteins, purified native proteins or the like may be immobilized to the particles via interaction with the surface chemical groups according to methods known in the art; e.g. *Bioconjugate Techniques*, edited Hermanson, G. T., Academic Press (1995). Individual types of color-encoded microparticles may be conjugated with defined types of biomolecules, so that detectable signals from multiplexed biochemical assays can be decoded from the color of the conjugated microparticles. Functionalization of particles with biomolecules may be carried out in parallel by using an automatic device to minimize batch-to-batch variation. In addition, oligonucleotide probes may be spotted onto the surface of solid matrices. For example, spotted oligonucleotide arrays may be used to capture PNA chimerae. Furthermore, oligonucleotide probes may be directly synthesized on the surface of the solid matrix such as high:density oligonucleotide arrays for capturing the PNA chimerae.

In another embodiment of the invention, a method for capturing a library of PNA-substrate chimerae is disclosed. This embodiment captures these libraries on microparticle arrays. Here, pre-formed planar arrays of encoded particles are used to capture corresponding PNA-substrate chimerae prior to performing on-chip biochemical assays. In another preferred embodiment, encoded particles captured by way of a displayed oligonucleotide to PNA-substrate chimerae are assembled after completion of biochemical reactions.

Figure 3:
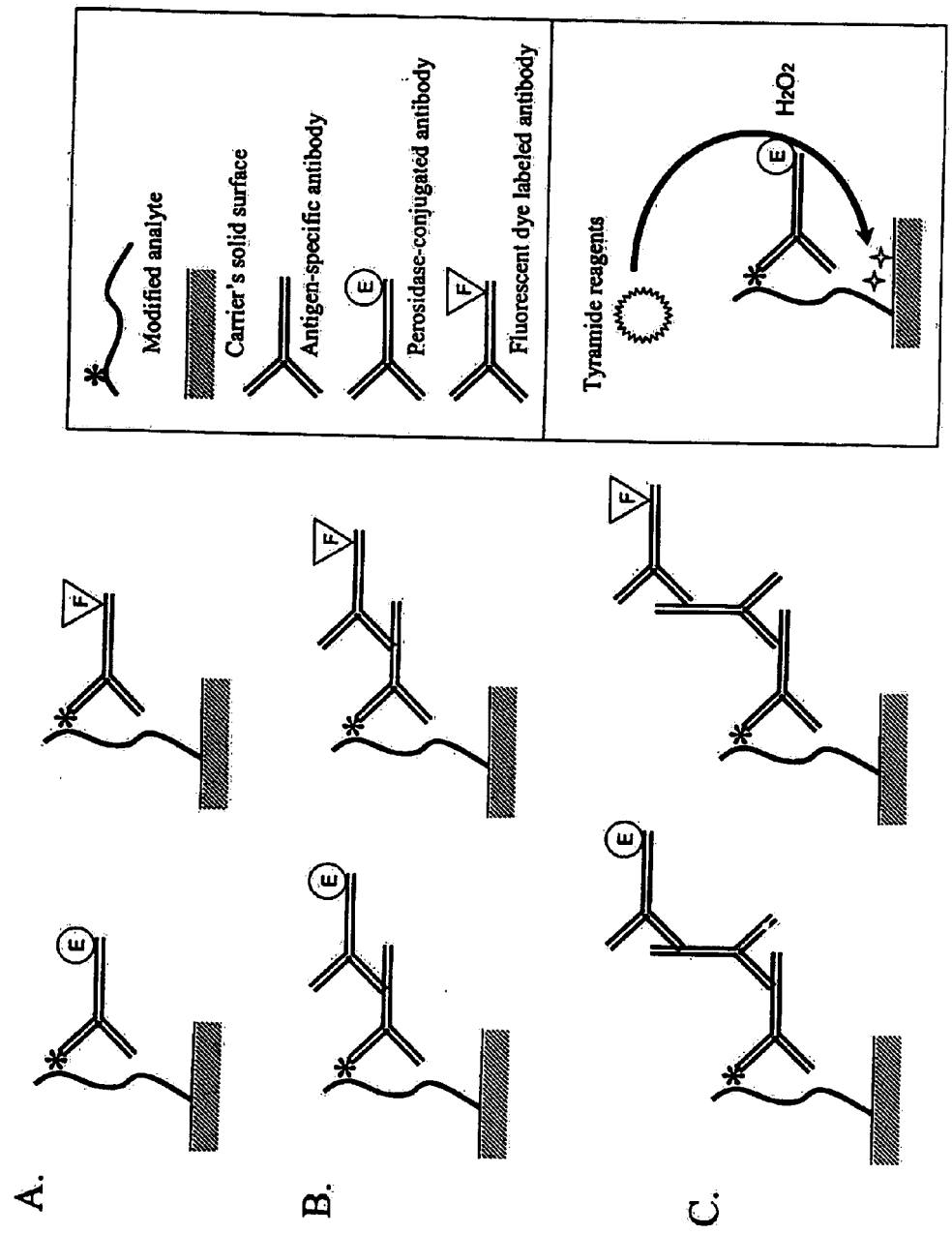
FIG. 3 shows detection of modified analytes/substrates by antibodies. Modified analytes captured on a solid surface may be detected by fluorescent (f) or peroxidase (E) labeled antibodies in the one antibody—(A); two antibody—(B); or three antibody—(C) formats.

In one embodiment, as illustrated in FIG. 3, modified chimerae captured on the carrier's solid surface may be detected by antibodies, as is known in the art. Modified chimerae may be detected by using modified substrate-specific antibodies that have been labeled. Antibodies may be derived from different classes or types of immunoglobulin molecules generated in culture media, in human or animal bodies. Signal from enzyme labeled antibodies, such as, for example, peroxidase labeled antibodies may be detected by using tyramide enhancement methods. Other similar labels and enzymes may be used. Such molecules are familiar to the skilled artisan. Fluorescent-dye labeled antibodies may be used for the detection of the modified substrates. In addition to single-antibody and dual antibody detection systems shown in FIGS. 3A and B, respectively, modified chimerae captured on the solid surface may be detected by using the three-antibody detection system (FIG. 3C). Briefly, primary antibodies bound to the modified substrate may be bound to secondary antibodies that are specific for the primary antibodies. The complex of the modified substrate, the primary antibody and the secondary antibody may be detected by using a labeled tertiary antibody. Furthermore, modified substrates may be detected by using specific chelating molecules, for example, gallium nitrilotriacetate (galliumNTA) which has high affinity to phosphate groups. Thus, gallium-NTA may be used in the detection of phosphorylated peptide of the PNA chimerae.

Conditions for hybridizing the PNA-substrate chimerae to DNA oligonucleotides on a solid matrix are known in the art; see, e.g., *Peptide Nucleic Acids: Protocols and Application*, edited by Nielsen, P. E. & Egholm, M., pg. 87-162, Horizon Scientific Press (1999). Methods known in the art provide a wide range of suitable hybridization conditions and solutions for capturing the chimera to the sensor oligonucleotides. In a preferred embodiment, the process for capturing the PNA-substrate chimerae to oligonucleotide-functionalized microparticles conforms to the conditions described hereinbelow. Pre-hybridization may preferably incubate the oligonucleotide-functionalized microparticles in a hybridization buffer (e.g. 10 mM sodium phosphate, 15 mM sodium chloride, 1 mg/ml BSA, and 0.1 mg/ml heat-denatured herring sperm DNA, 0.1% SDS, 10% formamide, pH 7.2), at about 45° C. with constant rotation for about 30 minutes. The BSA acts to block unoccupied sites on the surface of the microparticles during pre-hybridization. Other large non-specific proteins (such as non-fat dry milk) may be suitable as a substitute for BSA.

The hybridization step preferably utilizes oligonucleotide probes having fully complementary sequences to the capture portion of the chimera. PNA-substrate chimerae are added into a suspension of oligonucleotide-functionalized particles to a final concentration of 10 to 100 nM. Hybridization may be carried out at appropriate conditions, preferably at about 45° C. for about 1 hour with constant rotating. After hybridization, the hybridized microparticles are preferably washed with a washing buffer, more preferably, a high stringency buffer (e.g. 10 mM sodium phosphate, 15 mM sodium chloride, 0.1% SDS, pH 7.2) at about 45° C. for about 30 minutes with constant rotating. The microparticles are then washed with a first washing buffer (e.g. 10 mM sodium phosphate, 15 mM sodium chloride, pH 7.2), followed by washing with a second washing buffer (e.g. 100 mM sodium phosphate and 150 mM sodium chloride, pH 7.2) at about room temperature for about 10 minutes. The hybridization conditions and the washing frequency may be adjusted according to the base sequence of the capture portion of the chimerae. General protocols for PNA hybridization have been previously disclosed by Nielsen and Egholm (*Peptide Nucleic Acids, Protocols and Applications*, Edited by Peter E. Nielsen and Michael Egholm, Horizon Scientific Press (1999)).

Multiplexed assays of the present invention are particularly well-suited for determining the presence or activity levels of related entities, such as members of an enzyme family, related DNA-binding molecules, related receptor-ligand pairs or the like. One preferred family of enzymes whose activities may be determined in the multiplexed assays of the present invention are those that catalyze the phosphorylation and/or dephosphorylation of proteins. Phosphorylation of serine, threonine, and tyrosine residues is generally considered one of the most important regulatory mechanisms for intracellular events. Stimulation of receptors on cell membranes activate cascades of kinases, resulting in phosphorylation of various intracellular proteins. These reactions are reversible, enabling cells to respond in a dynamic way to a myriad of stimulatory signals. By using conventional methods, it is difficult to simultaneously determine activities for multiple kinases in the interconnected signal transduction pathways. Using the molecular constructs of the present invention, unique tags for each of multiple substrates can be prepared to permit multiplexed analysis. Upon phosphorylation, phosphorylated PNA chimerae, for example, can be sequence-specifically captured to oligonucleotide-functionalized color-encoded microparticles for detection using detectable ligands specifically reactive with the phosphorylated substrate, such as, for example, phospho-substrate binding proteins, phospho-substrate-specific antibodies or phospho-substrate binding chelate. Thus, activities of multiple kinases can be simultaneously determined in tissues and cells and other samples.

Figure 4:
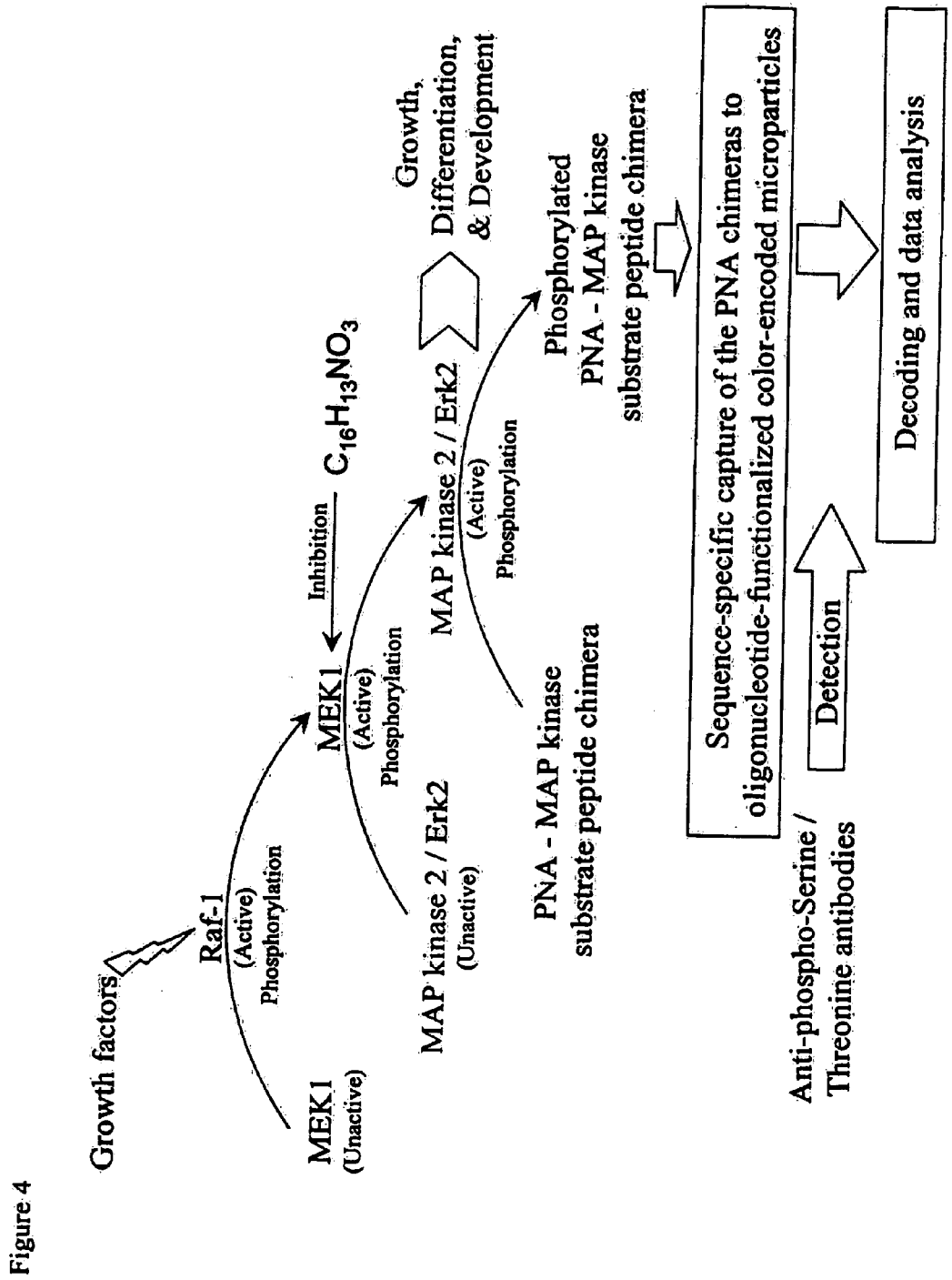
FIG. 4 shows the MAP kinase signal transduction pathway and reporter chimerae used to identify activity of specific kinases in the MAP kinase pathway.

One example of measuring the activity of a family of kinase proteins is schematically shown in FIG. 4. Here, the Raf proteins (Raf-1, A-Raf, and B-Raf) are serine-threonine kinases with homology to the PKC family, containing an amino-terminal regulatory domain and a carboxy-terminal catalytic domain. Members of the Raf family bind to Ras proteins resulting in their translocation to the plasma membrane, and subsequent activation. By phosphorylation of inactive MEK1 kinase, Raf kinases activate MEK1 kinase that, in turn, activates MAP kinase 2/Erk2. Raf kinases mediate the transduction of signals from Ras to MAP kinase. Regulation of these signaling complexes has been recently reviewed by Kolch (*J. Biochem* (2000), 35:289-305).

Activity of MAP kinase 2/Erk2 may be determined by using PNA-MAP kinase substrate peptide chimerae. The phosphorylated PNA-peptide chimerae may be sequence-specifically captured to oligonucleotide-functionalized color-encoded microparticles followed by detection of the phosphorylated serine/threonine moiety. By adding kinase inhibitors, such as, for example, 2'-amino-3'-methoxyflavone ($C_{16}H_{13}NO_3$), specific kinases may be inhibited in the signal transduction pathway (See FIG. 4). Thus, cascade kinase assays may be used with the molecular constructs of the present invention to detect kinase activity in cell samples. Such assays are valuable in detecting aberrant kinase activities associated with disease conditions and stages of disease. Many important growth factors use Ras/Raf signal transduction pathways to stimulate cells to multiply and the signaling complexes have been found to have abnormal activity in certain cancers. These assays are also useful in methods associated with drug discovery and studies of signal transduction.

A second non-limiting example for determining multiple kinase activities relates to the JAK (Janus-family tyrosine kinase) family of non-receptor tyrosine kinases. JAKs are associated with cytokine receptors inside the cell, and are activated by extracellular cytokines. JAK kinases (JAK1, JAK2, JAK3 and Tyk2) have a kinase domain and a pseudokinase domain which is not enzymatically active. Cytokine binding induces cytokine receptor dimerization, activating associated JAKs which phosphorylate the receptor itself. The phosphorylated receptor then serves as a docking site for the SH2-containing STATs (signal transducers and activators of transcription). JAK1 is essential for signaling from IL-2, IL-6 (gp130), and interferon (IFN) receptors. JAK3 is required for signaling through cytokine receptors that share a common g chain. JAK2 is required for signaling through a different subset of cytokine receptors. In addition, JAKs also activate the Ras-MAP kinase pathway, and through Tec, the PI-3 kinase pathway in the cell. STATs, the principal effectors of JAKs, are latent cytosolic transcription factors. Once phosphorylated by JAK kinases, STATs dimerize in a head-to-tail fashion by way of their SH domains. STAT1 is a critical mediator of IFN signaling, STAT4 is specific to IL-12, STAT6 is activated primarily by IL-4 and IL-13, while STAT5A and STAT5B appear to be most important in regulation of growth hormone and prolactin. These STAT-induced phosphorylation events also potentate specific transcription reactions. Regulation of the gp130/JAK/STAT signaling pathways have been reviewed by Heinrich et al. (*Biotech. J.* 334:297-314 (1998))

Figure 5:
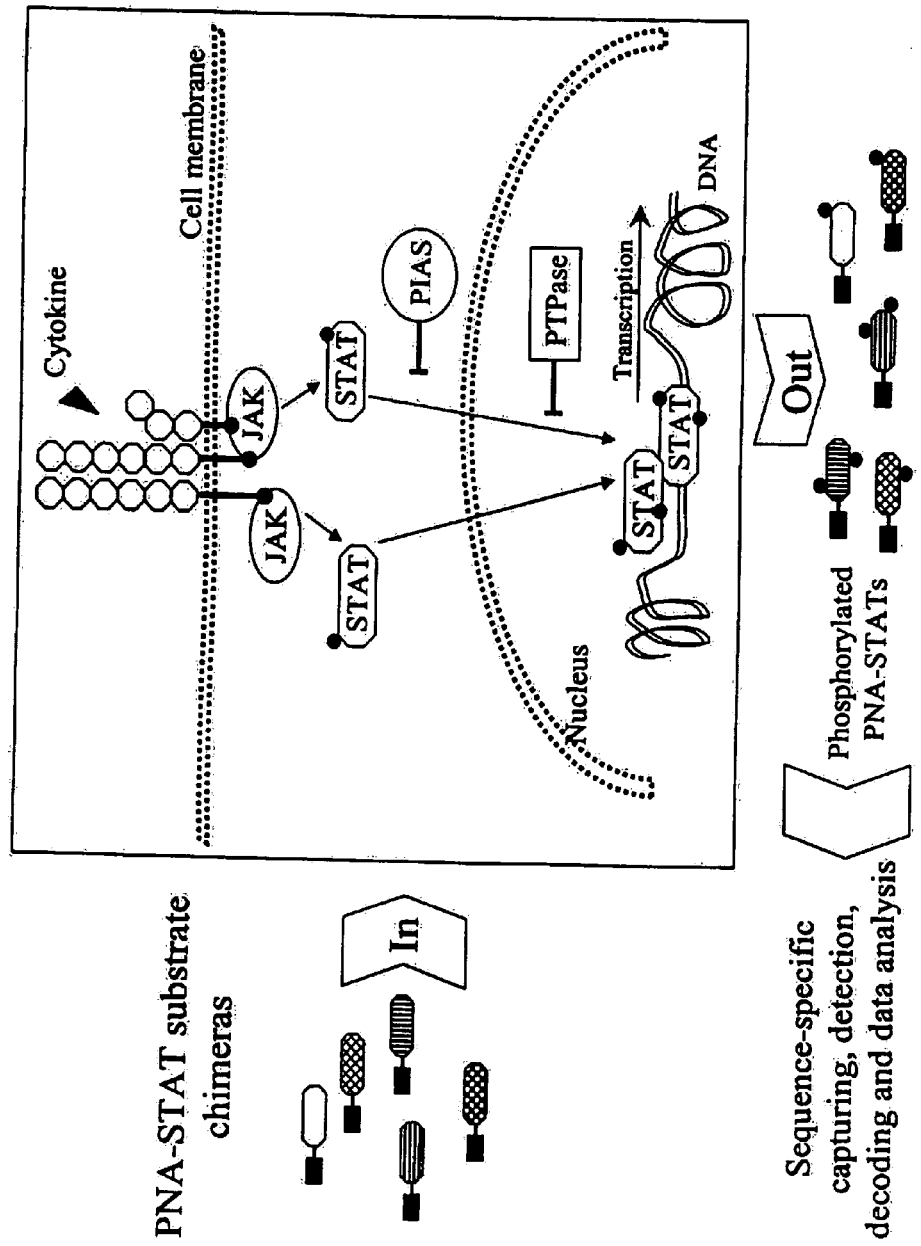
FIG. 5 shows a schematic illustration of a cell based assay using PNA-STAT chimerae to determine kinase activity in JAK kinase-mediated signal transduction pathways.

A collection of PNA-substrate chimerae of the present invention can be employed to simultaneously monitor or detect the activity levels of multiple JAK or STAT proteins. By using PNA-STAT chimerae, phosphorylation of multiple STATs may be simultaneously determined in cell-based assays. A method for measuring multiple STAT protein activity levels begins by adding various kinds of PNA-STAT chimerae, including cell-invading PNA chimerae, into a cell culture of interest. In response to stimulation from a cytokine or other compound of interest, JAK-STAT signal transduction pathways are activated, resulting in phosphorylation of STAT proteins, including PNA-STAT chimerae. When cells are lysed by standard means, the PNA-STAT chimerae are released into solution. The PNA-STAT chimerae may then be sequence-specifically captured to oligonucleotide-functionalized microparticles and detected. Hybridization of PNA chimerae to oligonucleotides on microparticles may be carried out in a test tube (in-tube hybridization) or on silicon chips with microparticle arrays (on-chip hybridization). This embodiment of the invention is schematically illustrated in FIG. 5.

In addition to PNA-STAT chimerae, other kinds of PNA-protein chimerae, such as, for example, PNA-JAK chimerae, and PNA-peptide chimerae containing epitopes of interest may be used in the cell-based functional assays for determining other effectors of other signal transduction pathways. Such assays are particularly useful for blocking kinase-activated transcriptional activity in order to mediate disease conditions. The JAK/STAT signaling pathway in humans has been linked to the development of certain leukemias. In addition, these assays are useful in drug discovery assays and functional proteomics assays.

Figure 6A:
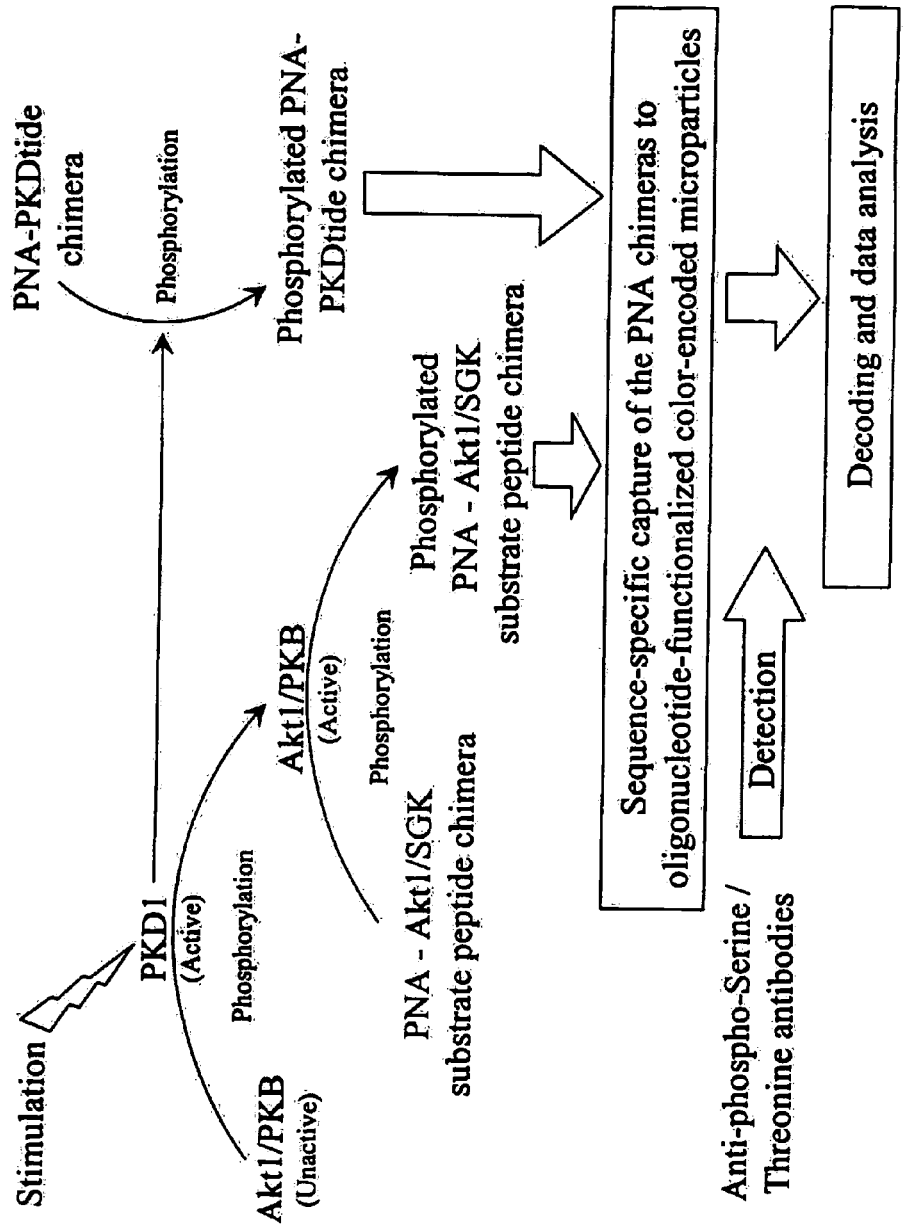
FIG. 6 shows a schematic illustration for detecting specific kinase activity for PKD1 and Akt1/PKB kinases (A), and may be used to analyze the Akt/PKB signaling pathway in cell-based assays (B).

Yet another example of detection of multiple kinase activities relates to Akt, also referred to as PKB and RAC, which is a protein with an active role in the regulation and occurrence of apoptosis. The Akt/PKB protein kinase is activated by insulin and various growth factors. It functions in the Wormannin-sensitive pathway, involving PI-3 kinase. Akt/PKB contains an amino terminal pleckstrin homology (PH) domain that binds phosphorylated lipids of the membrane in response to activation of PI-3 kinases. Akt/PKB is activated by phospholipid binding and PKD1 phosphorylation at threonine 308 in the activation loop and at serine 473 in the C-terminus region. Akt/PKB functions to promote cell survival by inhibiting apoptosis by means of its ability to phosphorylate and inactivate several targets, such as Bad, Forkhead transcription factors (FKHR), GSK-3, and Caspase-9. Using a PNA-PKDtide chimera and a PNA-Akt/SGK peptide chimera as substrates, activities of PKD1 and Akt/PKB can be determined simultaneously in tissue and cells. Such a method comprises adding the PNA peptide chimera to a sample to allow phosphorylation to occur. After phosphorylation, the phosphorylated PNA peptide chimerae may be sequence-specifically captured to oligonucleotide-functionalized color-encoded microparticles, including color-encoded magnetic particles. The captured phosphorylated peptides may then be detected using a phosphorylated peptide specific ligand, or a phosphorylated peptide-specific antibody. A schematic illustration of this process is shown in FIG. 6A.

Figure 6B:
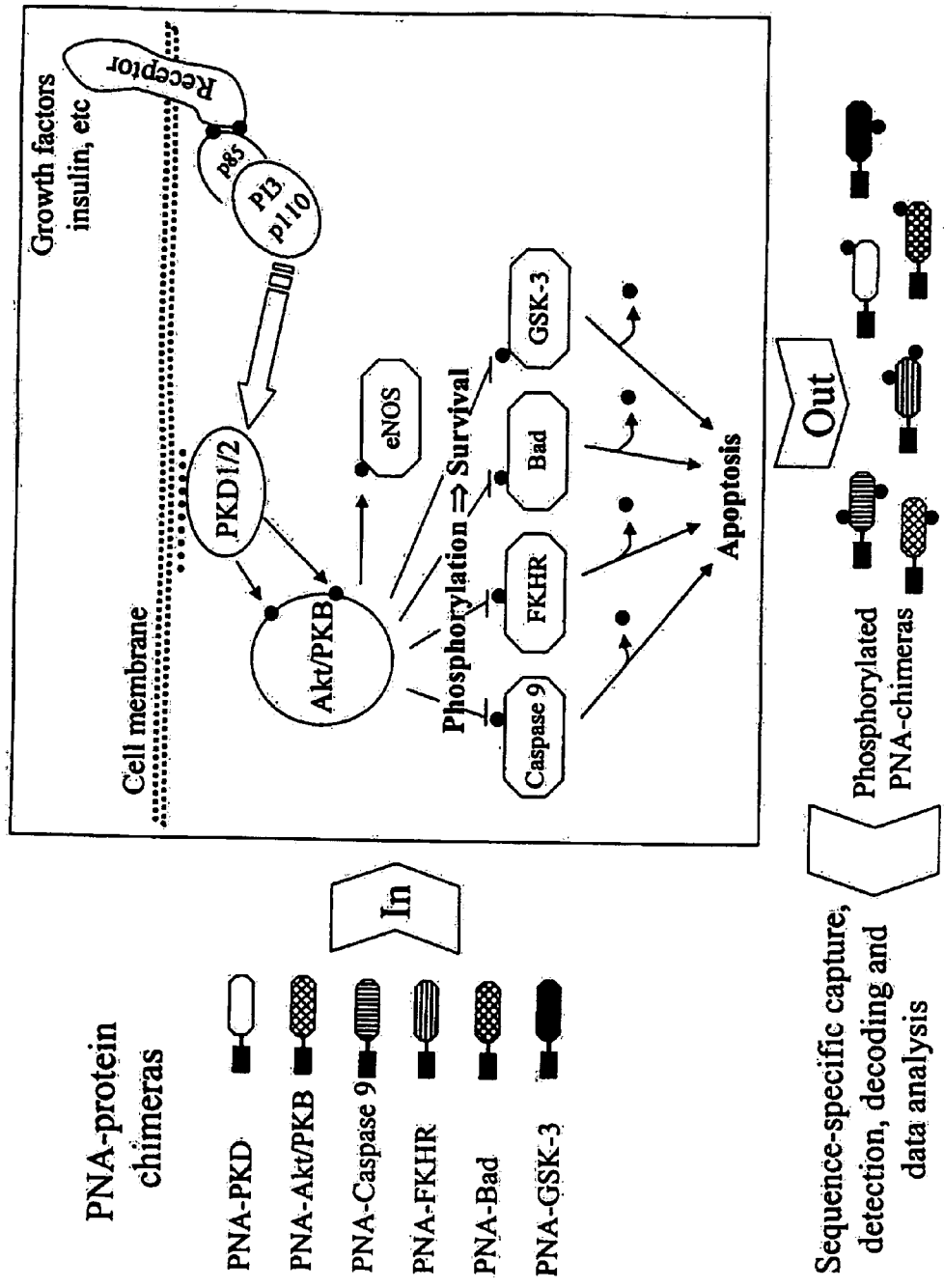

In addition, as illustrated in FIG. 6B, Akt/PKB signaling may also be systematically investigated in a PNA chimera cell-based assay. This method comprises adding one or more PNA protein chimerae having substrate portions which are substrates of PKD1/2 and/or Akt/PKB, such as, for example, PKD, Akt/PKB, Caspase 9, FKHR, Bad, and GSK-3 to a cell sample of interest. At this point, the internal kinase activity is directly measured by harvesting PNA chimerae to determine the activation state and/or levels of these proteins. Alternatively, the cell sample can be treated with a modulator of the activity, such as insulin or growth hormone, for example. Binding of these modulators to the cell surface receptors may activate PDK1/2 located on the interior side of the cell membrane. Activated PDK1/2 phosphorylates Akt/PKB that, in turn, phosphorylates Caspase 9, FKHR, Bad, and GSK-3 proteins. The cells are then lysed, thereby releasing the PNA-protein chimerae. The PNA chimerae are hybridized to sequence-specific oligonucleotide-functionalized microparticles or other solid matrix. The modified substrate portion of the chimera is then detected by standard means. This assay is schematically illustrated in FIG. 6B. This assay is useful in detecting aberrant kinase activity associated with disease conditions and stages of disease. Previous studies have shown that mutant presenilin-1 gene induces apoptosis and down regulates Akt/PKB in patients with Alzheimer's disease (Wehl, et al. *J. Neuroscience* 19: 5360-5369 (1999)). The assay is also useful in diagnosing such disease conditions.

Figure 7:
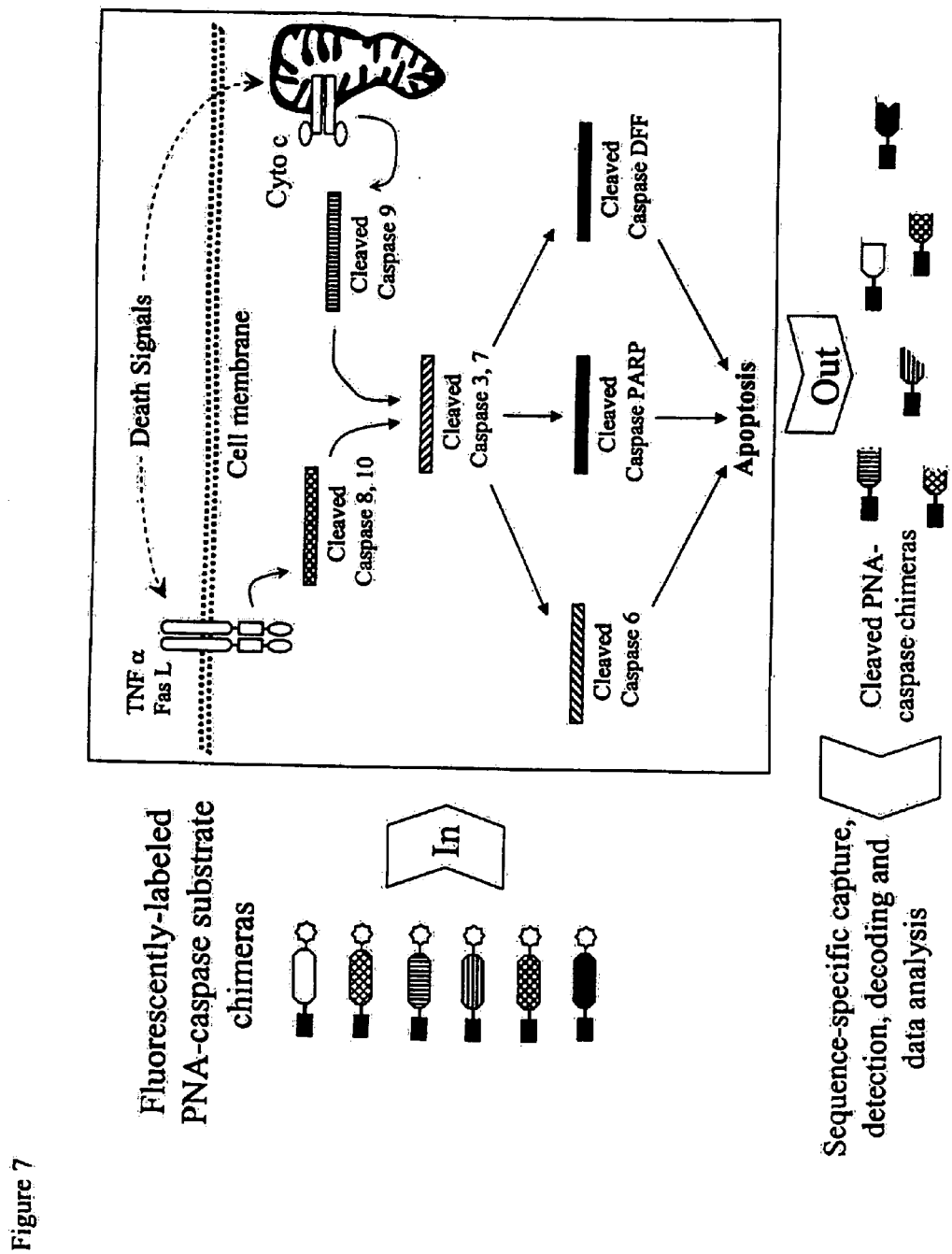
FIG. 7 shows a schematic illustration for detecting multiple caspase activities using PNA-caspase chimerae.

Another family of proteins which can be analyzed by the method of the present invention are caspases. This family of enzymes is associated with the regulation of apoptosis, i.e. programmed cell death. Pro-apoptotic signals such as the release of mitochondrial cytochrome c promote autocatalytic activation of initiator caspases, such as caspase 8, 9 and 10. Once activated, these caspases cleave and activate downstream effectors such as caspases 3, 6 and 7, which in turn cleave cytoskeletal and nuclear proteins of the apoptotic cells. Other pro-apoptotic stimuli include binding of Fas ligand and TNF-α to cell surface receptors, DNA damage and stress to the endoplasmic reticulum (ER) inside the cell. Fas and TNF receptors activate caspases 8 and 10, damaged DNA leads to activation of caspase 9, whereas ER stress leads to the calcium-mediated activation of caspase 12. This complex scheme is illustrated in FIG. 7. The multiplexed assays of the present invention using PNA chimerae provide an effective tool to simultaneously monitor the effects of signaling events or cell function.

In one embodiment of the present invention, PNA-caspase chimerae are prepared, so that each of the chimerae contains a cleavage site of a defined pro-caspase. The PNA-caspase chimerae also contain at least one labeled tag, preferably two tags, such as, for example, a fluorescent tag and a polyhistidine tag, for detection. These two tags are located on either side of the cleavage site of the peptide substrate. Mixtures of cell-permeable PNA-caspase chimerae are added to the cell sample of interest. Pro-apoptotic stimuli, such as TNF-α or Fas ligand, may be added to selected samples to trigger programmed cell death signals. Activation of the apoptotic pathways results in cleavage of various caspase substrates, including the PNA-caspase chimerae. One of the fluorescent dyes contained in double-labeled PNA chimerae is eliminated by caspase-catalyzed cleavage. When the cells are lysed, the PNA chimerae are released. The released PNA chimerae are then captured onto oligonucleotide-functionalized microparticles. Fluorescence from single tagged-cleaved product or from double-tagged uncleaved product is determined and analyzed.

Figure 8:
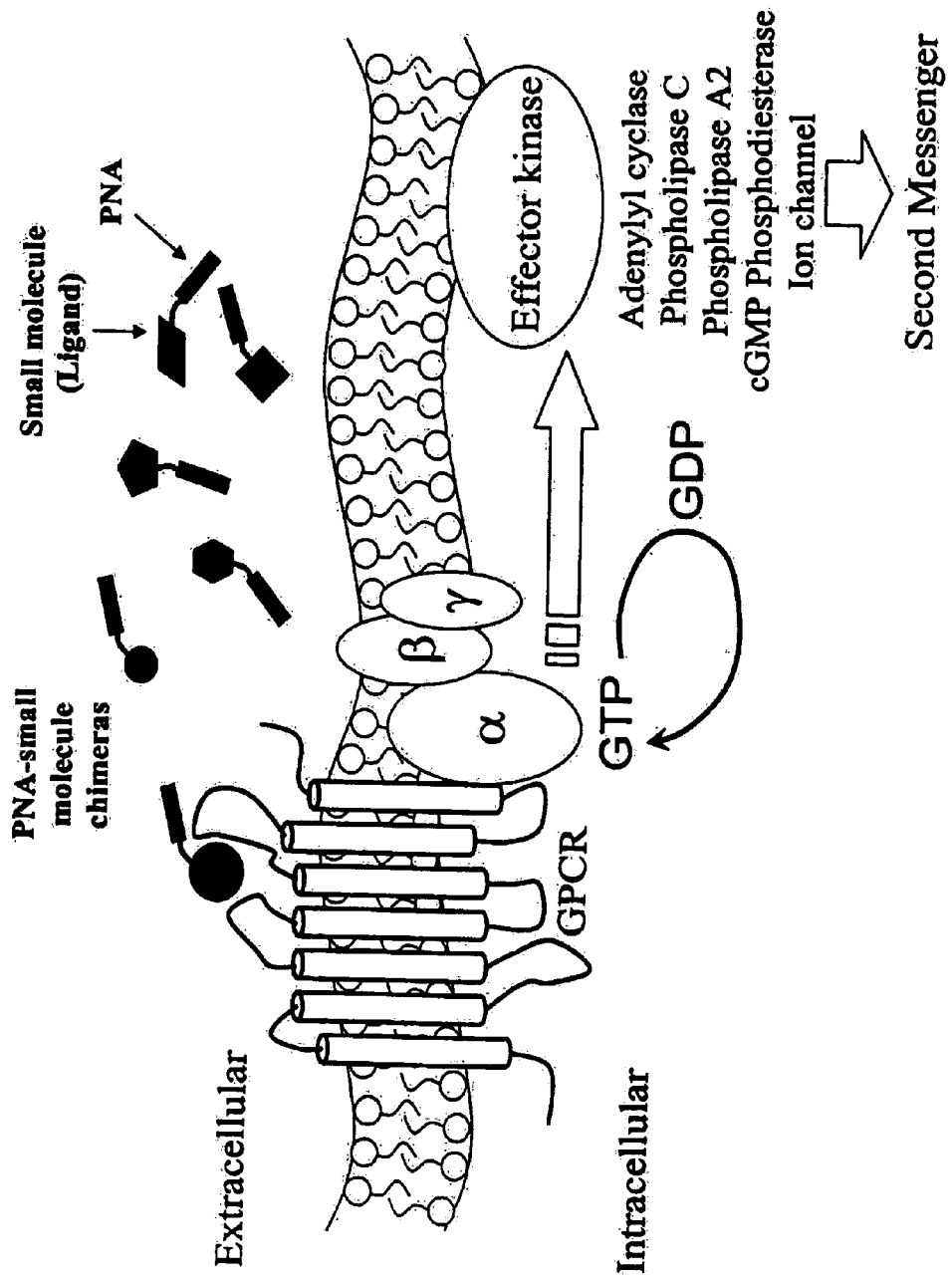
FIG. 8 shows a schematic illustration for a method of identifying new drugs targeting GPCR using PNA-small molecule chimerae in cell-based assays.

In another embodiment of the invention, the method is useful in the identification of new drugs. In this embodiment, small molecule drug candidates are conjugated to PNAs and tested for efficacy. Such PNA-small molecule chimerae can be used in high-throughput screening of ligands for drug discovery. One example of this method is schematically illustrated in FIG. 8. Here, a library of PNA-small molecule chimerae is prepared for screening. Each of the chimerae contains a defined small molecule as the substrate domain and a PNA oligomer with known base sequence as the anchoring domain. Mixtures of the PNA-small molecule chimerae are added into cell culture of interest and are permitted to bind chimerae to the target of interest and trigger activation of the target cells. FIG. 8 shows G-protein coupled receptors (GPCR), which trigger signal transduction. After activation, the effective PNA-small molecule chimerae are captured to their complementary oligonucleotides displayed on color-encoded microparticles. Detection may be achieved by detecting a tag on the small molecule or by binding of a small molecule-specific ligand which is detectable. It may also be desirable to strip the captured small molecule-PNAs from the particles by incubation in a solution at a temperature higher than the melting temperature of the duplex formed by the capture and anchor domain. The recovered PNA-small molecule chimerae may then be further analyzed.

Figure 9:
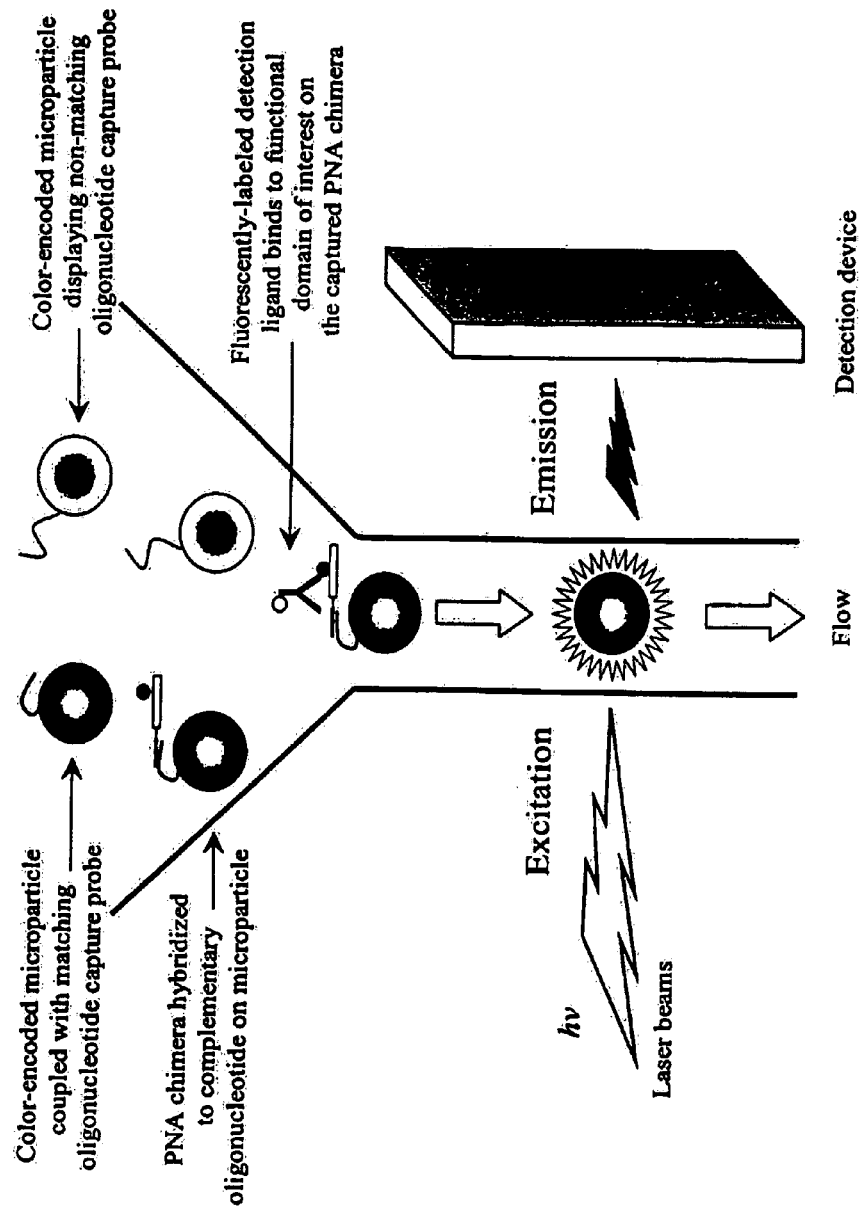
FIG. 9 shows a schematic illustration of PNA chimerae hybridized to complementary oligonucleotides on color-encoded microparticles detected by flow cytometry.

In addition to detection by fluorescence microscopy, planar arrays of PNA chimerae hybridized to complementary oligonucleotides on color-encoded microparticles, individual microparticle-displayed PNA-chimerae can be detected by flow cytometry. This embodiment is illustrated in FIG. 9. Accordingly, sequence-specific hybridization of PNA chimerae to oligonucleotides immobilized on color-encoded particles may be carried out in suspension. After hybridization, the particles are incubated with ligands having high binding affinity to modified substrate portions of the chimerae of interest. In addition, the ligand may contain a specific fluorochrome for detection. Alternatively, secondary detectable ligands may decorate the primary ligands that bind to the chimerae, ensuring that the emission wavelength of the detection fluorochrome is distinguishable from the fluorescence of the color-encoded particles. For detection of the PNA hybridization, particles are analyzed by flow cytometry. Different types of particles are identified according to their specific fluorescence. Particles having captured PNA chimerae may be identified according to specific fluorescence from the detection fluorochrome.

Figure 10:
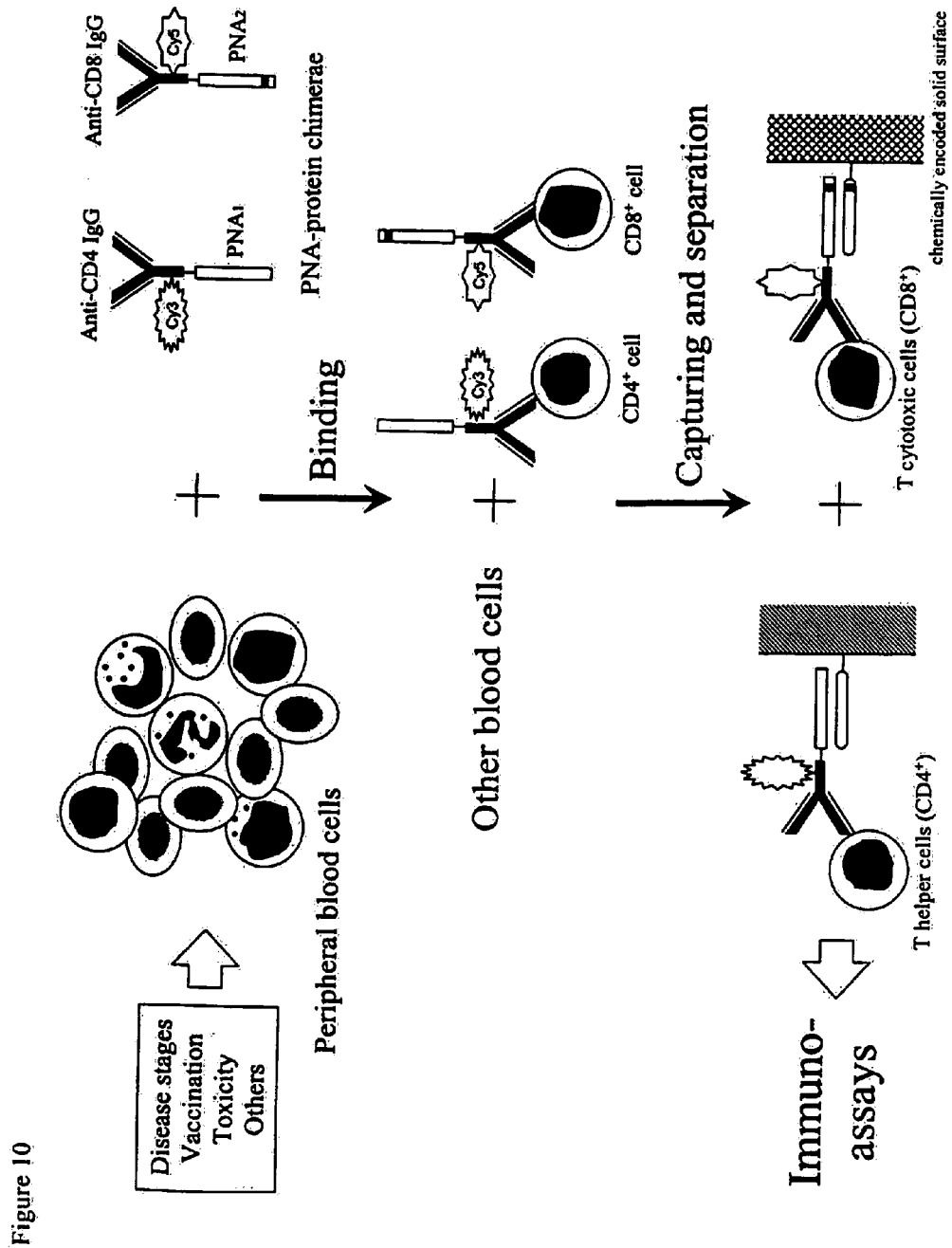
FIG. 10 shows a method of using PNA-antibody chimerae for detecting and isolating cells having specific proteins displayed on their cell surface.

In yet another embodiment of the present invention, the PNA chimerae are used to detect and isolate specific cells, i.e. cells presenting specific proteins or other identifying entities on their cell surface. For example, PNA-antibody chimerae are produced, wherein the antibody is specific for a cell surface receptor of interest. The antibody may be labeled with fluorescent dye in order to monitor the capture process. One example of this method is shown in FIG. 10. In this illustration, CD4+ cells and CD8+ cells are detected and captured. Cy3 and Cy5 are water-soluble cyanine dyes that are fluorescent labels for proteins, modified oligonucleotides and compounds containing primary amines.

In another embodiment of the invention, the substrate portion of the PNA-chimera comprises a nucleic acid binding domain. In this embodiment, the PNA-chimera is exposed to a detectable nucleic acid, which is suspected to be capable of interacting with the functional domain of the chimera. The bound nucleic acid is then captured onto the oligonucleotide captured on the solid matrix and detected. This embodiment may also be multiplexed.

The following examples illustrate production and use of the present invention. These examples are offered by way of illustration, and are not intended to limit the scope of the invention in any manner. All references described herein are expressly incorporated in toto by reference.

EXAMPLES

Example 1

Figure 11:
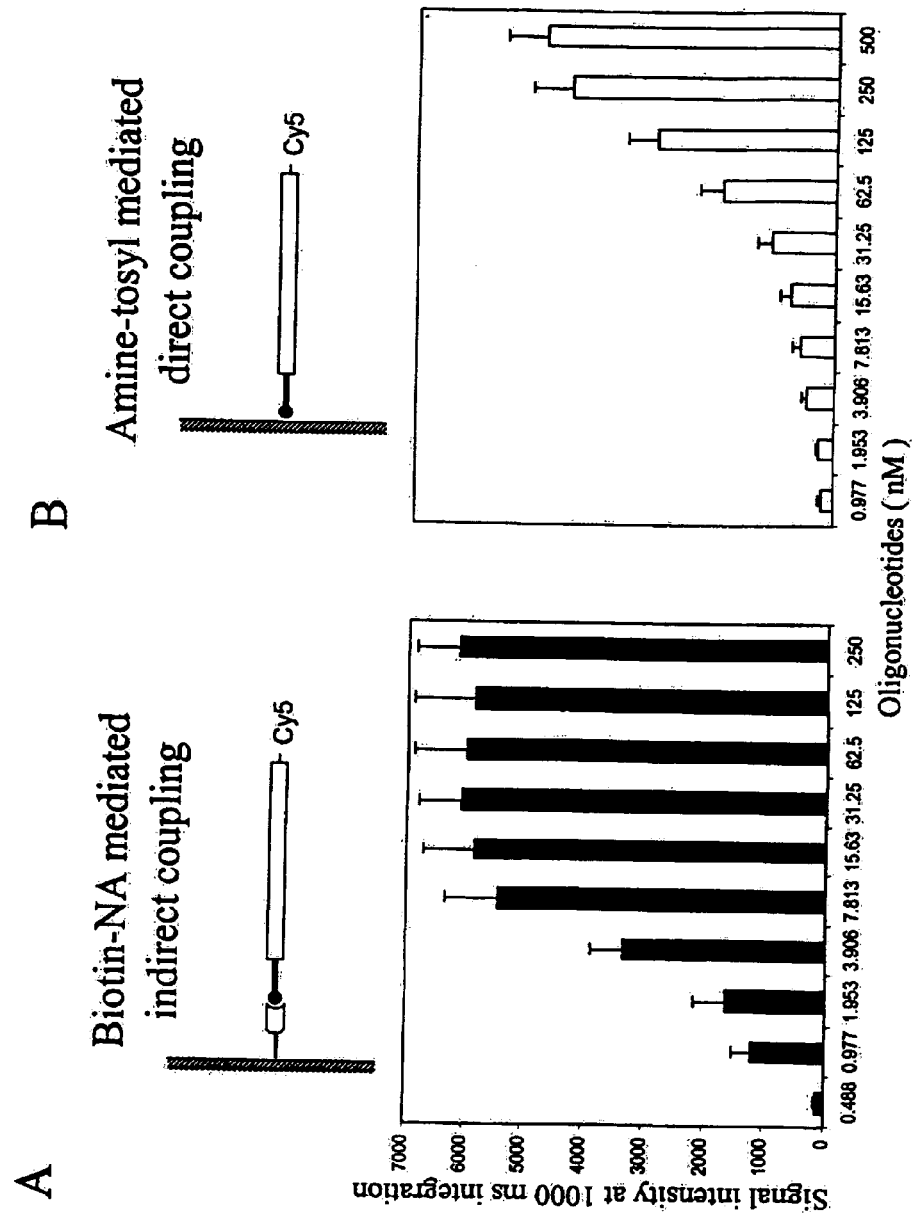
FIG. 11 shows two different approaches for immobilizing oligonucleotide probes to a solid surface, indirect coupling using Biotin-NeutrAvidin binding (A) and direct coupling using amine-tosyl reaction (B). Results for titration of biotin-NeutrAvidin mediated indirect coupling of oligonucleotides onto solid surfaces and of direct conjugation of amine-tosyl direct coupling of oligonucleotides onto solid surfaces are shown under the appropriate diagram.

Coupling of DNA Oligonucleotides to the Surface of Microparticles for Capturing of PNA Chimerae Two different approaches may be used to attach oligonucleotide probes to a solid surface, e.g., color-encoded microparticles. In the first approach, indirect coupling, biotinylated oligonucleotides interact with streptavidin or its derivatives, conjugated to the solid surface. The process for conjugation of proteins to solid surfaces, such as microparticles, is known in the art (*Bioconjugate Techniques*, edited by Greg T. Hermanson, Academic Press, 1995). As shown in FIG. 11A, biotinylated oligonucleotides were efficiently coupled to NeutrAvidin, a modified form of streptavidin, which has been conjugated to the microparticles. Briefly, an increasing amount of Cy5-labeled biotinylated oligonucleotides (0.488, 0.977, 1.953, 3.906, 7.813, 15.63, 31.25, 62.5, 125, and 250 nM) were incubated given a fixed number of color-encoded NeutrAvidin-functionalized beads. The coupling reaction was carried out in PBS at room temperature for 30 minutes. After coupling, unbound oligonucleotides were removed by washing the beads using PBST. Unoccupied sites on the surface of the microparticles were blocked using BSA (10 mg/ml in 100 mM phosphate buffer, pH 7.4). After washing with 100 mM phosphate buffer, pH 7.4, the microparticles may be stored in the storage buffer at 4° C. Different types of beads were then combined into a test tube for assembly into microparticle arrays. The arrays were examined under a fluorescence microscope. Results for the titration series of NeutrAvidin are shown in FIG. 11A. Coupling of 31 nM of biotinylated oligonucleotides may be able to saturate all of the binding sites on the NeutrAvidin-functionalized beads (3.2 μm diameter) show that, as the oligonucleotide concentration increased, the Cy5 signal intensity recorded with 1000 ms integration time increased from approximately 100 to 6000. The error bars shown in FIG. 11A represent standard deviations of the means.

Oligonucleotides may also be directly conjugated to the surface of solid carriers by chemical reaction forming a covalent linkage. An amine group may be incorporated to the 5' terminal end of oligonucleotides according to known prior art methods. Conjugation of oligonucleotides to tosyl-activated microparticles was achieved in a single step reaction. Examples of amine-tosyl mediated direct coupling are shown in FIG. 11B. Briefly, increasing amounts of Cy5-labeled amine-modified oligonucleotides (0.977, 1.953, 3.906, 7.813, 15.63, 31.25, 62.5, 125, 250, and 500 nM) were incubated with a given fixed number of color-encoded tosyl-activated beads. Generally, the coupling reaction was carried out in 100 mM sodium phosphate, pH 7.4 at 37° C. overnight. After coupling, unbound oligonucleotides were removed by washing the beads using PBST, and the microparticles were incubated with bovine serum albumin (BSA) (10 mg/ml in 500 μl of 100 mM phosphate buffer, pH 7.4) to block unoccupied sites on the surface of the particles. Blocking was performed at 37° C. for 1 hour under constant rotation. Different types of beads were then combined into a test tube for assembly into microparticle arrays. The arrays were examined under a fluorescence microscope. Results for the titration series in FIG. 11B show that as the concentration of oligonucleotide increased, the Cy5 signal intensity, recorded at 1000 ms integration increased from about 100 to 5000. The error bars, shown in FIG. 11B, represent standard deviations of the means. Coupling by using 250 nM of amine-labeled oligonucleotides may be able to saturate all of the binding sites on the tosyl-activated coated beads (3.2 μm diameter). After washing with 100 mM phosphate buffer, pH 7.4, the oligonucleotide-functionalized microparticles may be saved in storage buffer (100 mM phosphate, 1 mM EDTA, with 0.05% sodium azide) at 4° C. under constant rotation.

Example 2

Purification of Biotinylated PNA Oligomers

Figure 12:
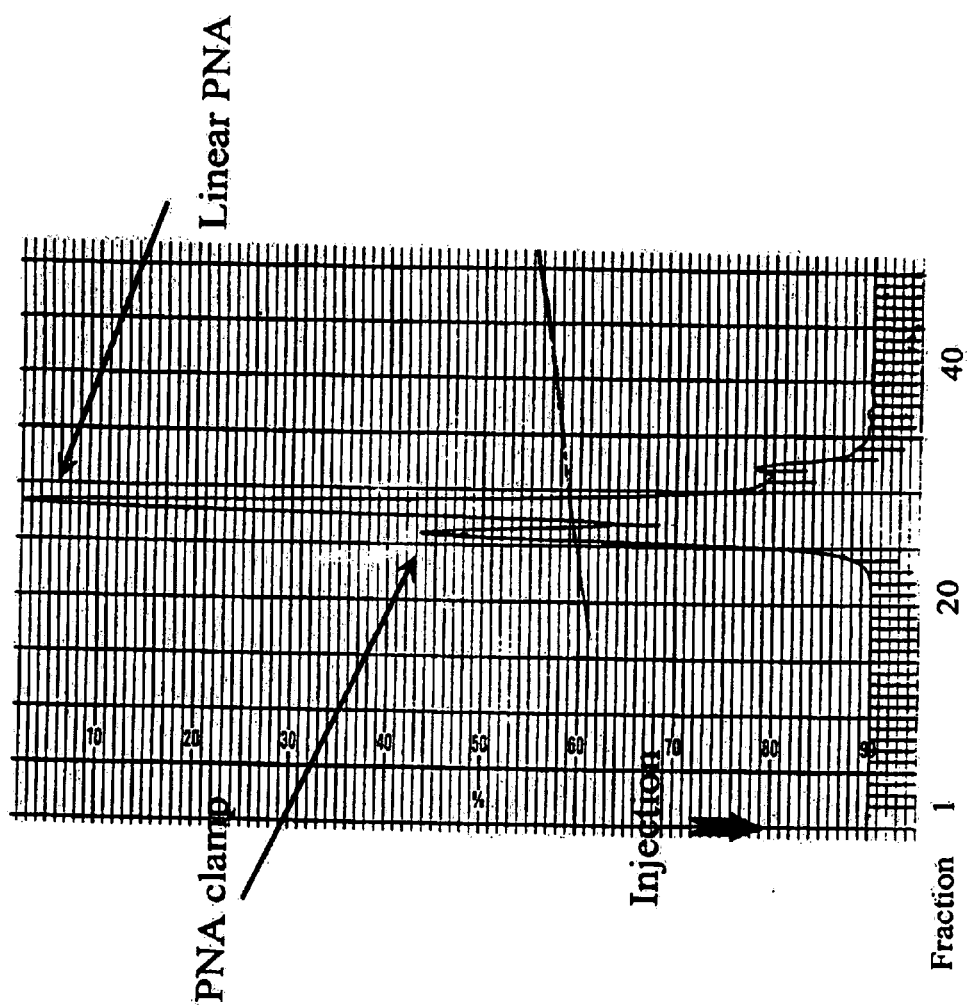
FIG. 12 shows high-pressure liquid chromatography purification of two types of biotinylated PNA oligomers.

Synthetic PNA chimerae may be purified by liquid chromatography. An example of high-pressure liquid chromatography (HPLC) purification of two biotinylated PNA oligomers is shown in FIG. 12. The biotinylated bis-PNA ("PNA clamp") and linear PNA have molecular weights of 4.3 kD and 7.5 kD, respectively. The PNA oligomers were separated on a gel filtration column in 10 mM Tris-buffer, pH 7.5, with 125 mM NaCl, monitoring the chromatographic profile at a wavelength of 260 nM. Forty-eight (48) fractions of 0.5 ml eluate were collected at a flow rate of 0.5 ml/min. Two unique peaks, short and tall, were identified respectively, corresponding to a 4.3 KD PNA clamp (Fraction 25) and a 7.5 KD linear PNA (Fraction 28). Molecular weights of the purified PNA oligomers were confirmed by mass spectroscopy analysis.

Example 3

Spectrophotometric Profile of Purified PNA-Peptide Chimerae

Figure 13A:
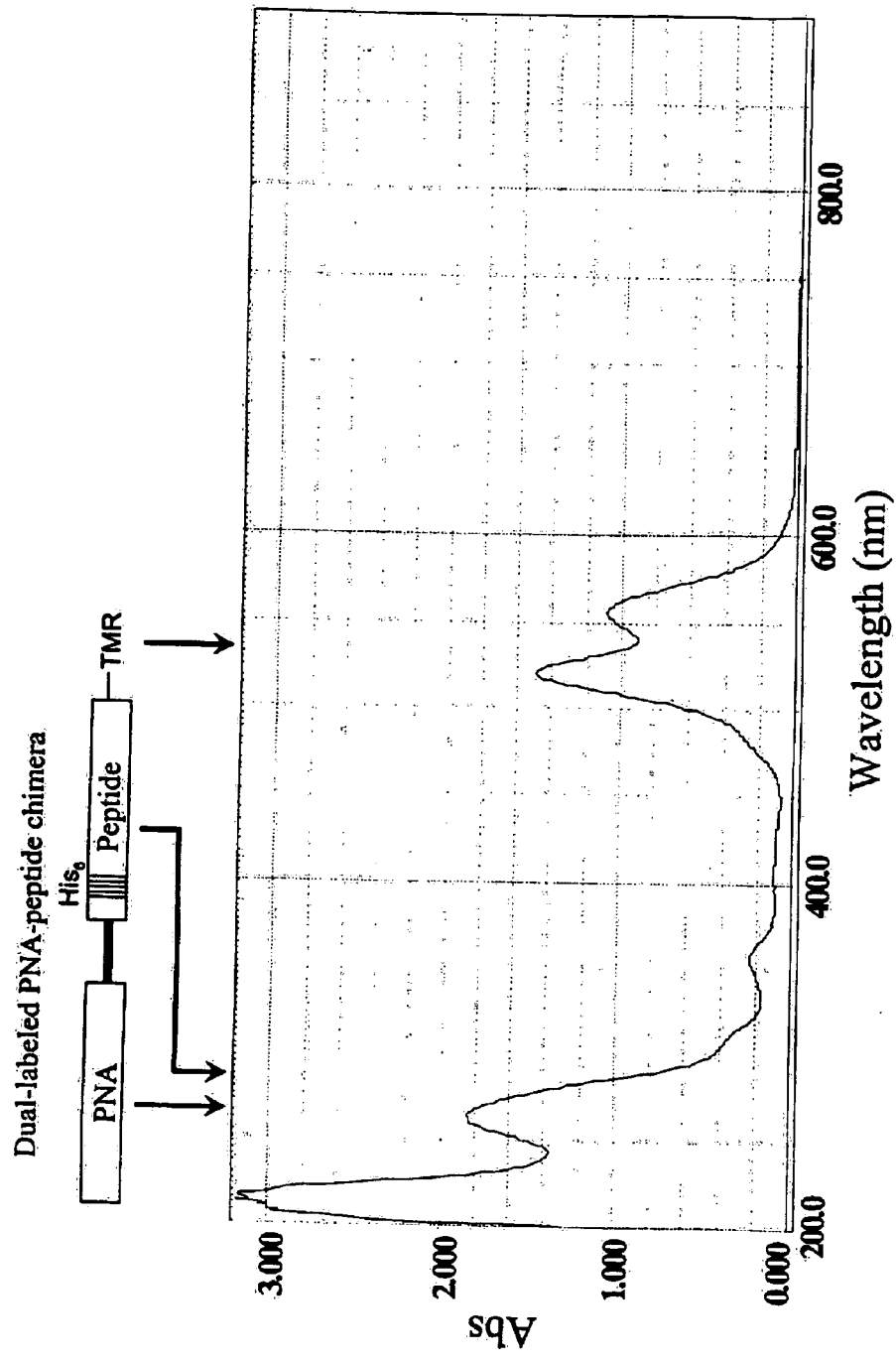
FIG. 13 shows a purified tetramethyl rhodamine (TMR) labeled PNA-peptide chimera (A) and a Cy5-labled PNA-small molecule chimera (B) and their respective spectrophotometric profiles.
Figure 13B:
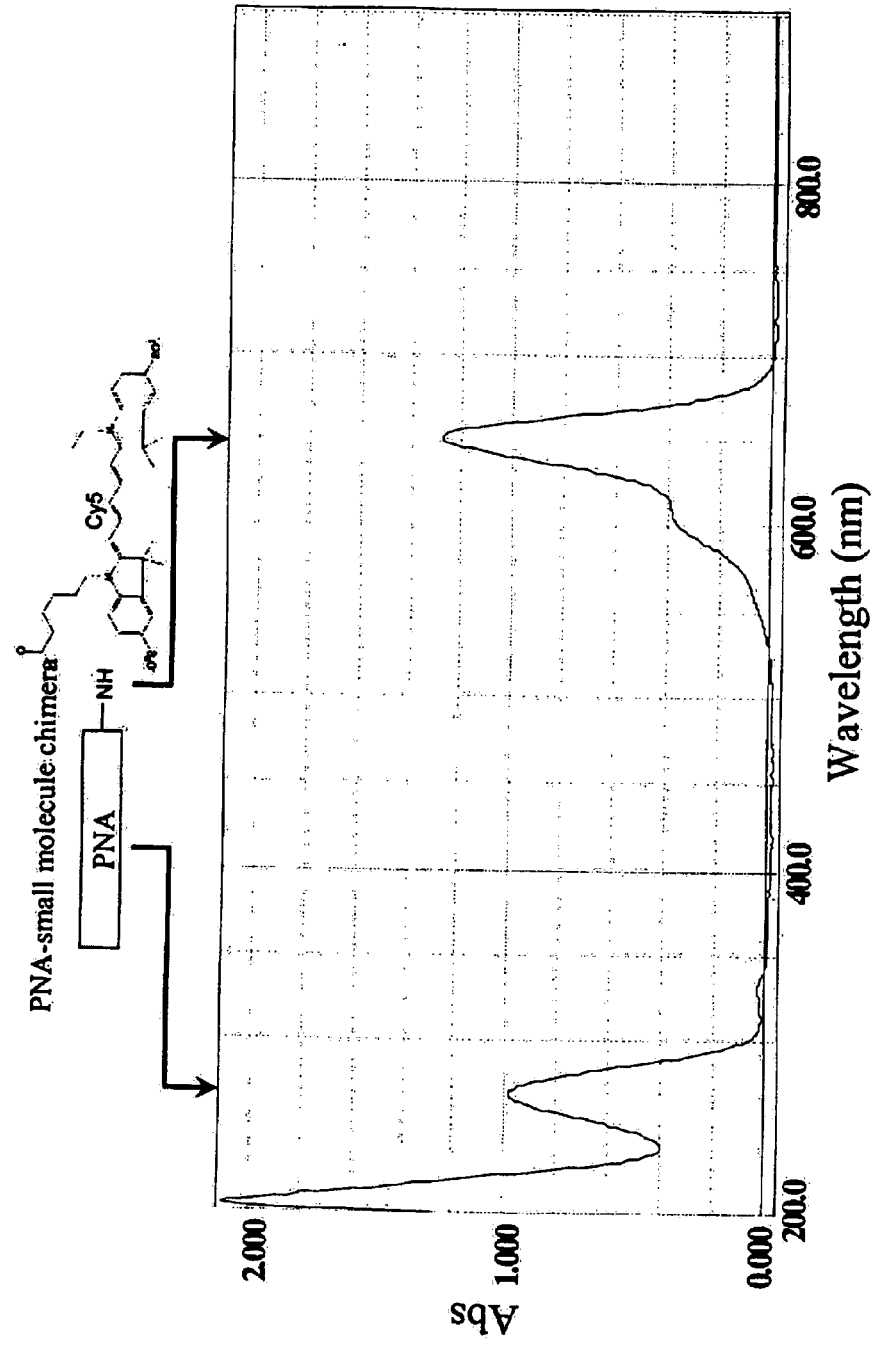

To verify the labeling of PNA chimera with fluorophores, spectrophotometic profiles of the purified PNA chimerae were recorded using scanning spectrophotometers. Spectrophotometric profiles for the purified tetramethyl rhodamine (TMR)-labeled PNA-peptide chimera and Cy5-labeled PNA, shown in FIGS. 13A and B, respectively display the distinct absorption characteristics for the PNA and the fluorescent dyes. The peak in the wavelength range of 250-300 nm corresponds to the PNA with or without peptide, whereas the TMR label (FIG. 13A) is identified by a peak ranging between 500 and 550 nm, and the Cy5 label (FIG. 13B) by a peak in the 625-675 nm wavelength range.

Example 4

Figure 14:
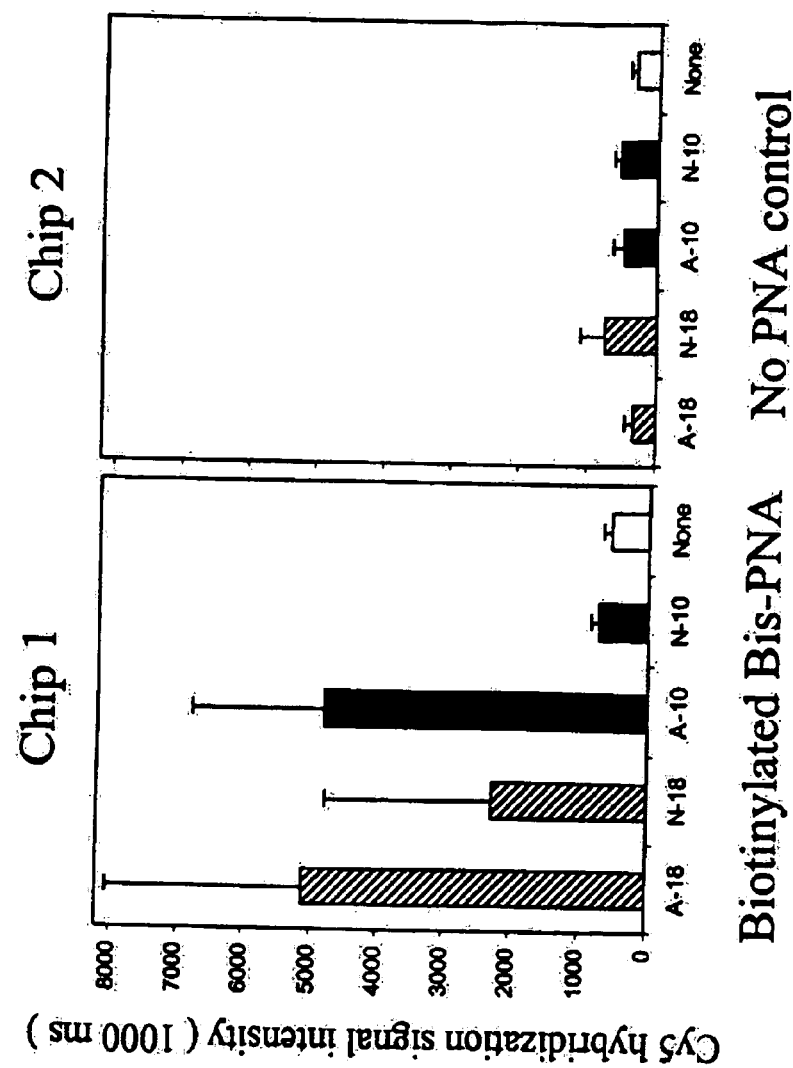
FIG. 14 shows the results of on-chip hybridization assays testing sequence-specific capturing of biotinylated bis-PNA oligomers to various oligonucleotides immobilized on microparticle arrays.

On-Chip Hybridization of Bis-PNA Oligomers to DNA Oligonucleotides on Microparticle Arrays On-chip hybridization assays were performed to ascertain the sequence-specific capture of bis-PNA oligomers to DNA oligonucleotides immobilized on microparticle arrays. Briefly, the bis-PNA oligomer was a biotinylated PNA clamp with 12-13 thymine bases on each arm. Prior to hybridization, four types of biotinylated oligonucleotides were coupled to NeutrAvidin-functionalized microparticles, the respective oligonucleotides containing an 18-mer oligoadenine (A-18), an unrelated sequence of 18 nucleotides (N-18), a 10-mer polyadenine (A-10), and an unrelated sequence of nucleotides (N-10). After coupling, all of oligonucleotide-functionalized microparticles along with a negative control particle containing no oligonucleotide capture probe were combined into one tube for assembly of microparticle arrays on silicon chips. Chips were first pre-hybridized in a buffer containing 90 mM NaCl, 83 mM guanidine thiocyanate, 8 mM $MgCl_2$, 17 nM EDTA, 0.1% biotin, 0.1% Tween-20, 70 mM Tris-HCl, at pH7.5, at 40° C. for 20 min. Then, the biotinylated bis-PNA was added into the pre-hybridization buffer to a final concentration of 200 nM. Hybridization was carried out in a humidified chamber at 40° C. for 1 hour. The negative control chip received no PNA in the hybridization buffer. Upon completion of hybridization, chips were washed with 100 mM NaCl, 10 mM Tris-HCl, at pH 7.5, 0.1% Tween-20, at room temperature for 10 min. For detection of the biotinylated PNAs hybridized to particle-displayed oligonucleotide probes, the chips were incubated with Cy5-conjugated streptavidin (20 μg/ml) in 100 mM NaCl, 100 mM sodium phosphate, pH 7.5, at room temperature for 30 min. After washing with 15 mM NaCl, 10 mM Tris-HCl, pH 7.5, arrays were examined by using a fluorescence microscope. Several images were taken from the same chip using different filters that pass through specific wavelengths. The identity of the particles was determined according to their respective color codes. The assay signals of the beads from the $CY_5$ image of the ship were merged with the decode particles. Assay signals from the matched A-10 and A-18 and from the unmatched N-10 and A-18 particles were extracted for analysis. Particles with $Cy_5$ signals were identified by standard image analysis. As shown in FIG. 14, the bis-PNA clamps specifically hybridize to particles functionalized with 10-mers and 18-mers of polyadenine, whereas the bis-PNA clamps do not hybridize to unrelated nucleotide sequences (N-10 or N-18) in contrast, negative control arrays to capture no PNA. A computer program was used to automatically align the images from the chip. Fluorescent intensity at different wavelengths was extracted from the images and assigned to corresponding particles on the chip. The fluorescent intensity of the internal dyes of the stained beads was then clustered.

Example 5

Figure 15:
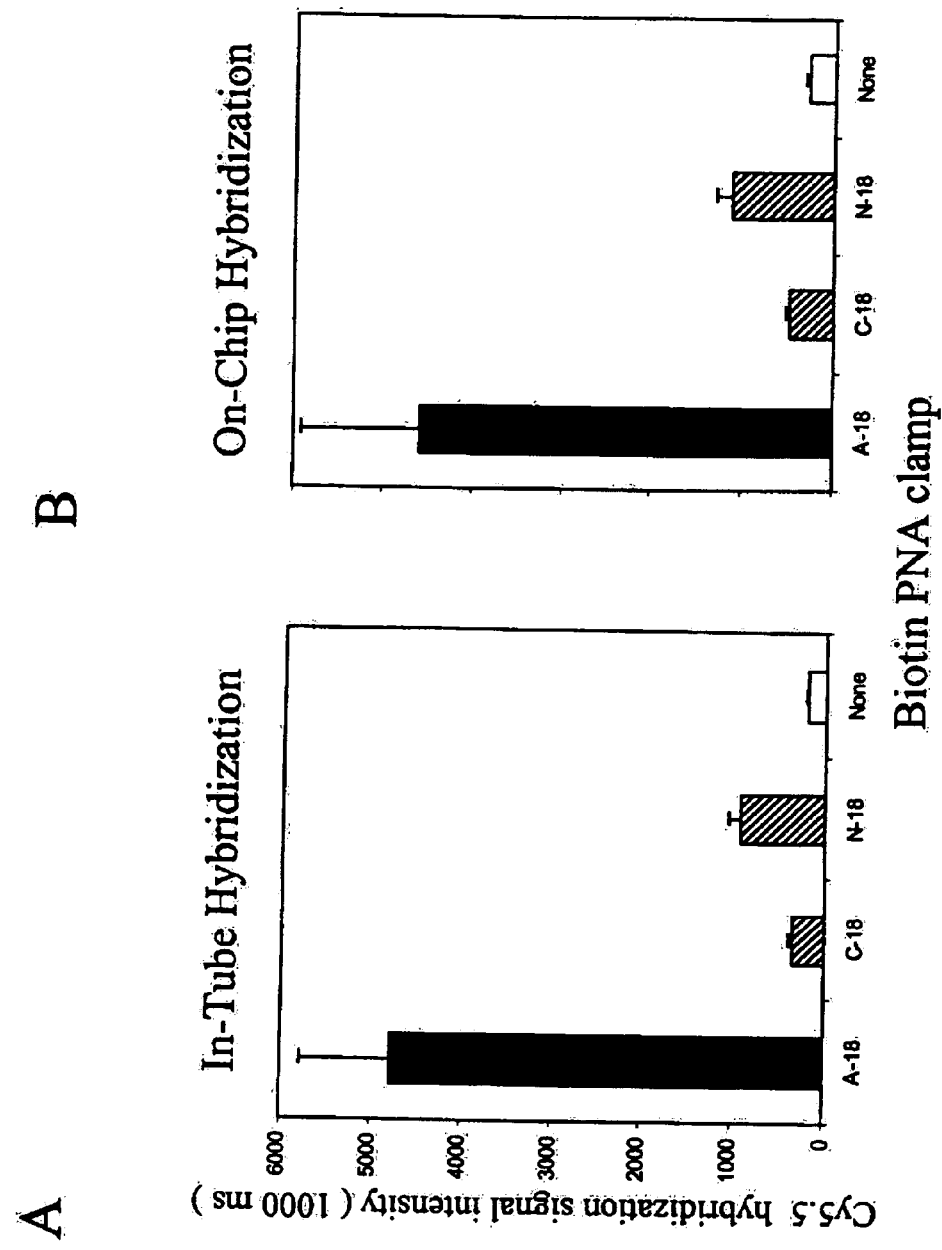
FIG. 15 shows the results of in-tube hybridization assays (A) compared to on-chip hybridization assays (B) for testing sequence-specific capturing of bis-PNA oligomers to DNA oligonucleotides immobilized on color-encoded microparticles.

In-Tube Hybridization of Bis-PNA Oligomers to DNA Oligonucleotides On Color-Encoded Microparticles In-tube hybridization assays were performed to ascertain sequence-specific capture of bis-PNA oligomers to DNA oligonucleotides on color-encoded microparticles. Briefly, the bis-PNA oligomer was a biotinylated PNA clamp with 12-13 thymine bases on each arm. Prior to hybridization, four types of biotinylated oligonucleotides were coupled to NeutrAvidin-functionalized microparticles, the respective oligonucleotides containing an 18-mer oligoadenine (A-18), an unrelated sequences of 18 nucleotides (N-18), a 10-mer polyadenine (A-10), and an unrelated unrelated sequence of nucleotides (N-10). Control microparticles contained no oligonucleotides on the surface. After coupling, all of the oligonucleotide-functionalized microparticles were combined into one tube. The oligonucleotide-functionalized microparticles were first pre-hybridized in a buffer containing 90 mM NaCl, 83 mM guanidine thiocyanate, 8 mM $MgCl_2$, 17 nM EDTA, 0.1% biotin, 0.1% Tween-20, 70 mM Tris-HCl, at pH 7.5, at 40° C. for 20 min. Next, the biotinylated bis-PNA was added into the pre-hybridization buffer to a final concentration of 200 nM. Hybridization was carried out in a humidified chamber at 40° C. for 1 hour. The negative control was assayed without PNA in the hybridization buffer. Upon completion of hybridization, particles were washed with 100 mM NaCl, 10 mM Tris-HCl, pH 7.5, 0.1% Tween-20, at room temperature for 10 min, followed by assembly of microparticle arrays on silicon chips. For detection of captured biotinylated PNAs, chips were incubated with Cy5.5-conjugated streptavidin (20 microgram/ml) in 100 mM NaCl, 100 mM sodium phosphate, pH 7.5, at room temperature for 30 min. After washing with 15 mM NaCl, 10 mM Tris-HCl, at pH 7.5, arrays were examined by using a fluorescence microscope. The identity of the particles was determined according to their respective color codes. Particles with Cy5.5 signal were identified by using computer program. As shown in FIG. 15A, the bis-PNA clamps specifically hybridized to particles functionalized with A-18, but not to C-18 and N-18. Specifically, the bis-PNA clamps specifically captured to A-18, produced a Cy5.5 signal of approximately 4750 arbitrary units at 1000 ms integration time at the Cy5.5 channel, while C-18 and N-18 functionalized particles produced a Cy5.5 signal of about 500 and 1000, respectively. Cy5.5 signal intensities produced by in-tube PNA hybridization (FIG. 15A) were comparable to those for on-chip hybridization (FIG. 15B) performed as in Example 4.

Example 6

Figure 16:
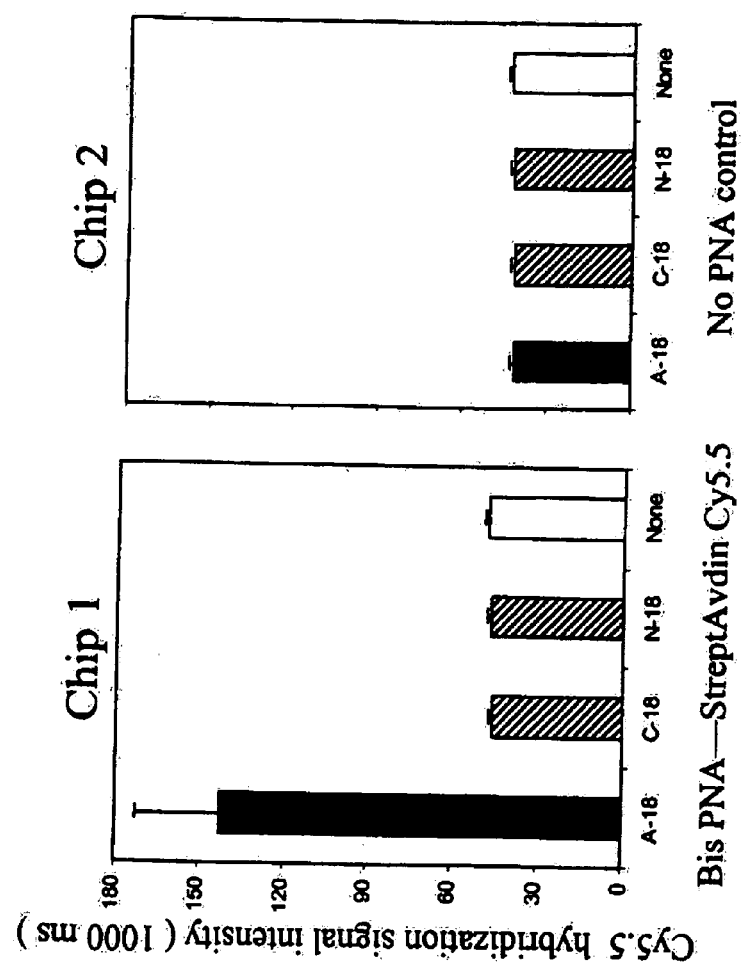
FIG. 16 shows the results of on-chip hybridization assays testing sequence-specific capturing of bis-PNA-protein chimerae to DNA oligonucleotides (18 bases in length) immobilized on microparticle arrays.

Hybridization of PNA-Protein Chimerae to DNA Oligonucleotides Displayed on Microparticle Arrays On-chip hybridization assays were performed to test sequence-specific capturing of bis-PNA-protein chimerae to DNA oligonucleotides immobilized on microparticle arrays. Briefly, the PNA protein chimera was a conjugate of Cy5.5-labeled streptavidin and biotinylated PNA clamp. The PNA clamp contains 12-13 thymine bases on each array. Comparable amounts of Cy5.5-labeled streptavidin and biotinylated PNA were used in conjugation which was carried out in PBS at room temperature for 30 min. Prior to hybridization, four types of biotinylated oligonucleotides were coupled to NeutrAvidin-functionalized microparticles, the respective oligonucleotides containing an 18-mer oligoadenine (A-18), an 18-mer of oligocytosine (C-18), and an unrelated sequence of 18 nucleotides (N-18). After coupling, all of the oligonucleotide-functionalized microparticles along with a negative control particle containing no oligonucleotide capture probe were combined into one tube for assembly of microparticle arrays on silicon chips. Chips were first pre-hybridized in a buffer containing 90 mM NaCl, 83 mM guanidine thiocynate, 8 mM $MgCl_2$, 17 nM EDTA, 0.1% biotin, 0.1% Tween-20, 70 mM Tris-HCl, pH 7.5, at 40° C. for 20 min. Then, the bis-PNA protein chimerae were added into the pre-hybridization buffer to a final concentration of 200 nM. Hybridization was carried out in a humidified chamber at 40° C. for 1 hour. The negative control chip received no PNA in the hybridization buffer. Upon completion of hybridization, chips were washed with 100 mM NaCl, 10 mM Tris-HCl, pH 7.5, 0.1% Tween-20, at room temperature for 10 min. The chips were examined by using a fluorescence microscope. Several images were taken from the same chip using different filters that pass through specific wavelengths. The identity of the particles was determined according to their respective color codes. Particles with Cy5.5 signal were identified by standard image analysis as described in Example 4. As shown in FIG. 16, the bis-PNA protein chimerae specifically hybridize to particles coupled with 18-mers of polyadenine on the chip (140 Cy5.5 signal intensity at 1000 ms integration), as compared to the no PNA control chip. In both instances, the C-18, N-18, and control (none; no oligonucleotides on the surface), only resulted in about 45 units of Cy5.5 signal intensity at 1000 ms integration).

Example 7

On-Chip Hybridization of Biotinylated PNA Oligomers to Oligonucleotides Immobilized to Magnetic Color-Encoded Microparticles On-chip hybridization of target molecules to oligonucleotides probes were immobilized on color-encoded magnetic particles. Specifically, biotinylated oligonucleotides with known nucleotide sequence (0.4 μM) were coupled to a defined type of color-encoded magnetic particles (approximately $6.7 \times 10^5$ particles) that were coated with NeutrAvidin on the surface. The coupling reaction was carried out in 0.1 ml coupling buffer (150 mM NaCl, 0.05 mM ethylenediamine tetra-acetic acid (EDTA), 0.5% bovine serum albumin, 0.5 mM Tris-HCl, and 100 mM sodium phosphate, pH 7.2) with vortexing at room temperature for 30 min. After coupling, the particles were collected using a magnet. Unreacted NeutrAvidin sites were blocked with 0.1% biotin in 150 mM NaCl and 100 mM sodium phosphate, at pH 7.2 with 0.05% Tween-20 at room temperature for 20 min with vortexing. After blocking, the particles were washed with 0.2 ml of 150 mM NaCl and 100 mM sodium phosphate, at pH 7.2 containing 0.05% Tween-20. This protocol was also applied to couple other biotinylated oligonucleotides to other types of NeutrAvidin-coated particles.

Figure 17:
FIG. 17 shows the results of PNA oligomers hybridized to complementary oligonucleotides immobilized on color-encoded magnetic particles, where Chip B (B) is the negative control for Chip A (A).

Several types of color-encoded oligonucleotide-functionalized microparticles, including magnetic particles and non-magnetic controls, were combined into one tube for the assembly of microparticle arrays according to methods known in the prior art. In this example, arrays were formed. 2.5×2.5 mm silicon chips containing an array template of 4,000 sites. On-chip hybridization of biotinylated peptide nucleic acid (PNA) oligomers on an array of microparticles-displayed complementary oligonucleotide capture probes was carried out in 30 microliters of hybridization buffer (90 mM NaCl, 83 mM guanidine thiocyanate, 8 mM $MgCl_2$, 17 nM EDTA, 0.02% biotin, 0.1% Tween-20, 70 mM Tris-HCl, pH 7.5) containing biotinylated PNA oligomers at a concentration of 200 nM. Hybridization was performed on a rotating shaker at 40° C. for 60 min. Upon completion of hybridization, the array was washed with 50 microliters of 250 mM NaCl, 10 mM Tris-HCl, at pH 7.5, 0.1% Tween-20, at room temperature for 10 min. Captured biotinylated PNA oligomers were visualized by incubation of the microparticle array with Cy5.5-conjugated Streptavidin (18 micrograms/ml) in 150 mM NaCl and 100 mM sodium phosphate, pH 7.2, at room temperature for 30 min. After washing with 15 mM NaCl, 10 mM Tris-HCl, at pH7.5, arrays were examined under a fluorescence microscope. Fluorescence emitted from the color-encoded microparticles and the Cy5.5-labeled PNA oligomers was determined by using optical filters with specific wavelengths. The magnetic and non-magnetic particles were decoded according to their color codes. Particles with Cy5 signals were identified by standard image analysis as described in Example 4. Assay results illustrated in FIG. 17 showed that PNAs specifically hybridize to complementary oligonucleotides displayed on color-encoded magnetic and non-magnetic particles. More specifically, Cy5.5 signal intensity was determined from four types of color-encoded microparticles (I, II, III, and IV) from two microparticle arrays (Chip A and B, for panels A and B, respectively) in the on-chip hybridization assay. The type I particles are color-encoded magnetic particles, whereas types II, III, and IV are three different types of color-encoded particles that are not magnetic. Type I and II particles were immobilized with biotinylated oligonucleotides that are complementary to the PNA oligomers. Type III particles were coupled with oligonucleotides with unrelated base sequence to the PNA. Type IV particles had no oligonucleotides on the surface. Chip B served as a negative control for Chip A, which was incubated with hybridization mix without the PNA. "n" indicates the number of the particles on the chips. Particles of type I and type II produced respective signal intensities of about 2250 and 1500, whereas particles of type III and type IV did not produce significant fluorescence, about 400 and 250 Cy5.5 signal intensity. The bars represent standard deviation of means.

Example 8

Figure 18:
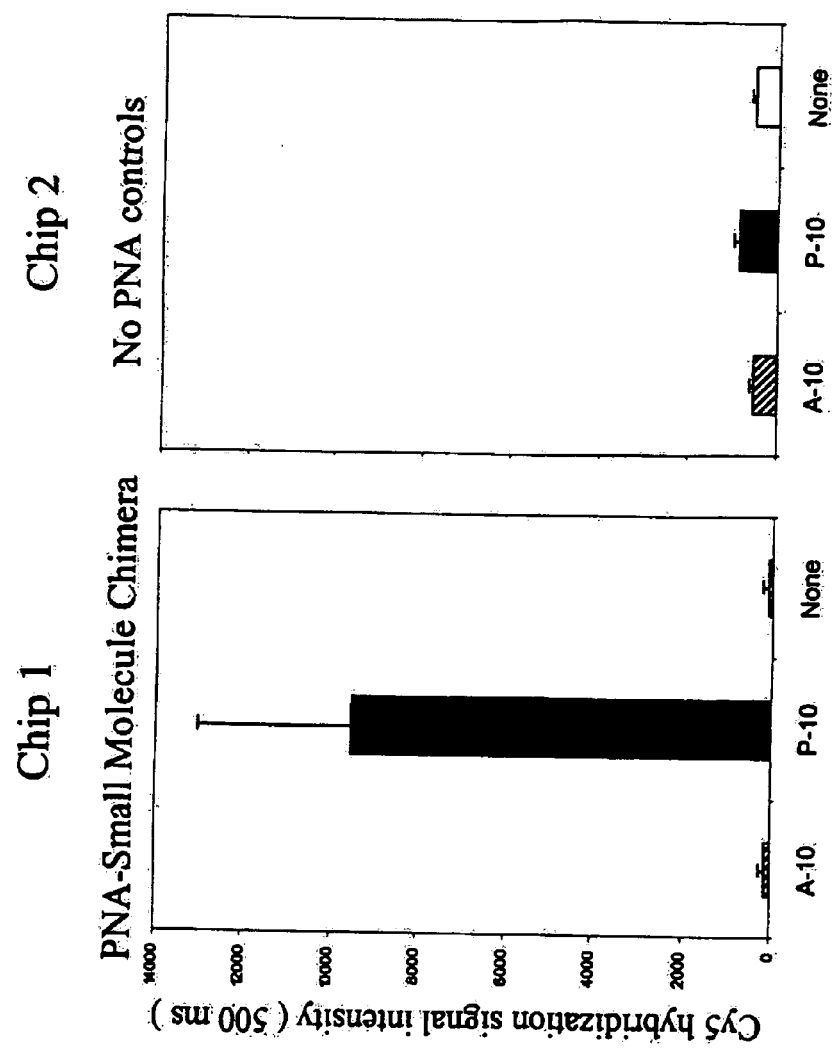
FIG. 18 shows the results of on-chip hybridization assays for testing sequence-specific capturing of bis-PNA-small molecule chimerae to DNA oligonucleotides (10 bases in length) immobilized on microparticle arrays, where Chip 2 is the negative control for Chip 1.

On-Chip Hybridization of PNA-Small Molecule Chimerae to Oligonucleotides on Microparticle Arrays On-chip hybridization assays were performed in order to ascertain the sequence-specific capture of bis-PNA-small molecule chimerae to DNA oligonucleotides displayed on color-encoded microparticle arrays. Briefly, the bis-PNA-small molecule chimera was a conjugate of bis-PNA containing ten (10) bases in defined sequence on each arm and a Cy5 dye, previously described in connection with FIG. 13 and Example 3. Prior to hybridization, four types of biotinylated oligonucleotides were coupled to NeutrAvidin-functionalized microparticles, as previously described in Example 1. The respective oligonucleotides containing the following sequences: a 10-mer of polyadenine (A-10) and 10-mers, each complementary to one of the arms of the bis-PNA oligomers (P-10). Also included were control microparticles displaying no oligonucleotide capture probes. After coupling, all of the oligonucleotide-functionalized microparticles along with a negative control particle containing no oligonucleotide capture probe were combined into one tube for assembly of microparticle arrays on silicon chips. Chips were first pre-hybridized in a buffer containing 90 mM NaCl, 83 mM guanidine thiocyanate, 8 mM $MgCl_2$, 17 nM EDTA, 0.1% biotin, 0.1% Tween-20, 70 mM Tris-HCl, at pH 7.5, at 40° C. for 20 min. Bis-PNA-Cy5 conjugate was added into the pre-hybridization buffer to a the final concentration of approximately 200 nM. Hybridization was carried out in a humidified chamber at 40° C. for 1 hour. The negative control chip was placed into a hybridization buffer containing no PNA chimerae. Upon completion of hybridization, chips were washed with 15 mM NaCl, 10 mM Tris-HCl, at pH 7.5 followed by examination under a fluorescence microscope. The identity of the particles was determined according to their respective color codes. Particles with Cy5 signal were identified from the beads by standard image analysis as described in Example 4. Assay results for chips in FIG. 18 show that bis-PNA-small molecule chimerae specifically hybridized to particles functionalized with complementary P-10 capture probes but not to A-10 particles and control particles, produced hybridization signals (recorded at 500 ms integration time) whereas none of the particle on chips produced a significant signal. Error bars represent the standard deviations of means.

Example 9

Figure 19:
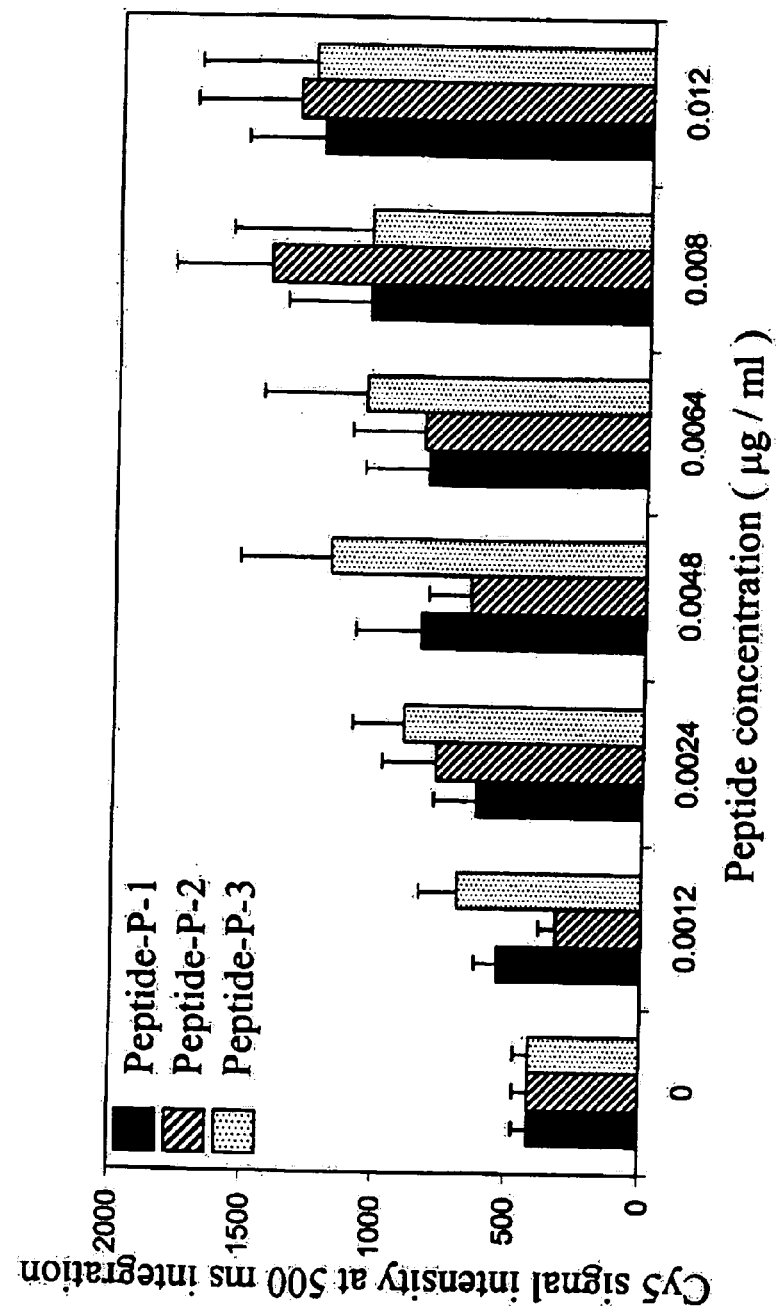
FIG. 19 shows the results of three biotinylated phosphorylated peptide standard curves (Peptide-P-1, Peptide-P-2, and Peptide-P-3) at increasing concentrations, where the peptides are coupled to specific color-encoded beads coated with NeutrAvidin using one microparticle array.

Simultaneous Generation of Standard Curves for Three Phosphorylated Peptides on Microparticle Arrays Three different biotinylated phosphorylated peptides (Peptide-P-1, P-2, and P-3. Peptide-P-1: Biotin-CK-VEKIGEGT[pY]GVVYK (SEQ ID NO: 1), where the tyrosine at amino acid 11 is phosphorylated, is derived from human tyrosine kinase substrate p34cdc2 (Cheng, et al. *J. Biol. Chem.* 267:9248-9256, 1992). Peptide-P-2: Biotin-CEGPWLEEEEA[pY]GWMDFK-Biotin (SEQ ID NO: 2), phosphorylated on the tyrosine at position 13, is human Gastrin-17 (Baldwin et al, *Nature*, 301, 435-437, 1983). Peptide-P-3: Biotin-CRRLIEDAE[pY]AARGK, phosphorylated on the tyrosine at amino acid 10, is derived from the tyrosine phosphorylation site in $p60^{src}$ from the Rous sarcoma virus transforming protein (SEQ ID NO: 3) (Casnelli et al, *PNAS* 79:282-286, 1982). Peptide-P-1, Peptide-P-2, and Peptide-P-3, in defined concentration 0, 0.0012, 0.0024, 0.0048, 0.0064, 0.008, and 0.012 pg/ml, were coupled to color-encoded microparticles that had been functionalized with NeutrAvidin according to as those described in Example 1. All of the peptide-functionalized microparticles were then combined for assembly into microparticle array according to known methods such as those described in Example 1. The assembled microparticle array was incubated with monoclonal antibodies specific for the phosphorylation modification on all of the peptides. For the purpose of signal amplification, the chip was incubated with fluorescent dye-labeled secondary antibodies specific for the primary monoclonal antibodies bound on the arrays. After washing with PBST, the array was examined by using a fluorescence microscope according to known prior art methods, such as the READ assays. By using this method, three phosphorylated peptide standard curves were generated by using one microparticle array (FIG. 19). As the peptide concentration increased, the Cy5 fluorescent signal intensity at 500 ms integration time generally increased for all three phosphorylated peptides as well, ranging from about 400 to about 1400 units of Cy5 signal intensity at 500 times integration. The error bars shown in FIG. 19 represent standard deviation of the means.

Example 10

Generation of Phosphorylated Peptide Standard Curve on Microparticle Arrays

Figure 20:
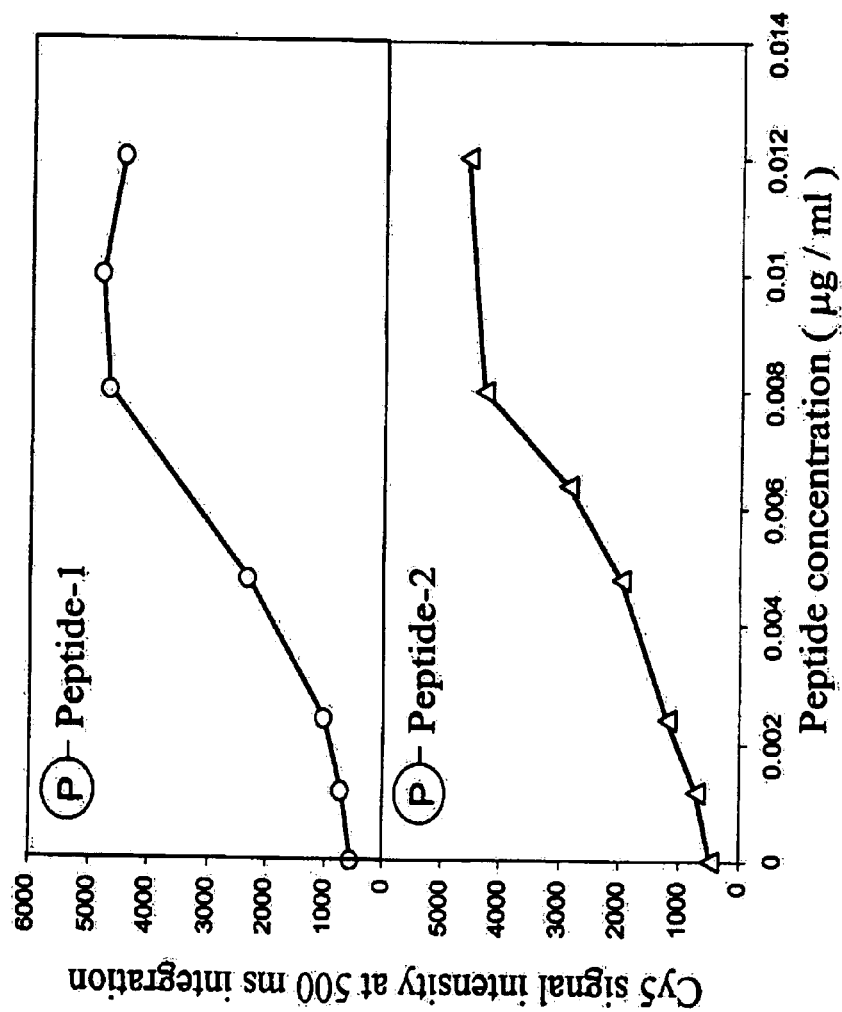
FIG. 20 shows the results of two biotinlyated phosphorylated peptide standard curves (Peptide-P-1 and Peptide-P-2) at increasing concentrations, where the peptides are coupled to specific color-encoded beads coated with NeutrAvidin.

Each type of biotinylated phosphorylated peptides (Peptide-P-1 and P-2) as described in Example 9 in defined concentration 0, 0.002, 0.004, 0.008, 0.01, and 0.12 µg/ml was coupled to defined types of color-encoded beads that had been coated with NeutrAvidin on the surface according to known prior art methods, e.g. procedures described in Example 1. Unreacted sites on the surface of the particles were blocked according to known prior art methods. The functionalized beads with the same type of phosphorylated peptides were then combined in the test tube for assembly into microparticle array according to known prior art methods, such as LEAPS and direct disposition assembly method previously described in Provisional Application Ser. No. 60/343,621, filed Dec. 28, 2001 and U.S. application Ser. No. 10/192,352 filed Jul. 9, 2002. The assembled microparticle arrays were incubated with monoclonal antibodies specific for the phosphorylation modification on all of the peptides. For the purpose of signal amplification, the primary monoclonal antibodies were further bound by using specific secondary antibodies and fluorescent (Cy5)-labeled third antibodies. After washing with PBST, the arrays were examined by using a fluorescent microscope according to known prior art methods, such as the READ assays. By using this method, standard curves for the phosphorylated peptides were generated by using microparticle arrays (FIG. 20). For P-Peptide-1, the Cy5 signal intensity at 500 ms integration increased from about 500 to about 5000 units, peaking at a concentration of 0.008 µg/ml. Similarly, for Peptide-P-2, the Cy5 signal intensity at 500 ms integration increased from about 500 to about 4500 units, also peaking at a concentration of 0.008 µg/ml. The error bars shown in FIG. 20 represent standard deviation of the means.

Example 11

Immunodetection of Phosphorylated Peptides by using Peroxidase-Conjugated Antibodies on Microparticle Arrays Each type of biotinylated phosphorylated peptides or biotinylated non-phosphorylated peptides was coupled to defined color-encoded beads that had been coated with NeutrAvidin on the surface according to known prior art methods, e.g. procedures described in Example 1. Density of the peptides on the surface of the carriers reaches maximum as described in Example 1. After coupling, the particles were washed by using phosphate-buffered saline (PBS; 0.1 M sodium phosphate, 0.15 M sodium chloride, pH 7.2) with the addition of 0.05% Tween-20 (PBST). Then, all of the peptide-functionalized beads were combined into a test tube for assembly of a microparticle array according to known prior art methods, such as Light-controlled Electrokinetic Assembly of Particles near Surfaces (LEAPS), and direct disposition assembly method previously described in Provisional Application Ser. No. 60/343,621, filed Dec. 28, 2001 and U.S. application Ser. No. 10/192,352 filed Jul. 9, 2002. The assembled microparticle array was blocked by using 1% bovine serum albumin (BSA) in PBST. For immunodetection of phosphorylated peptides on the arrays, the chip was incubated with peroxidase-conjugated monoclonal antibodies specific for the phosphorylation modification. The incubation was carried out in a humid chamber for binding of the antibodies to the phosphorylated peptides. The antibody-bound microparticle array was washed by using PBST followed by detection using peroxidase substrates according to known prior art methods, such as using the tyramide reagents from Molecular Probes (e.g. Catalog #T-20912, T-20916, etc).

Figure 21:
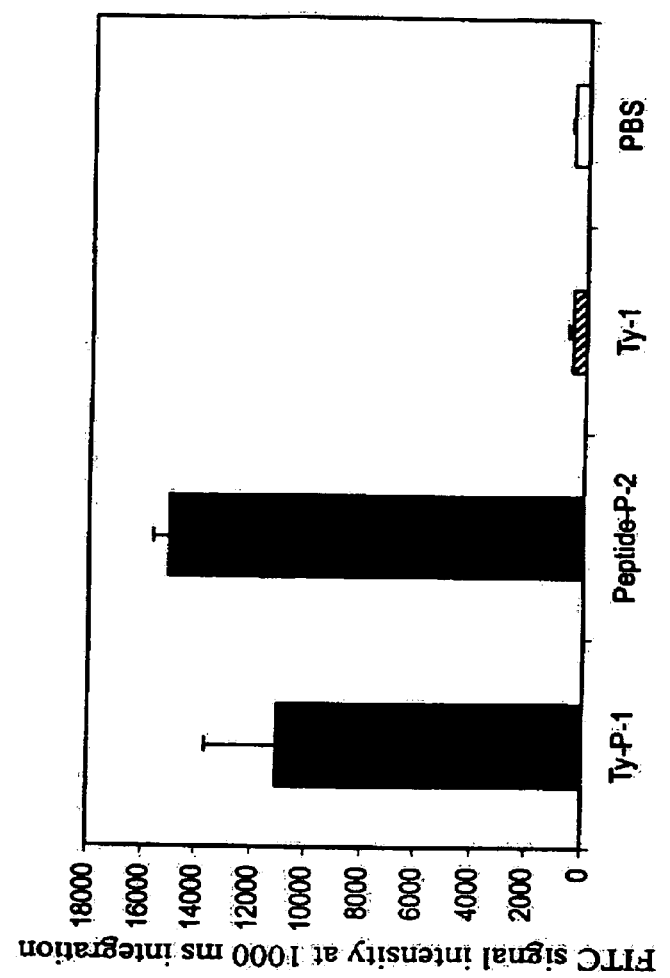
FIG. 21 shows the results of immunodetection of phosphorylated peptides (Ty-P-1 and Peptide-P-2) using tyramide reagents on microparticle array The monoclonal antibody used in the assay is labeled with peroxidase specific for phosphorylated modification.

Results for immunodetection of phosphorylated peptides by using tyramide reagents are shown in FIG. 21. Briefly, each of four types of color-encoded microparticles was coupled with one of two types of phosphorylated peptides (Ty-P-1 or Peptide-P-2), one type of non-phosphorylated peptide (Ty-1), or none, peptide control (PBS) where Ty-1 is Biotin-KVEKIGEGTYGVVYK (SEQ ID NO: 4), Ty-P-1 is Ty-1, but has a phosphorylated tyrosine at amino acid 10 (Biotin-KVEKIGEGT[pY]GVVYK), and Peptide-P-2: Biotin-CEGPWLEEEEEA[pY]GWMDFK (SEQ ID NO: 2) is phosphorylated on the tyrosine at position 14. The peptide-functionalized microparticles were assembled into particle array for immunodetection using alkaline-phosphatase-conjugated monoclonal antibody specific for the modification. The bound antibodies were detected by using the tyramide reagents. The fluorescent signal from the beads were detected by using a fluorescent microscope according to known prior art methods, such as the Random Encoded Array Detection (READ) assay. Briefly, fluorescence emitted from the color-encoded microparticles and the analytes were determined by using specific optical filters. The identity of the particles was decoded according to their unique color codes. Particles with positive assay signal were identified by standard image analysis as described in Example 4. The fluorescent product, fluorescein isothiocynate (FITC) generated from the akaline-phosphtase-catalyzed chemical reaction was precipitated on the beads with bound antibodies. FIG. 21 shows higher FITC signal intensity in phosphorylated peptides, 11,000 units at 1000 ms integration for Ty-P-1 and 15,000 units at 1000 ms integration for Peptide-P-2, and significantly lower signal for non-phosphorylated Ty-1 or control, approximately 700 units at 1000 ms integration. The error bars shown in FIG. 21 represent standard deviation of the means.

Example 12

Detection of Phosphorylated Peptides using Fluorescent Dye-Labeled Antibodies on Microparticle Arrays Each type of biotinylated phosphorylated peptides or biotinylated non-phosphorylated peptides was coupled to defined color-encoded beads that had been coated with NeutrAvidin on the surface according to known prior art methods, such as that described in Example 1. Density of the peptides on the surface of the carriers reached maximum as described in Example 1. After coupling, the particles were washed by using PBST. Then, all of the peptide-functionalized beads were combined into a test tube for assembly of microparticle array according to known prior art methods, such as LEAPS, and direct disposition assembly method previously described in Provisional Application Ser. No. 60/343,621, filed Dec. 28, 2001 and U.S. application Ser. No.10/192,352 filed Jul. 9, 2002. The assembled microparticle array is blocked by using 1% BSA in PBST. For immunodetection of phosphorylated peptides on the array, the chip is incubated with monoclonal antibodies specific for the phosphorylation modification. The incubation is carried out in a humid chamber for binding of the antibodies to the phosphorylated peptides. The unbound antibodies are washed away by using PBST. For the purpose of signal amplification, the chip is incubated with secondary antibodies specific for the primary monoclonal antibodies bound on the arrays. The signal may be further amplified by incubation of the chips with fluorescent-labeled antibodies specific for the secondary antibodies. After washing with PBST, the array is examined by using a fluorescent microscope according to known prior art methods, such as the READ assays.

Figure 22:
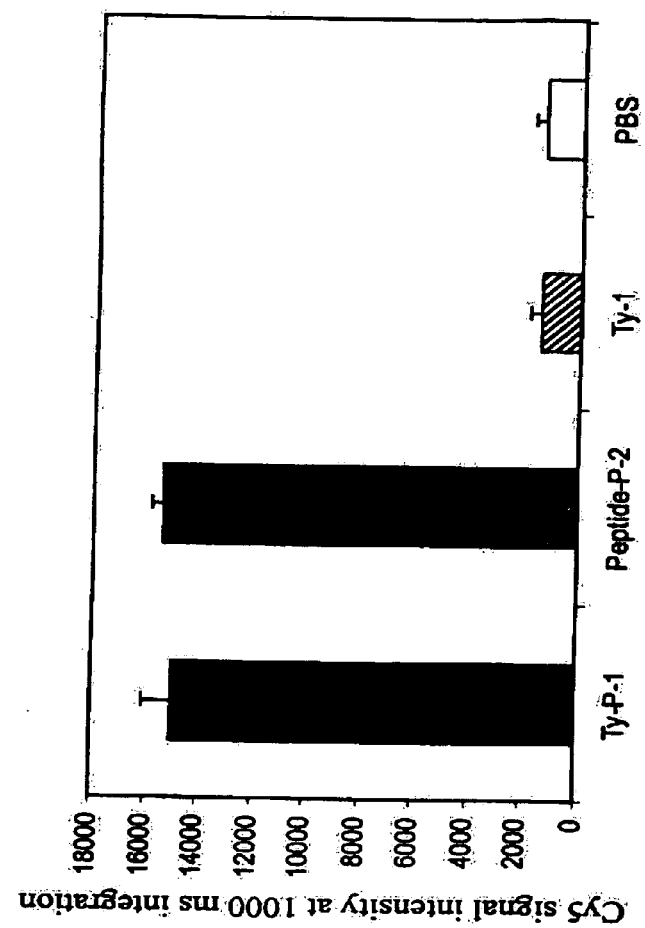
FIG. 22 shows the results of immunodetection of phosphorylated peptides (Ty-P-1 and Peptide-P-2) using phosphorylated peptide-specific monoclonal antibody on microparticle array. The bound monoclonal antibody is detected by using Cy-5 labeled secondary antibody.

Results for immunodetection of phosphorylated peptides by using fluorescent-labeled antibodies on microparticle arrays are shown in FIG. 22. Briefly, each of four types of color-encoded microparticles is coupled with one of two types of phosphorylated peptides (Ty-P-1 or Peptide-P-2), one type of non-phosphorylated peptides (Ty-1) as described in Example 11. or none, peptide control (PBS). The peptide-functionalized microparticles are assembled into a particle array. The chip was incubated with phosphorylated peptide-specific monoclonal mouse IgG antibodies followed by incubation with mouse IgG-specific secondary antibodies, and then Cy5-labeled third antibodies for detection using a fluorescent microscope. Fluorescence was detected by Cy5 signals. FIG. 22 shows higher Cy5 signal intensity in phosphorylated peptides, 15,000 units at 1000 ms integration for Ty-P-1 and 15,500 units at 1000 ms integration for Peptide-P-2, and significantly lower signal for non-phosphorylated Ty-1 or control, approximately 1400 units at 1000 ms integration. The error bars in FIG. 22 represent standard deviation of the respective mean intensities.

Example 13

Detection of Multiple Phosphorylated Peptides using Fluorescent Dye-Labeled Antibodies on Microparticle Arrays Each type of biotinylated phosphorylated peptides or biotinylated non-phosphorylated peptides was coupled to defined color-encoded beads that had been coated with NeutrAvidin on the surface according to known prior arts, e.g. procedures described in Example 1. Density of the peptides on the surface of the carriers reached maximum as described in Example 1. After coupling, the particles were washed by using PBST. Then, all of the peptide-functionalized beads were combined into a test tube for assembly of a microparticle array according to known prior art methods, such as LEAPS, and direct disposition assembly method previously described in Provisional Application Ser. No. 60/343,621, filed Dec. 28, 2001 and U.S. application Ser. No. 10/192,352 filed Jul. 9, 2002. The assembled microparticle array was blocked by using 1% BSA in PBST. For immunodetection of phosphorylated peptides on the array, the chip was incubated with monoclonal antibodies specific for the phosphorylation modification. The incubation was carried out in a humid chamber for binding of the antibodies to the phosphorylated peptides. The unbound antibodies were washed away by using PBST. For the purpose of signal amplification, the chip was incubated with secondary antibodies specific for the primary monoclonal antibodies bound on the arrays. The signal may be further amplified by incubation of the chips with fluorescent-labeled antibodies specific for the secondary antibodies. After washing with PBST, the array was examined by using a fluorescent microscope according to known prior art methods, such as the READ assays.

Figure 23:
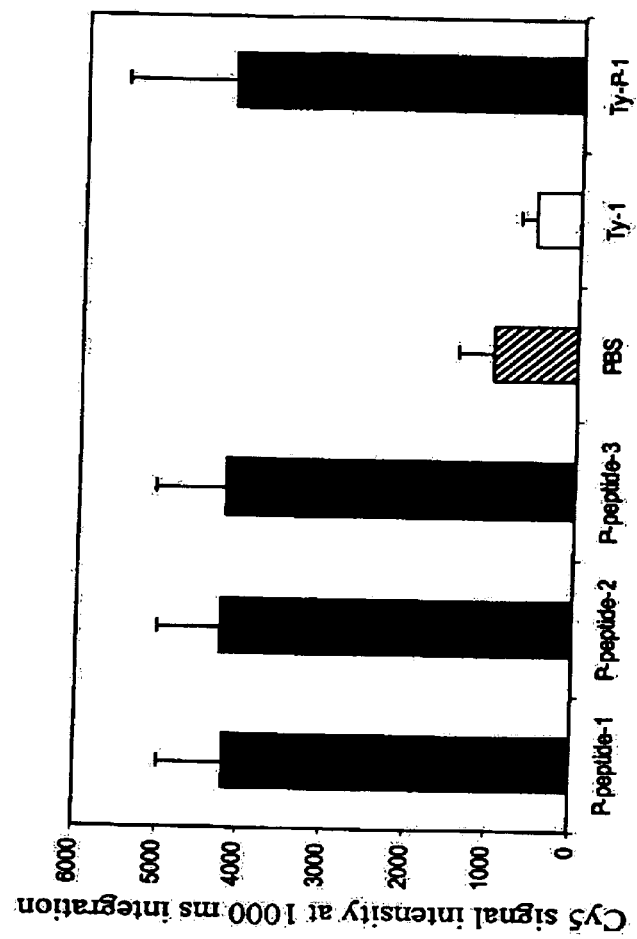
FIG. 23 shows the results of simultaneous immunodetection of multiple phosphorylated peptides using fluorescent-labeled antibodies on microparticle arrays.

Results for immunodetection of multiple phosphorylated peptides by using fluorescent-labeled antibodies on microparticle arrays are shown in FIG. 23. Briefly, each of six types of color-encoded microparticles was coupled with one of four types of phosphorylated peptides (Peptide-P-1, Peptide-P-2, Peptide-P-3, or Ty-P-1), one type of non-phosphorylated peptides (Ty-1) as described in Examples 9 and 11., or no peptide control (PBS). The peptide-functionalized microparticles were assembled into the particle array. The chip was incubated with phosphorylated peptide-specific monoclonal mouse IgG antibodies followed by incubation with mouse IgG-specific secondary antibodies, and then Cy5-labeled third antibodies for detection using a fluorescent microscope. Fluorescence was detected by Cy5 signals. FIG. 23 shows higher Cy5 signal intensity in phosphorylated peptides, approximately 14,000 units at 1000 ms integration for Peptide-P-1, Peptide-P-2, Peptide-P-3, and Ty-P-1, and significantly lower signal for non-phosphorylated Ty-1 or control, approximately 1000 units and 500 units at 1000 ms integration, respectively. The error bars shown in FIG. 23 represent standard deviation of the means.

Example 14

Ratio Quantification of Dual-Labeled Analytes

Figure 24A:
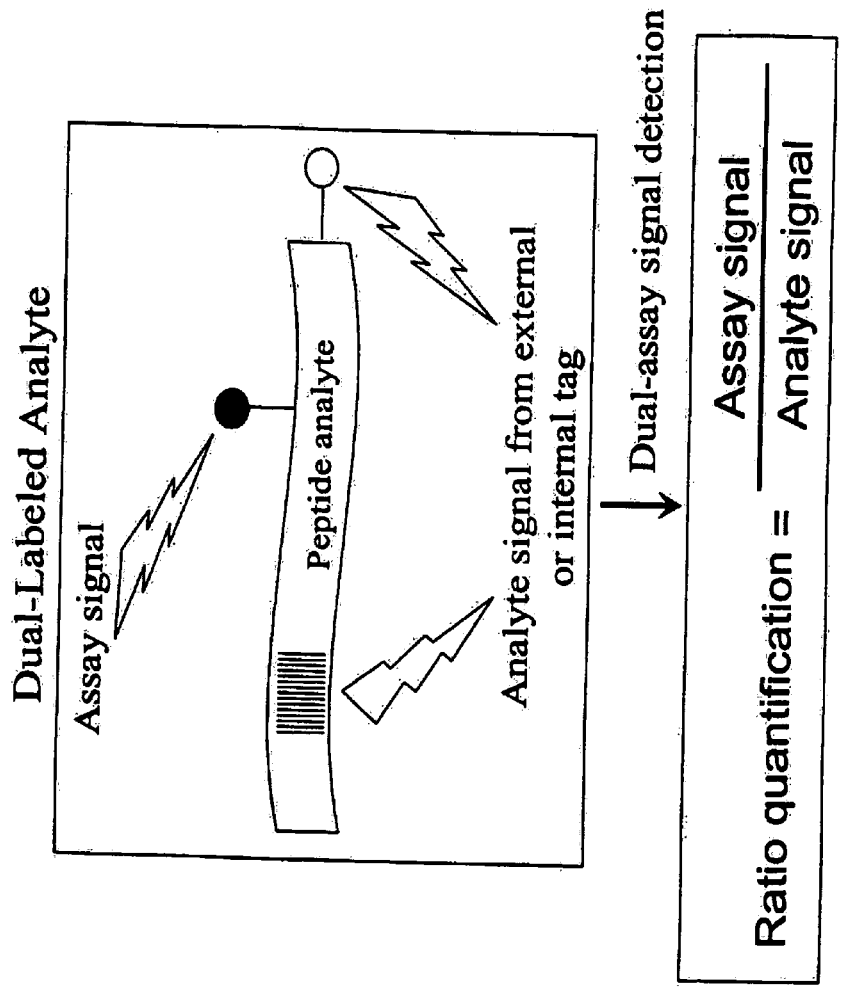
FIG. 24 shows the general design of a dual-labeled PNA-analyte chimera and ratio quantification of dual-assay signal detection (A); a specific PNA-peptide chimera labeled with a fluorescent dye and an internal His6 tag for determining the ratio quantification of Caspase 3 activity (B); and the results of Caspase 3 activity as determined by ratio quantification (C).

An analyte may be labeled with two fluorescent dyes. One of the fluorescent dyes labeled the analyte internally or externally according to known prior art methods, whereas the other dye was incorporated into the analyte in biochemical reactions of interest. Fluorescence from the analyte (analyte signal) and fluorescence from the assay may be determined by using a fluorescent microscope according to known prior art methods, such as READ assay. The assay signal related to the reaction efficiency may be evaluated by ratio quantification, that is, the ratio of the assay signal over the analyte signal in the assay. A general design for ratio quantification of dual-labeled analytes is illustrated in FIG. 24A.

Figure 24B:
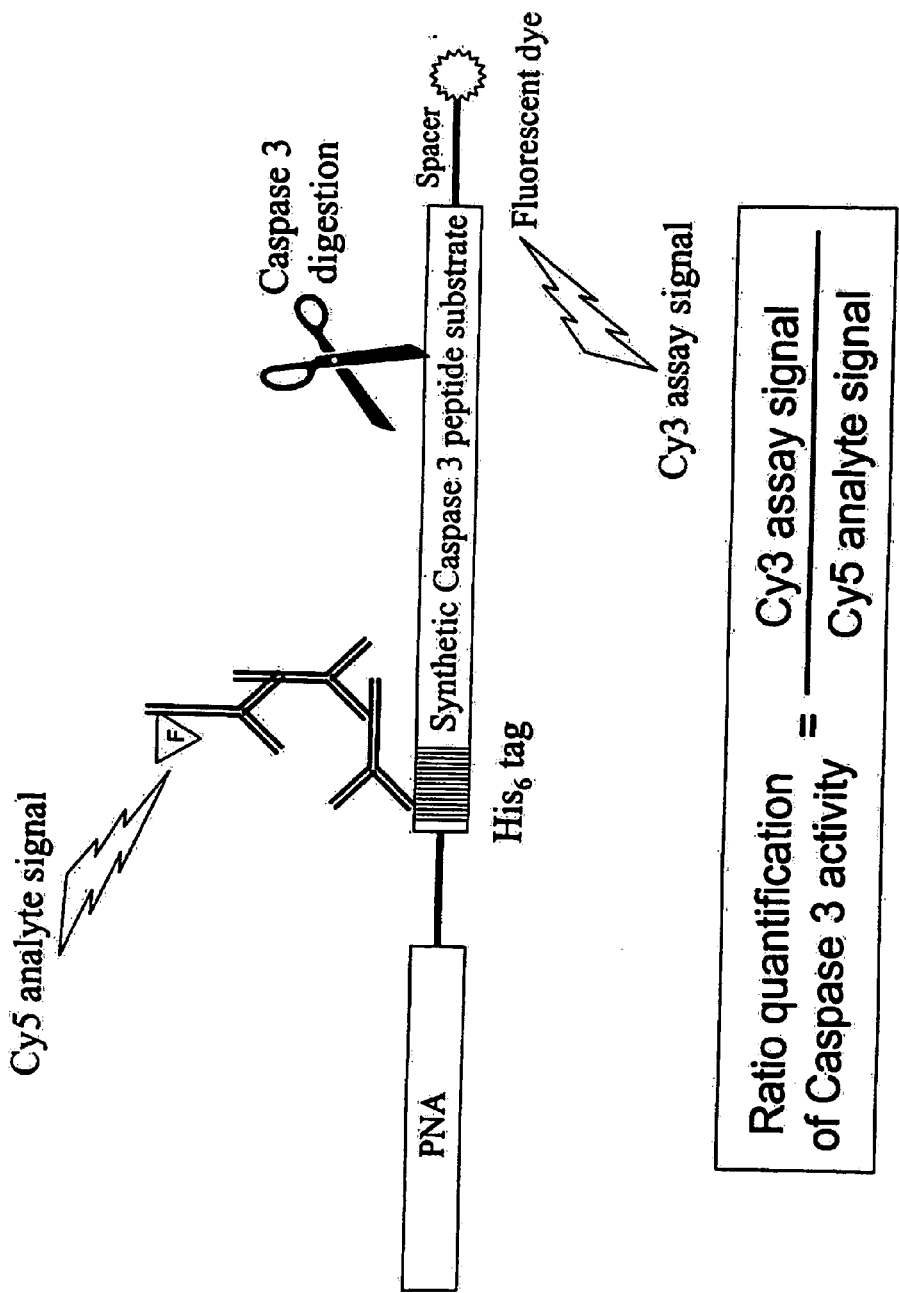

A specific design of dual-labeled PNA-peptide chimera is shown in FIG. 24B. The PNA-peptide chimera contained a PNA anchoring domain and a functional domain of synthetic peptide. The synthetic peptide contained a Caspase 3 cleavage site flanked by a fluorescent dye (Cy3) at the C-terminus and a polyhistidine (His6) at the N-terminus. The PNA-Caspase 3 dual-labeled peptide chimera is as follows: PNA-Linker-Cys (for conjugation) His His His His His His Asp Glu Val Asp Ala Lys-($C_{18}$-spacer)-Cy3 (SEQ ID NO: 5).

Figure 24C:
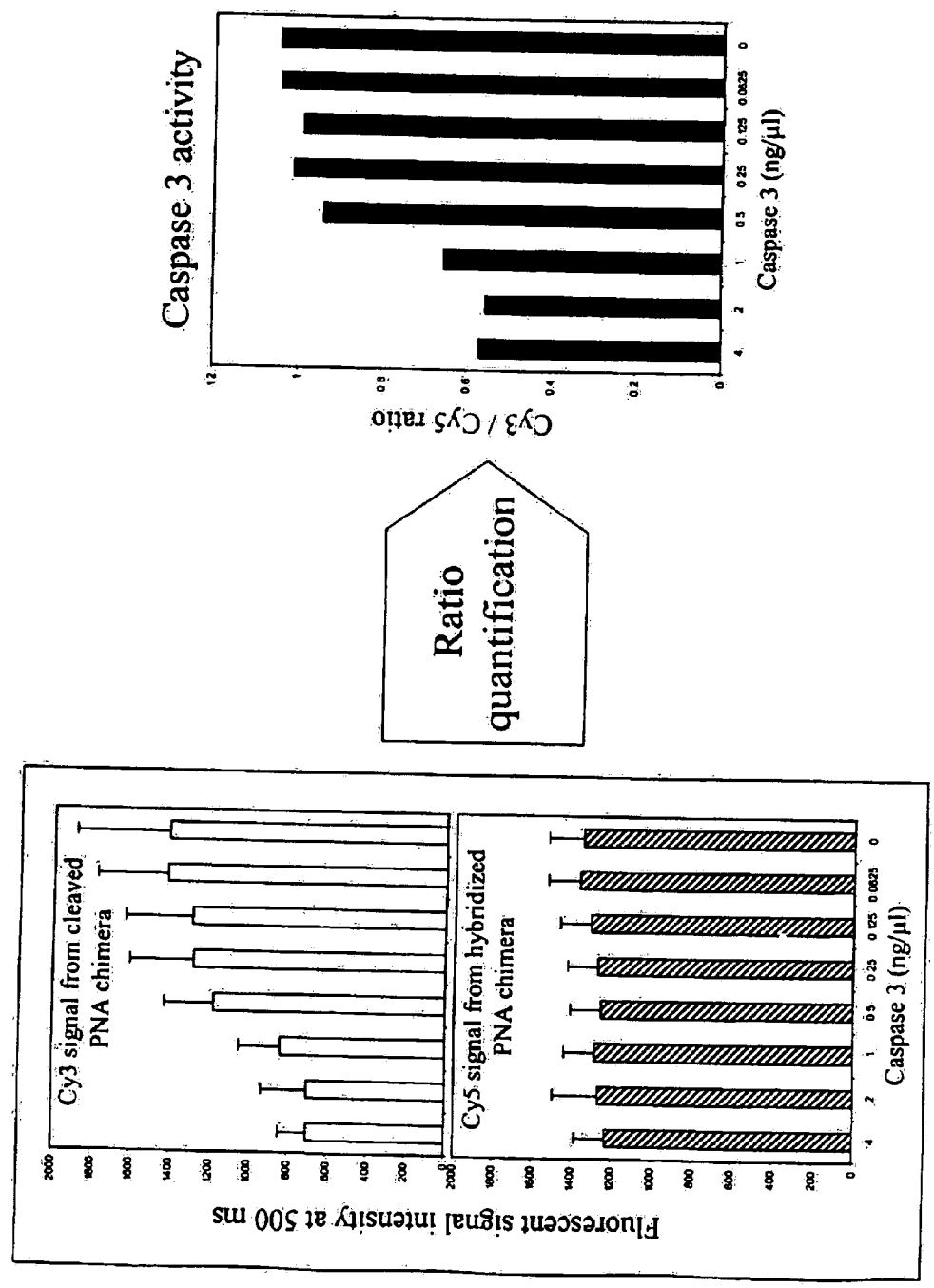

Caspase 3 digestion (by cutting at the 3' location on the aspartic acid residue) of the chimera results in cleavage of the Cy3 fluorescent dye. After digestion, the chimerea were captured to the surface of defined color-encoded microparticles via sequence-specific DNA/PNA hybridization. The microparticles with captured PNA-peptide chimerae were assembled into microparticle array. The His6 tag on the chimerae was detected by using His6-specific monoclonal antibodies on the chip. The primary monoclonal antibodies were further bound by using specific secondary antibodies and fluorescent (Cy5)-labeled third antibodies. Cy3 fluorescent intensity from the microparticle arrays was related to the portion of the uncut chimerae, whereas intensity of the Cy5 labels corresponded to the total amount of chimerae captured on the microparticle arrays. Thus, the relative Caspase 3 activity was quantified by determining the ratio of the Cy3 and Cy5 ratio in the assay (FIG. 24C). The results determined by ratio quantification show that as Caspase 3 increases in concentration (0, 0.0625, 0.125, 0.5, 1, 2, and 4 ng/µl), the fluorescent Cy3/Cy5 signal ratio decreases from approximately 1 to 0.6. The error bars shown in FIG. 24C represent standard deviation of the means.

Example 15

Figure 25A:
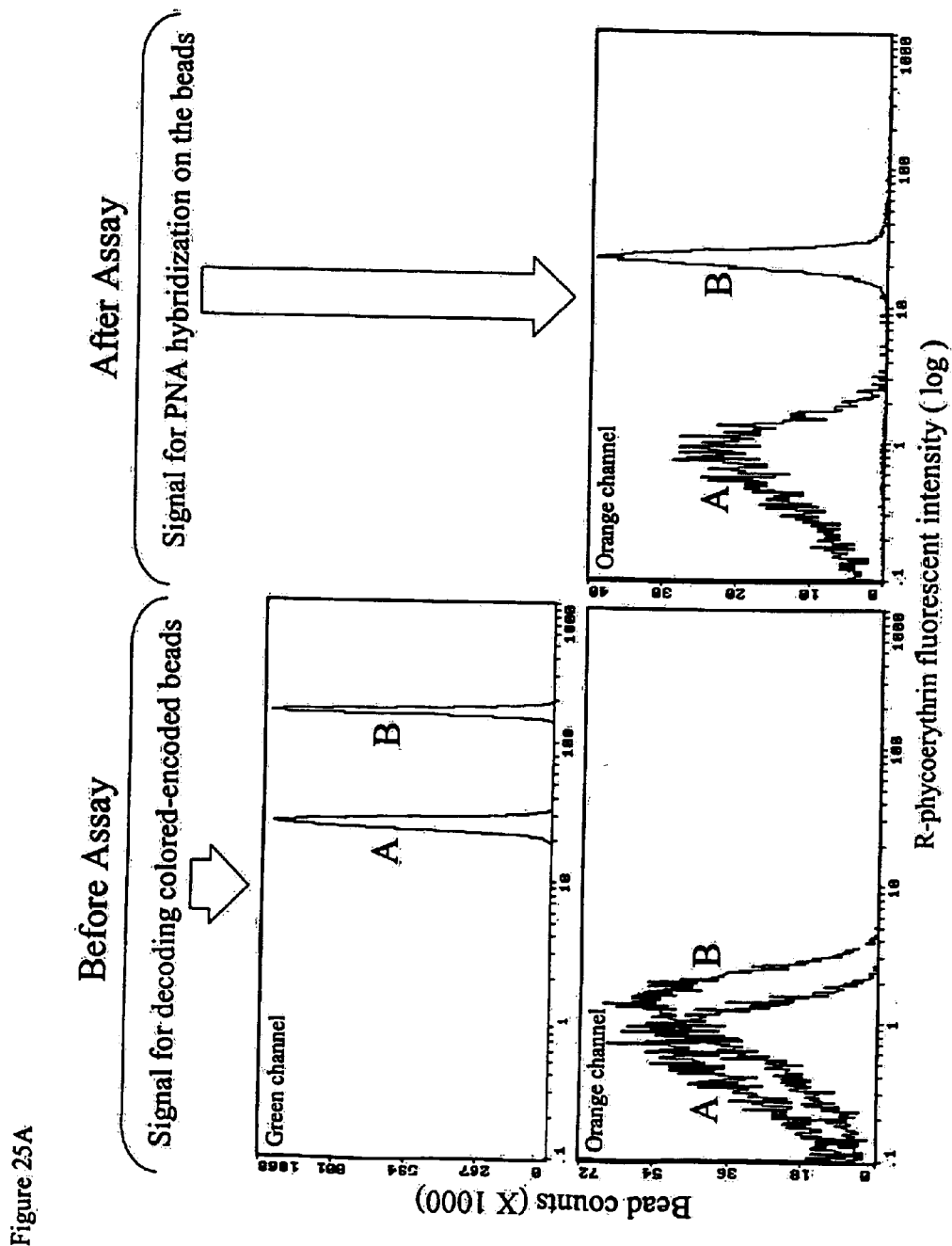
In FIG. 25A, two green beads (Green A and Green B) are coupled with two types of oligonucleotides (A) and (B). The PNA chimerae specifically binds to oligonucleotides on the Green B beads, which are detectable on the orange channel. Similarly, in FIG. 25B, the results show that PPNA chimera sequence specifically binds to one type of beads detected using flow cytometry.
Figure 25B:
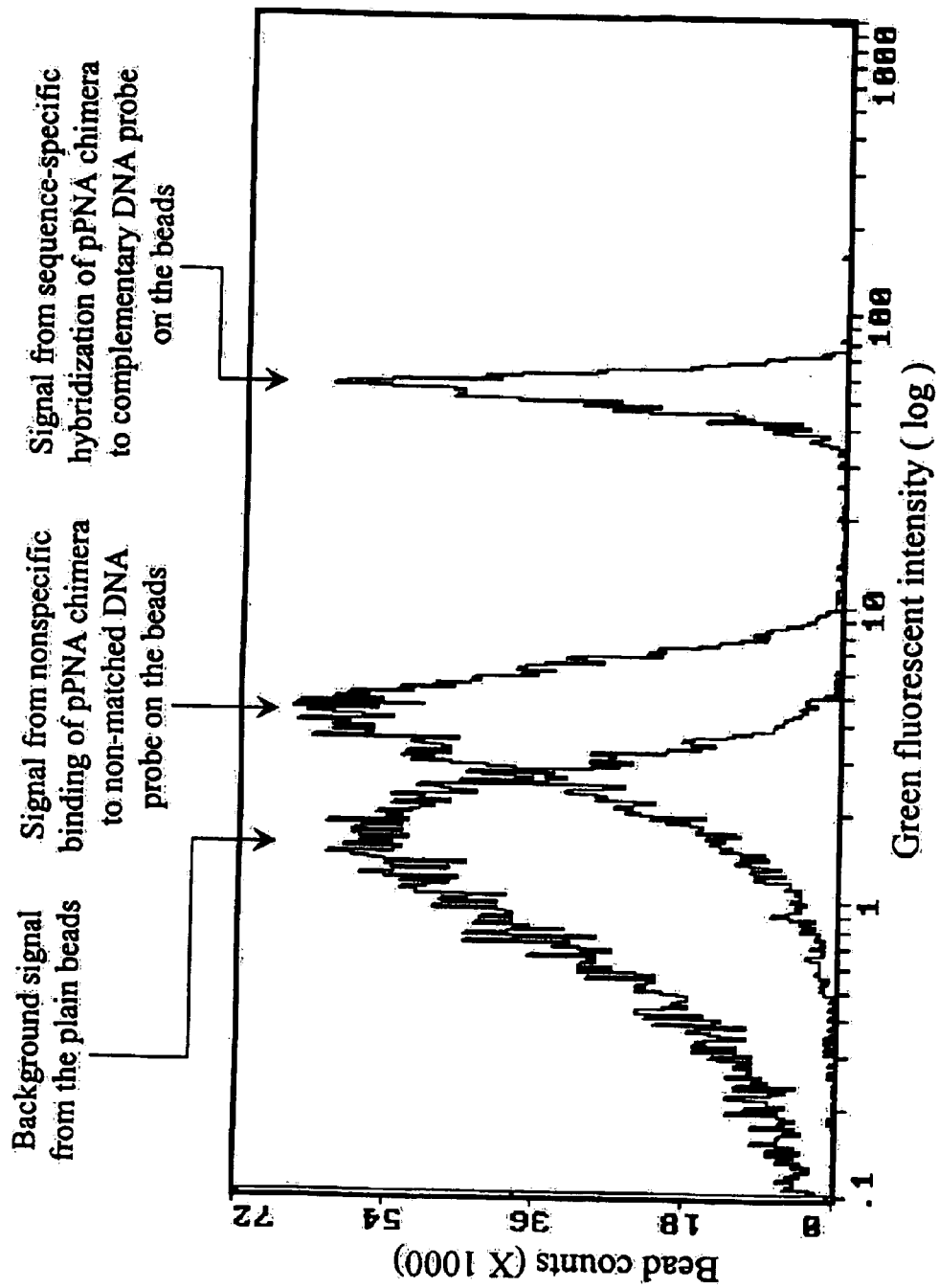
FIG. 25 shows the results of detecting PNA chimerae hybridized on color-encoded microparticles by flow cytometric analysis.

Detection of PNA Chimerae Hybridized to Oligonucleotides on Color-Encoded Microparticles by Flow Cytometric Analysis An example for detection of PNA chimerae hybridized to oligonucleotides on color-encoded microparticles by flow cytometric analysis is shown in FIG. 25A. Briefly, two types of green color-encoded beads (Green A and Green B) are coupled with two species of oligonucleotides with defined base sequence (Green A Biotin-Spacer-AAAAAAAAAA, SEQ ID NO: 6; Green B: Biotin-spacer-AAGGAGAGAA, SEQ ID NO: 7), respectively. Immobilization of the oligonucleotides to the beads was carried as described in Example 1, or according to prior known arts. The Green A and B beads have unique emission wavelength in the green channel, although emission wavelength in the orange wavelength is predominantly overlapping for the beads (FIG. 25A). The oligonucleotide-functionalized microparticles were used in the in-tube PNA hybridization as described in Example 5. The PNA anchoring domain of the biotinylated PNA-peptide chimerae bound to the complimentary oligonucleotide sensors immobilized on the Green B beads, but not to the unmatched oligonucleotides on the Green A beads. After hybridization, the particles were incubated with R-Phycoerythrin conjugated StreptAvidin (1:100) in 1×PBS. The R-Phycoerythrin conjugated StreptAvidin bound to biotinylated PNA-peptide chimerae hybridized on the beads. Detection of the hybridized PNA chimerae was performed by flow cytometric analysis. (Schematic as shown in FIG. 25C). As shown in FIG. 25A, after the assay, the Green B beads gained a significant amount of orange fluorescence corresponding to emission wavelength of the R-Phycoerythrin, indicating hybridization of the PNA peptide chimerae to the Green B beads in the assay (FIG. 25A). Detection by flow cytometry may be used on an in-tube pPNA hybridization to complementary oligonucleotides immobilized on microparticles. One of the two types of NeutrAvidin-coated microparticles was immobilized with biotin space. A(10), the other type of microparticles was not immobilized with any oligonucleotide. These two types of beads were incubated with biotinylated bis-pPNA chimerae. The anchoring portion of the bis-pPNA contained 12-13 thymine bases on each arm for hybridization. Hybridization and washing in in-tube conditions are as described above. Following hybridization, the beads were incubated with fluorescein (DTAF)-conjugted streptavidin (1:300) in 1×PBS. The fluorescein (DTAF)-conjugated streptavidin was bound to biotinylated pPNA chimera hybridized on the beads. Detection of the hybridized pPNA chimerae was performed by flow cytometric analysis.

Example 16

Figure 26:
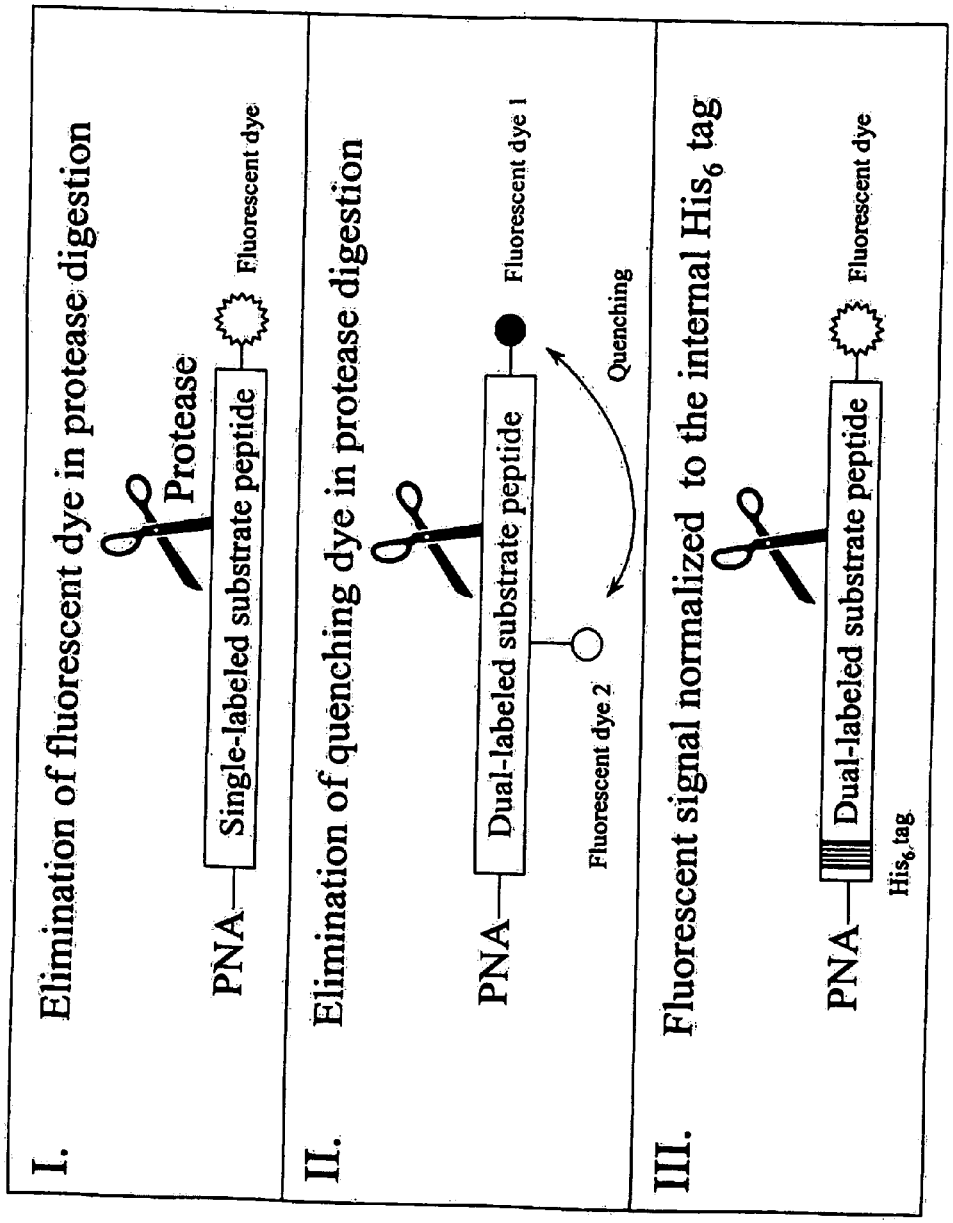
FIG. 26 shows the general design of PNA-peptide chimeric substrates for determining protease activity, where the functional domains of the chimerae are labeled with one fluorescent dye (I), two fluorescent dyes (II), and one fluorescent dye with an internal His6 tag (III).

General Design of Substrate Peptides for Determination of Protease Activity using Microparticle Arrays PNA-peptide chimeric substrates may be used for determining the presence of protease activity. Synthetic peptides have been routinely used in the determination of protease activity. These PNA-peptide chimeric substrates were designed in at least one of three formats (FIG. 26). Functional domains of the chimerae were labeled with one fluorescent dye (I), two fluorescent dyes (II), and one fluorescent dye plus an internal His6 tag (III). Protease digestion by an enzyme capable of cleaving a protein was detected by using the three differently labeled PNA-peptide chimeric substrates. Examples of such proteases include trypsin, chymotrypsin, thermolysin, papin, pronase, and HIV-1 protease. When the single-labeled PNA-peptide chimeric substrates (I) was used, protease digestion eliminated the presence of fluorescent dye from the digested substrates. When the dual-labeled PNA-peptide chimeric substrates (II) was used, protease digestion eliminated the quenching dye (Dye 1) from the substrates resulting in emission of fluorescence from Dye 2 of the cleaved products. When the PNA-peptide chimera with one fluorescent tag and an internal control tag (III) was used, protease digestion eliminated the fluorescent dye. Fluorescent signal from the uncut substrate was normalized to levels of detection signal generated from the internal His6 tag as shown in Example 16.

Example 17

Determination of Caspase Activity using Microparticle Arrays

Figure 27:
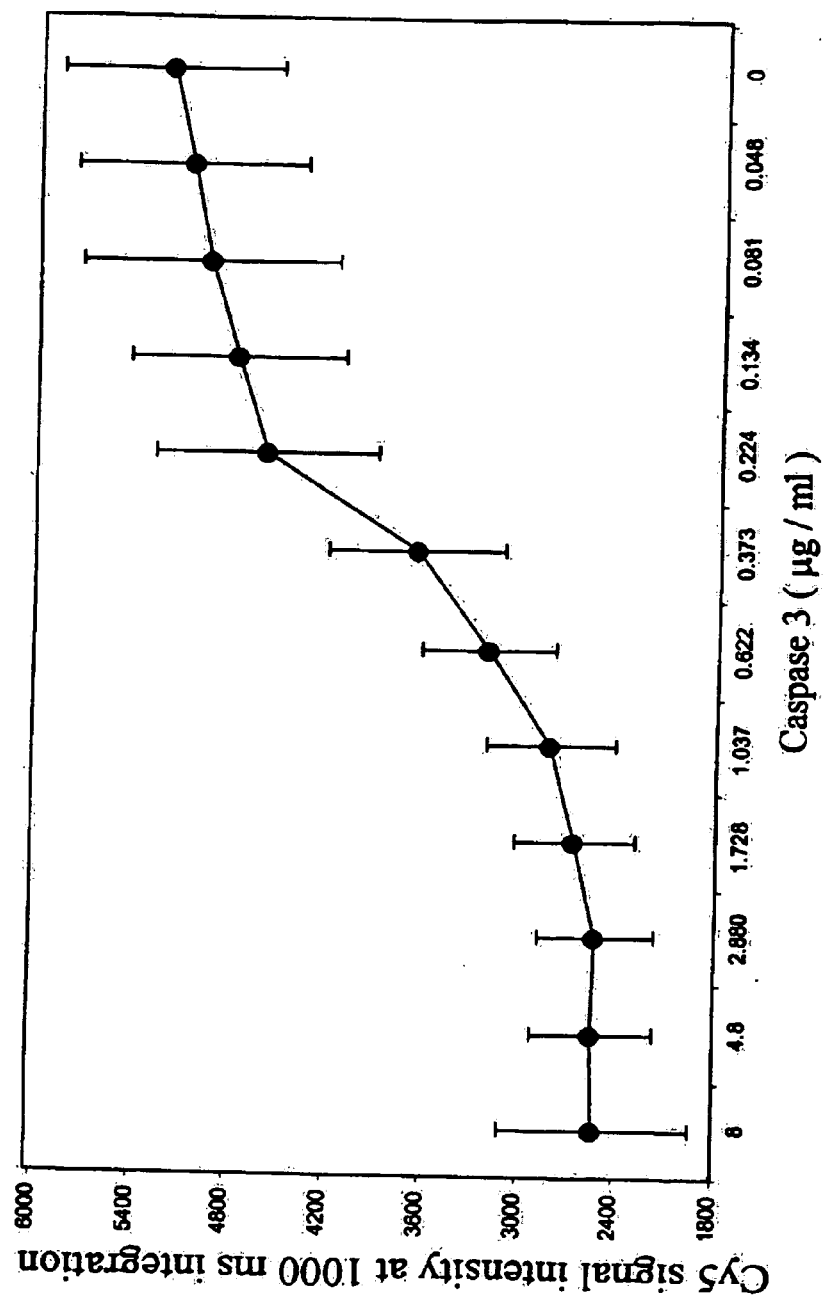
FIG. 27 shows the results of determining caspase activity using biotinylated Caspase 3 peptide substrate with end-labeled fluorescent dye on microparticle arrays.

Protease activity, such as Caspase activity, was determined by using end-labeled, biotinylated Caspase 3 peptide substrate immobilized to a solid surface. Equal amounts of biotinylated Caspase 3 peptide substrate with end-labeled fluorescent dye Cy5 was digested with decreasing amount of purified recombinant Caspase 3 (8, 4.8, 2.88, 1.728, 1.037, 0.62, 0.373, 0,224, 0.134, 0.081, 0.048 and 0 microgram/ml) in solution. After digestion, the digested products were coupled to the surface of defined color-encoded microparticles that had been coated with NeutrAvidin on the surface according to known prior art methods. The peptide-functionalized microparticles were then assembled into microparticle arrays according to the known prior art methods, such as LEAPS, and direct disposition assembly method previously described in Provisional Application Ser. No. 60/343,621, filed Dec. 28, 2001 and U.S. application Ser. No.10/192,352 filed Jul. 9, 2002. Fluorescence from the uncut peptide substrates was determined by using a fluorescent microscope according to known prior art methods, such as the Random Encoded Array Detection (READ) assay. Protease digestion eliminated fluorescent dye from the digested products. As shown in FIG. 27, a titration for Caspase 3 digestion was generated from the assay. The Cy5 signal intensity at 1000 ms integration increased from about 2600 to 5200 units for a decreasing Caspase 3 concentration ranging from 8 to 0 microgram/ml. The error bars shown in FIG. 27 represent standard deviation of the means.

Example 18

2×2 PNA Chimera Composition Assay on Microparticle Arrays

Figure 28:
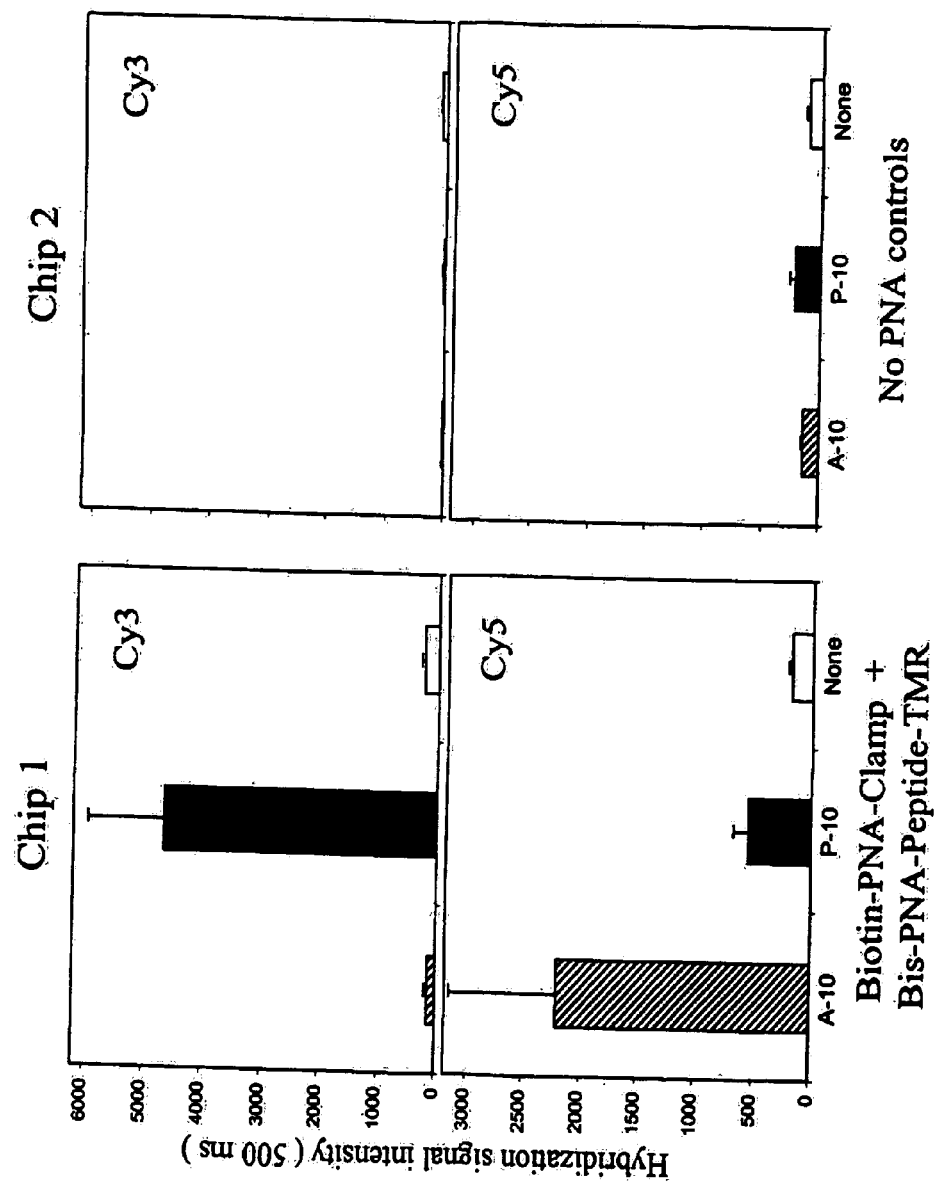
FIG. 28 shows the results of a 2×2 PNA chimera competition assay performed to test specificity of PNA chimerae captured to DNA oligonucleotides (10 bases in length) on microparticle arrays. Chip 1 shows the results of a biotinylated PNA clamp (Biotin-PNA-Clamp) (bottom panel) and a bis-PNA-peptide chimera conjugated with tetramethyl rhodamine (Bis-PNA-peptide-TMR) (top panel) captured to color-encoded beads functionalized with oligonucleotides with a defined base sequence. Chip 2 shows the negative control corresponding to the Biotin-PNA-Clamp (bottom panel) and Bis-PNA-peptide-TMR (top panel).

2×2 PNA chimera competition assays were performed to test specificity of PNA chimerae captured to DNA oligonucleotides on microparticle arrays in the presence of other PNA chimerae. Briefly, two types of bis-PNA with different base sequences were used in the assay. One of them was biotinylated PNA clamp (Biotin-PNA-Clamp), whereas the other is bis-PNA-peptide chimera conjugated with tetramethyl rhodamine (Bis-PNA-Peptide-TMR). Prior to hybridization, two types of biotinylated oligonucleotides were coupled to defined type of color-encoded microparticles that had been coated with NeutrAvidin on the surface according to known prior art methods, such as that described in Example 1. Sequences of these oligonucleotides were 10-mers of polyadenine (A-10) and 10-mers of defined nucleotide sequence (P-10), respectively. Control microparticles (none) contained no oligonucleotides on the surface. A-10 oligonucleotide was complementary to PNA of the Biotin-PNA-Clamp, whereas P-10 oligonucleotide was complementary to PNA of the Bis-PNA-Peptide-TMR chimera. After coupling, all of the oligonucleotide-functionalized microparticles were combined into one tube for assembling microparticle array on silicon chips. The chips were first pre-hybridized in a buffer containing 90 mM NaCl, 83 mM guanidine thiocyanate, 8 mM $MgCl_2$, 17 nM EDTA, 0.1% biotin, 0.1% Tween-20, 70 mM Tris-HCl, pH 7.5, at 40° C. for 20 min. Then, similar amounts of the Biotin-PNA-Clamp and the Bis-PNA-Peptide-TMR chimera were added into the same hybridization buffer for the chip. Negative control chip received no PNA in the hybridization buffer. Hybridization was carried out in a humid chamber at 40° C. for 1 hour. Upon completion of hybridization, the chips were washed with 100 mM NaCl, 10 mM Tris-HCl, pH 7.5, 0.196 Tween-20, at room temperature for 10 min. For detection of the biotinylated PNAs hybridized on the particles, the chips were incubated with Cy5-conjugated streptavidin (20 pg/ml) in 100 mM NaCl, 100 mM sodium phosphate, pH 7.5, at room temperature for 30 min. After washing with 15 mM NaCl, 10 mM Tris-HCl, pH 7.5, the chips were examined by using a fluorescence microscope. The identity of the particles was decoded according to their color codes. Particles with Cy5 signal or Cy3 signal for rhodamine were identified by using a computer program as described in Example 4. As shown in FIG. 28, the Biotin-PNA-Clamp was specifically captured to particles coupled with 10-mers polyadenine as detected by Cy5 fluorescence (about 2250 units Cy5 signal intensity at 500 ms integration), whereas the Bis-PNA-Peptide-TMR chimera was bound to particles with P-10 oligonucleotides as detected by Cy3 fluorescence (about 4500 Cy3 signal intensity at 500 ms integration) on the chip.

Example 19

Assembly of Peptide-Functionalized Microparticle Arrays by LEAPS

Figure 29:
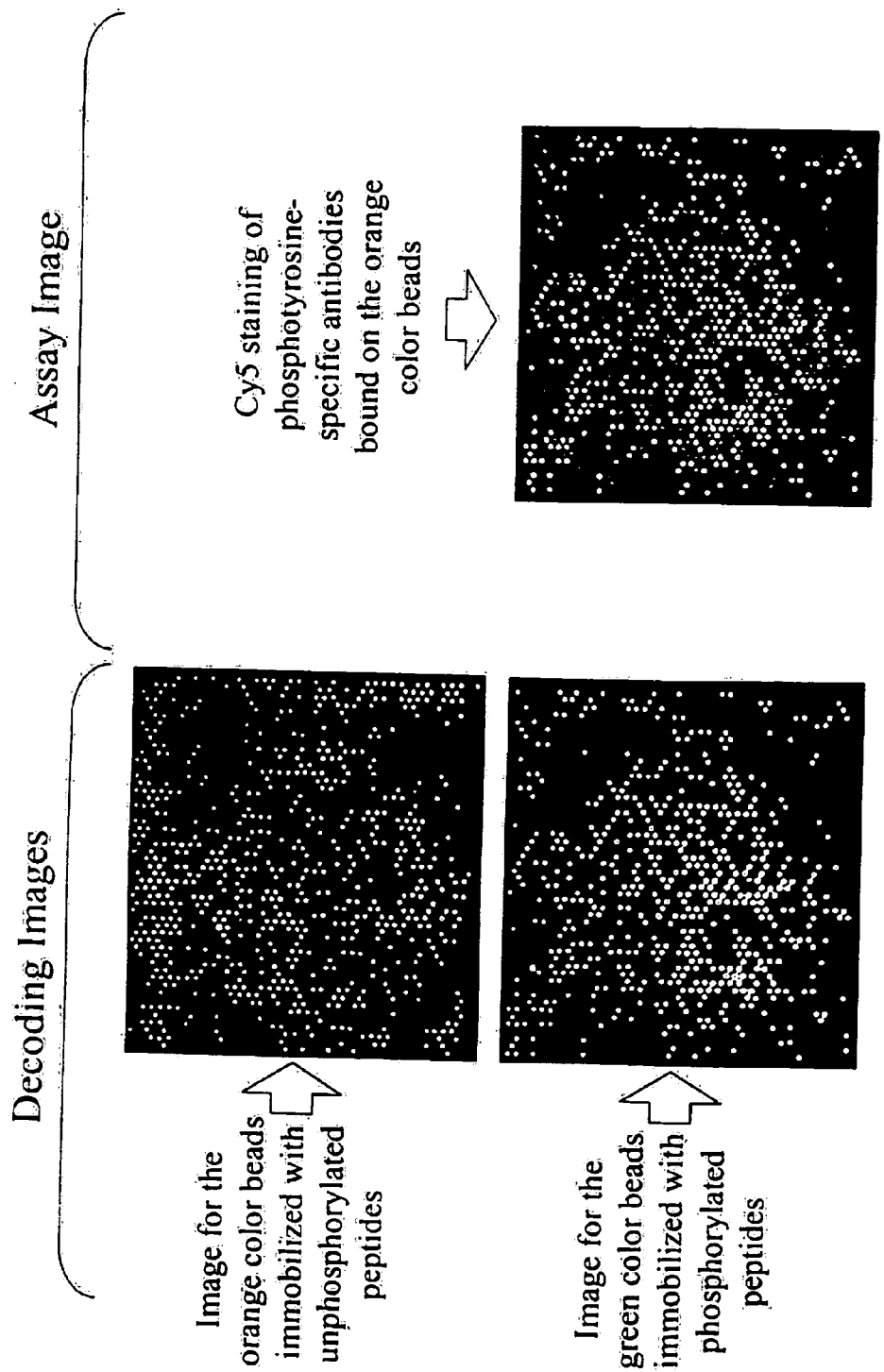
FIG. 29 shows the orange and green images used for decoding color-encoded microparticles, orange and green beads, coupled with a synthetic non-phosphorylated peptide and its corresponding phosphorylated peptide, respectively (left panel). The phosphorylated peptides on the Green beads were detected by using Cy-5-labeled antibodies on the chip (right panel).

Two types of color-encoded microparticles, Orange and Green beads, were coupled with a synthetic peptide and its corresponding phosphorylated peptide, respectively. Amino acid sequences of the peptides are identical, except there is a phosphate group on a tyrosine residue of the phosphorylated peptide. These two types of peptide-functionalized microparticles were mixed in one test tube. The microparticles were assembled into microparticle arrays on silicon chips by LEAPS as disclosed in U.S. Pat. No. 6,251,691. The microparticle arrays were then incubated with mouse monoclonal antibodies specific for the phosphotyrosine of the peptide. Binding of the monoclonal antibodies was detected by using Cy5-labeled goat anti-mouse IgG on the chips as described in Example 12. The chips were then examined using a fluorescent microscope. The orange and green images were used for decoding the microparticles, whereas the Cy5 staining labels the green beads immobilized with the phosphorylated peptides. More specifically, the image for the orange colored beads represent non-phosphorylated peptides, while the image for the green colored beads represent phosphorylated peptides. The resulting assay image shows Cy5 fluorescent staining of phosphotyrosine-specific antibodies as shown in FIG. 29.

Example 20

Figure 30A:
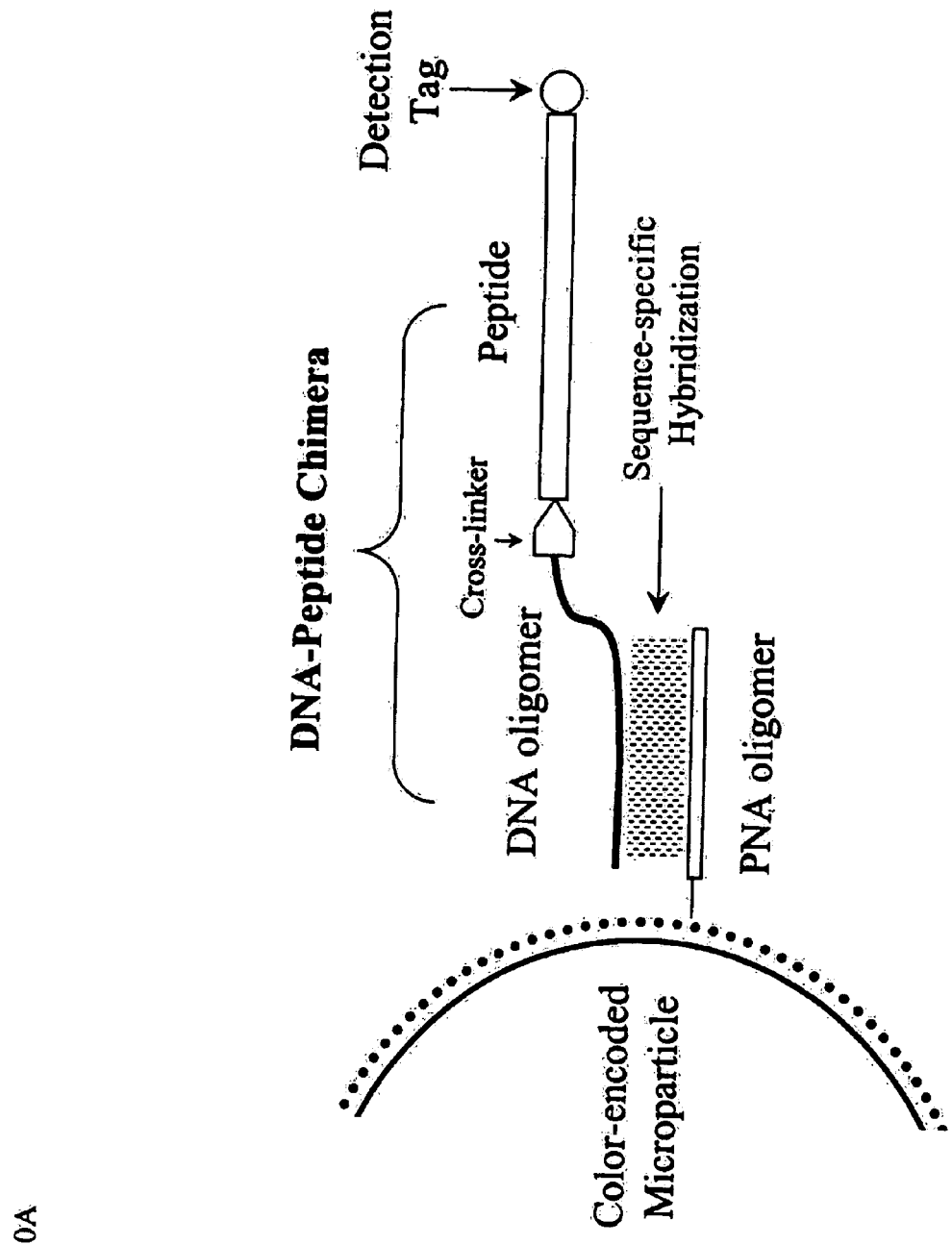
FIG. 30 shows an illustration of a DNA-peptide chimera (A) and the hybridization results of a DNA-peptide chimera to complementary PNA coupled on color-encoded beads on microparticle arrays (B).
Figure 30B:
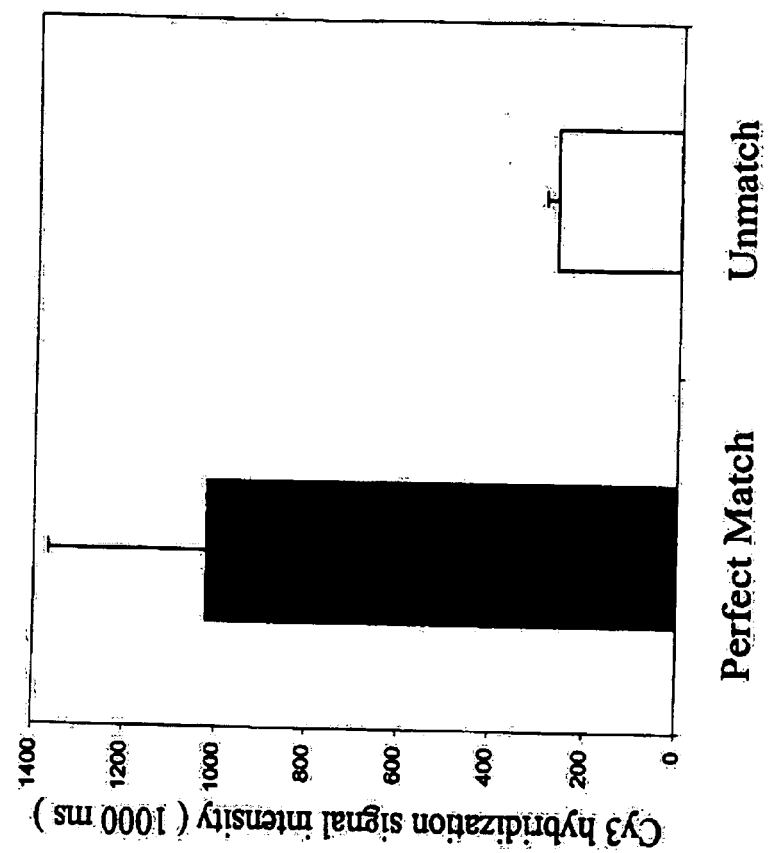

Hybridization of DNA-Peptide Chimerae to PNA Coupled to Color-Encoded Beads on Microparticle Arrays Similar to the PNA-peptide chimera previously described, DNA oligonucleotides may be conjugated to synthetic peptides by using bifunctional cross-linkers. The resulting conjugate is known as a DNA-peptide chimera. The DNA-peptide chimera may be used in hybridization of complimentary PNA oligomer immobilized on color-encoded beads on microparticle array. The peptide moiety may contain at least one tag, such as biotin or fluorescent dyes, for detection of the hybridized DNA-peptide chimera on the beads. In addition, ligands with high affinity to the peptide or modification of the peptide may also be used for the detection. The principal of hybridizing a DNA-peptide chimera to a PNA-functionalized microparticle is illustrated in FIG. 30A. In the present example, a DNA-peptide chimera is a conjugate of a deoxy-adenine oligomer (dA oligomer) and a biotinylated synthetic peptide with a bifunctional cross-linker, SMCC, succinimidyl 4-(N-maleimidomethyl, cyclohexane-1-carboxylate). The DNA-peptide conjugate was purified using liquid chromatography. The purified DNA-peptide chimera was used to hybridize PNA thymine oligomers immobilized on color-encoded beads on microparticle arrays. The hybridized DNA-peptide chimera was detected by using Cy3-conjugated StreptAvidin. The microparticle array was examined by using a fluorescence microscope. Fluorescence intensity for the bead color and the Cy3 hybridization signal was determined from the array. The identity of the microparticles was decoded according to their color codes. Beads with Cy3 fluorescent dye were detected and identified. As shown in FIG. 30B, the DNA-peptide chimerae specifically bind to PNAs with perfect match base sequence as indicated by a Cy3 signal intensity at 1000 ms integration of about 1000 units and a unmatched perfect base sequence resulted in about a 300 units Cy3 signal intensity at 1000 ms integration.

Example 21

Caspase Digestion of Multiple Substrates

Reactivity of caspase against multiple peptide substrates could be simultaneously determined by using PNA-peptide chimerae. In this example, three types of PNA-peptide chimerae, I, II and III, were synthesized. Each of the chimerae contains a unique PNA anchoring moiety with defined base sequence, which is conjugated with specific caspase substrate peptide as functional moiety. The functional moieties of PNA chimera I, II and III contains amino acids Asp-Glu-Val-Asp (SEQ ID NO: 8), Val-Glu-Ile-Asp (SEQ ID NO: 9), and Ile-Glu-Thr-Asp (SEQ ID NO: 10), respectively. These synthetic peptides are Caspase 3, 6, and 8 substrates known from the prior arts. The C-terminus of the peptides was labeled with defined fluorescent dye. Caspase digestion of the chimeric substrates results in elimination of the fluorescent dye from the PNA anchoring moieties.

The multi-substrate caspase digestion was set up as follows: Certain amounts of chimera I, II and III were mixed together in one test tube. Aliquots of the chimera mix were added into reaction solutions containing Caspase 3, 6, and 8, respectively. Caspase digestion of the chimeric substrates was carried out by incubation of the reaction mixtures in a water bath for certain period of time. Negative control is reaction mix without any caspases. After digestion, hybridization mixtures were by adding equal amount of hybridization buffer, containing guanidine HCl and detergents, into the reaction mixtures. The hybridization mixtures were then incubated with pre-assembled microparticle arrays.

The microparticle arrays contain four types of color-encoded beads assembled on silicon chips according to methods commonly known in the art. Three types of the beads were functionalized with oligonucleotides with defined based sequences, which could bind to PNA-peptide chimera I, II and III, respectively, in sequence-specific manners. In addition to the encoding colors, the fourth-type of the beads also contains color matching to the fluorescent dye labeled on the chimeras, which was used for normalization of color intensity from different arrays.

After hybridization, nonspecific bindings were washed away from the arrays followed by examination using a fluorescent microscope. The assay signal, color intensity from the hybridized PNA chimeras, was determined from the beads on the arrays. Identity of the beads was decoded according to their predefined color codes. Intensity ratios, ratio of the assay signal and signal from the control beads, were determined. The negative control reaction should give maximum levels of intensity ratios in the assay. Caspase activity for particular substrates was expressed as percentage of the residual assay intensity ratios relative to the negative controls on each chip. The relative percentages for the assay intensity ratios from this study are summarized in following table:

| Enzymes | PNA-Peptide Chimera | | |
|---|---|---|---|
| | I | II | III |
| Caspase 3 | 53.48% | 82.35% | 112.03% |
| Caspase 6 | 91.80% | 41.18% | 79.08% |
| Caspase 8 | 73.77% | 69.41% | 59.89% |

The bold numbers represent more intense digestion than expected in the assay.

Example 22

Flow Chart for Enzyme Assays Using PNA

Figure 31:
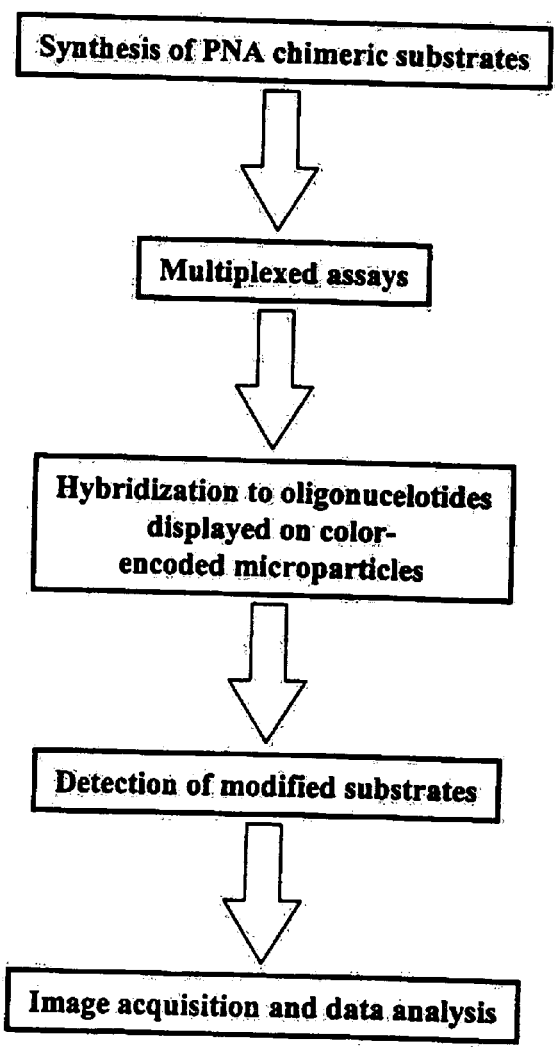
FIG. 31 illustrates the steps in a multiplexed assay using PNA chimeric substrates.

Multiplexed assays using PNA chimeric substrates disclosed herein have several advantages over the prior known arts. In the PNA chimeric construct, the PNA anchoring portion plays two important roles in multiplexed assays. First of all, the base sequence of PNA serves as a code for the conjugated substrates. Secondarily, the PNA oligomers serve as specific anchors for the chimeras that may be captured to complementary oligonucleotides displayed on encoded solid surface. There is no known protease and nuclease for PNA degradation. Thus, the PNA oligomers will be very stable in tissue lysate. Compared to DNA-DNA hybridization, PNA hybridizes to complementary DNA oligonucleotides under very mild conditions. The PNA-DNA complexes are stable in low salt solution, i.e., conditions not favored for DNA-DNA hybridizations. Thus, multiple PNA chimeric substrates may be added into a common reaction mixture for single or multiple types of enzymatic reactions. As illustrated in FIG. 31, multiplexed assays disclosed herein may be carried out in a simple format, which includes steps of synthesis of PNA chimeric substrates, performing of multiplexed assays, hybridization to oligonucleotides displayed on color-encoded microparticles, detection of modified substrates, image acquisition and data analysis.

Example 23

Multiplexed Assays

Figure 32A:
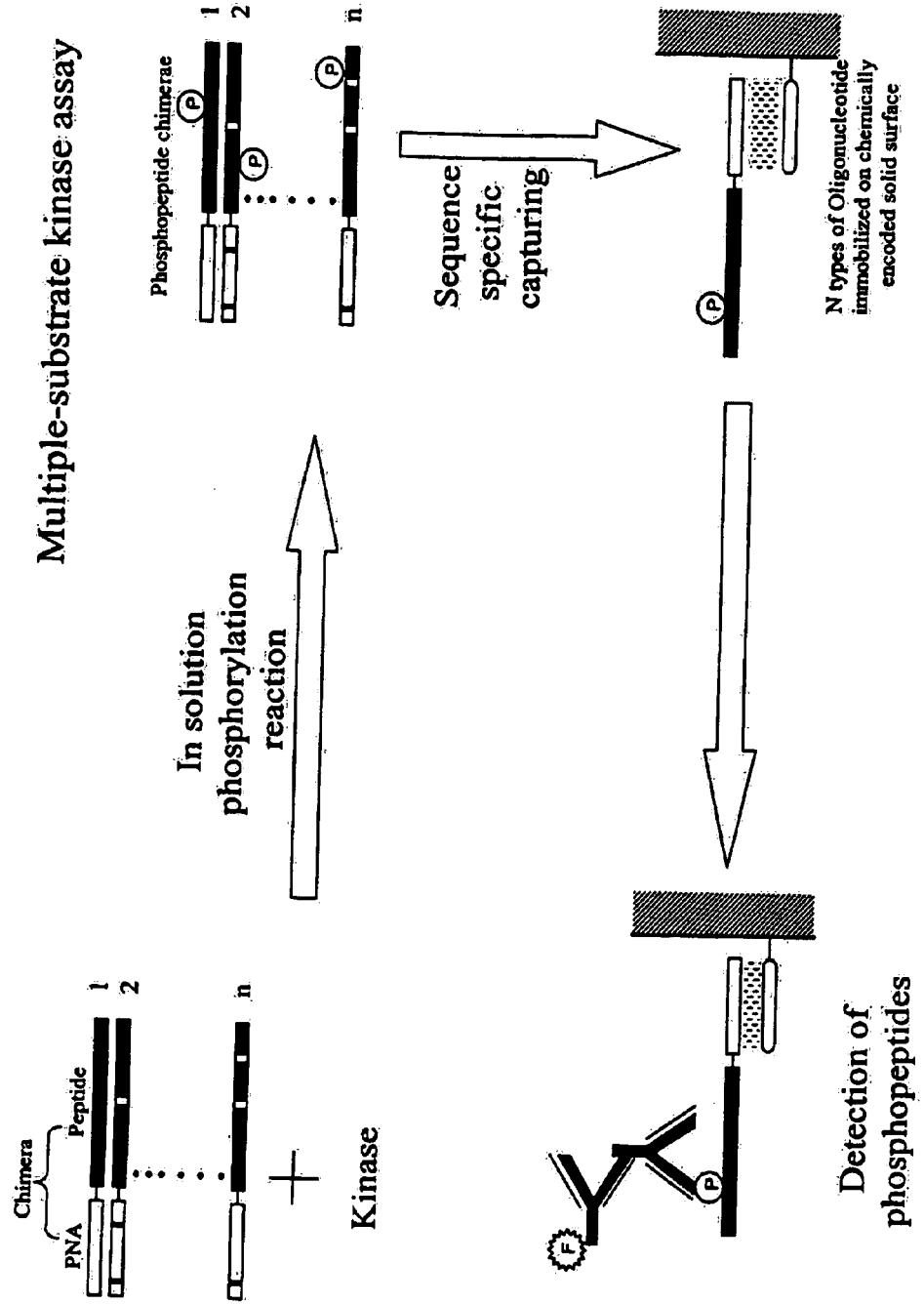
FIG. 32A illustrates a multiple substrate assay for kinase using the constructs disclosed herein.
Figure 32B:
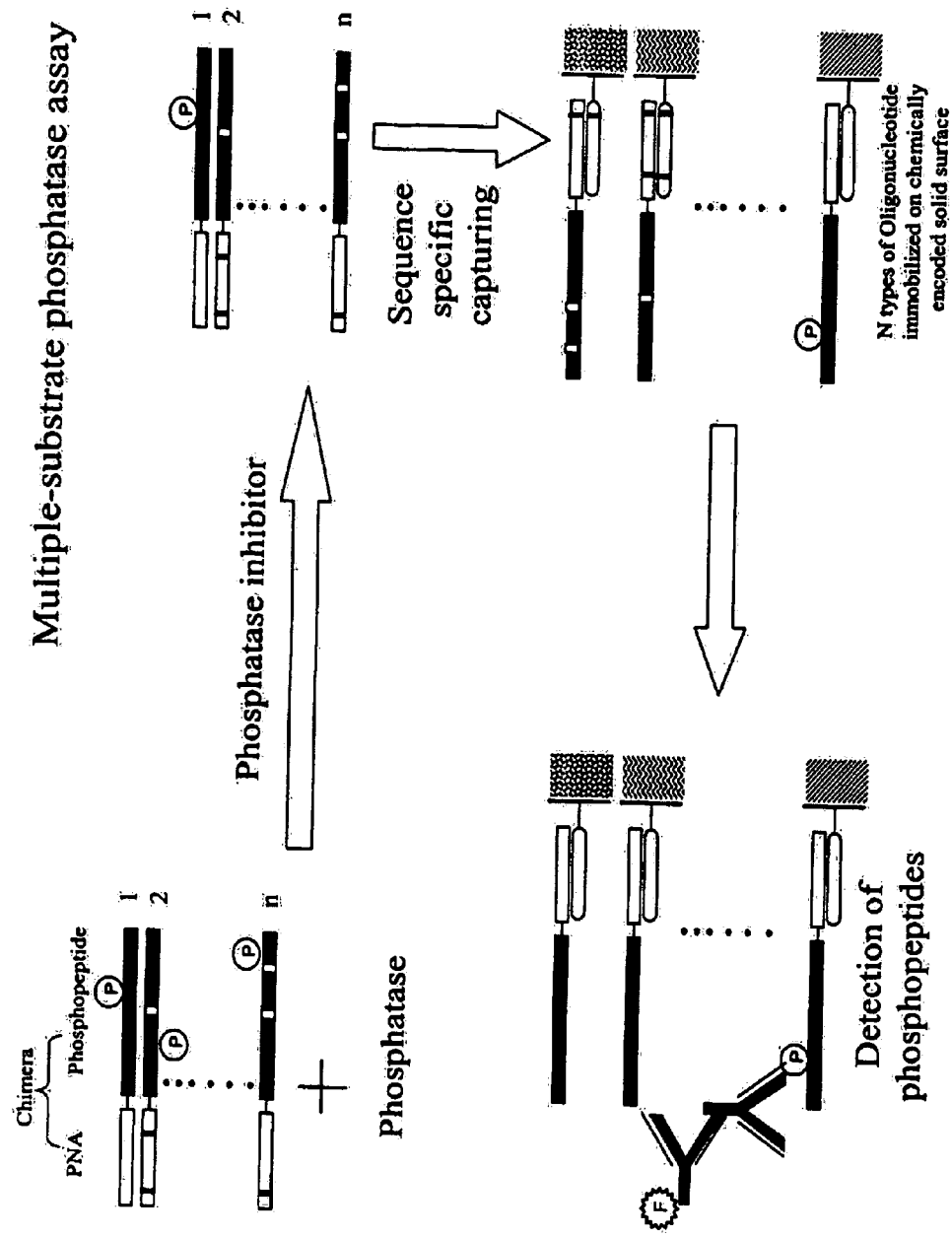
FIG. 32B illustrates a multiple substrate assay for phosphate using the constructs disclosed herein.
Figure 32C:
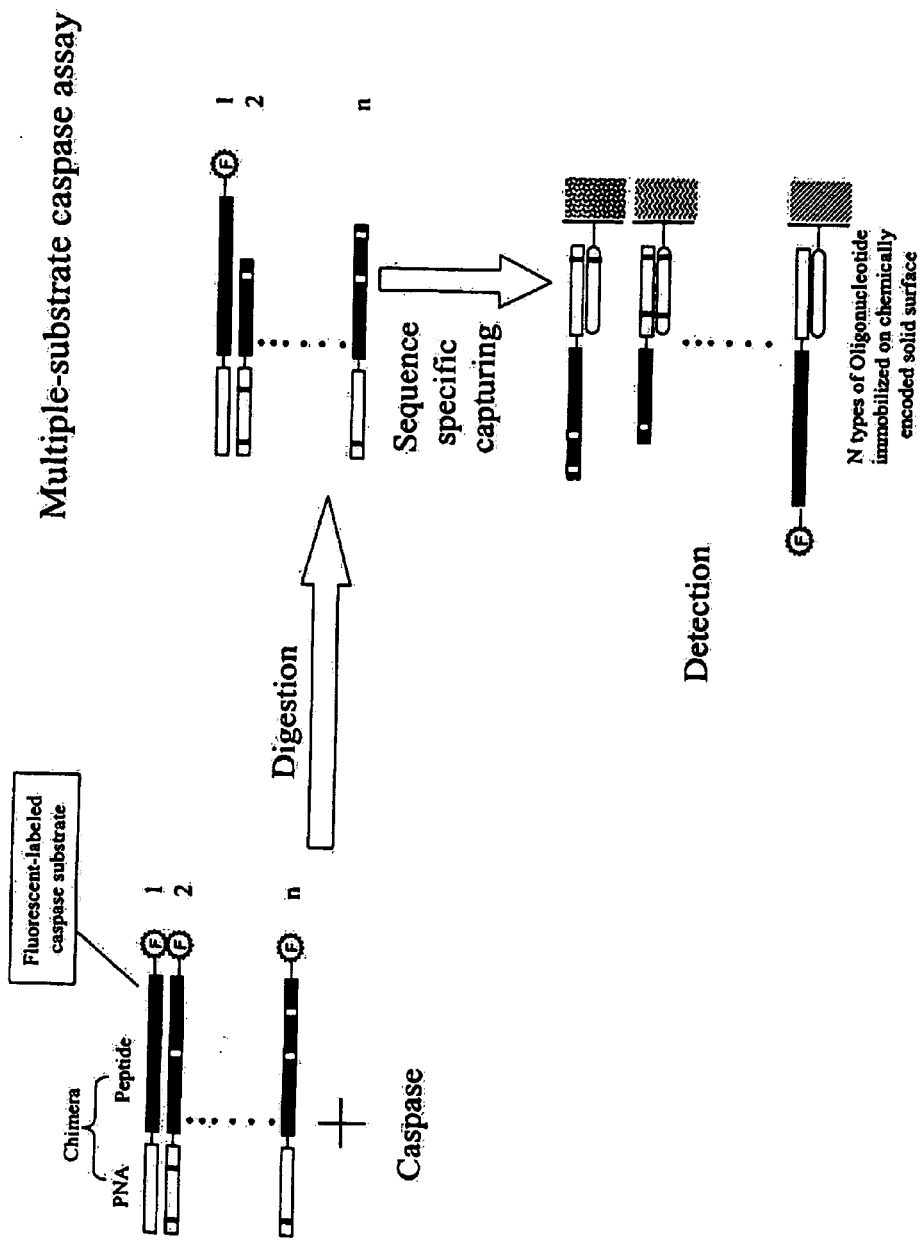
FIG. 32C illustrates a multiple substrate assay for caspase using the constructs disclosed herein.
Figure 32D:
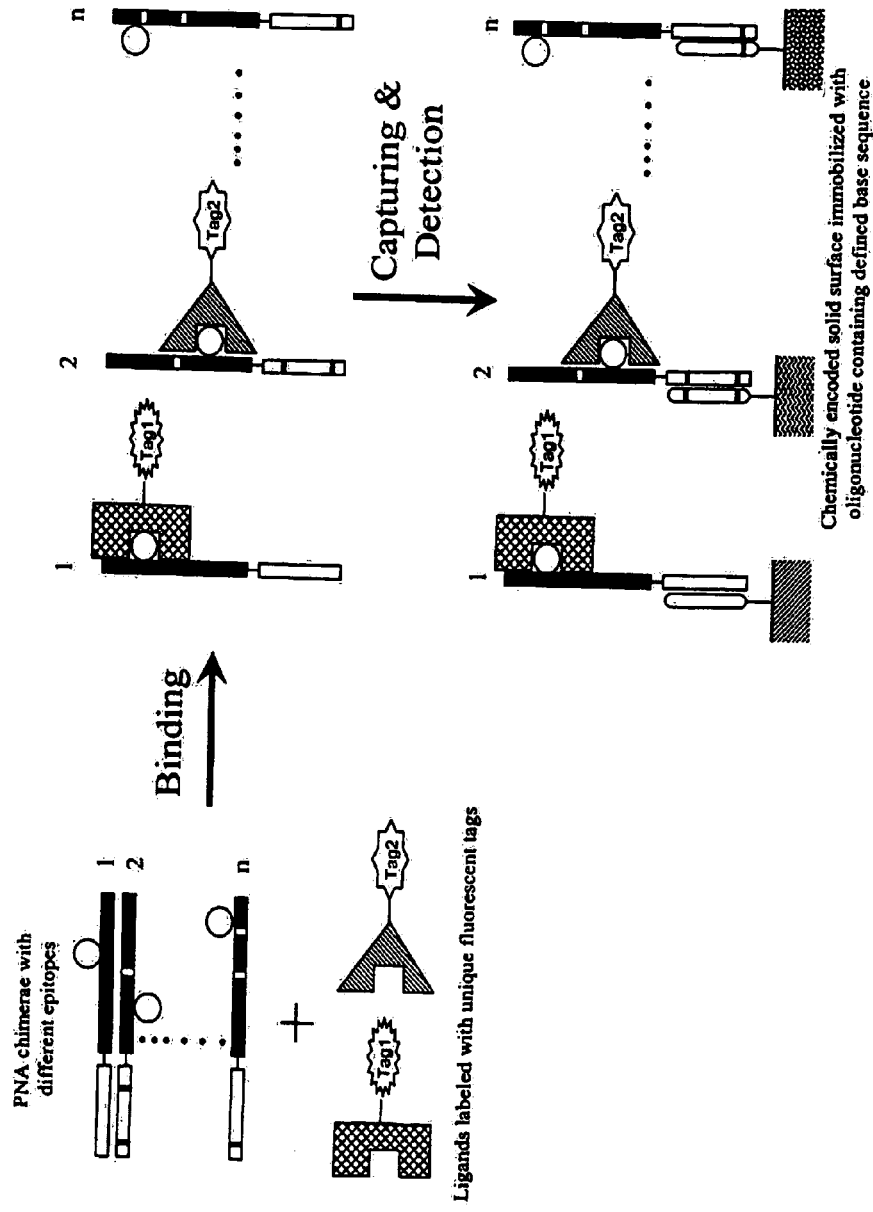
FIG. 32D illustrates a multiple substrate assay binding assay using the constructs disclosed herein.

As one of the preferred embodiments, PNA-peptide chimeras are the ideal substrates for multiple-substrate enzymatic reactions, such as kinase assays (FIG. 32A), phosphatase assays (FIG. 32B), caspase assays (FIG. 32C), and ligand binding assays (FIG. 32D). Briefly, a library of PNA-peptide chimeras may be incubated with a kinase of interest. After an in-solution phosphorylation reaction, phosphorylated peptides may be determined on the captured PNA chimeras (FIG. 32A). Thus, substrate peptides for the kinase may be identified from the library. Design of this assay may be applied to drug discovery for target identification for altered kinase activity in disease stages. By using PNA-phosphorylated peptide chimeras as substrates, a similar design may be applied to multiple-substrate phosphatase assays (FIG. 32B), which may be used in drug discovery to identify specific phosphatase inhibitors for various disease stages. In addition, as shown in Example 17, PNA-peptide chimeras can be used to determine caspase activity in in vitro assays. As illustrated in FIG. 32C, a library of PNA-peptide chimeras may be incubated with a caspase of interest. Substrate peptides may be identified from the library after the digestion. Design of this assay may be used in identification of caspase inhibitors in apoptotic cells. Furthermore, PNA-peptide chimeras may also be used in binding assays in the analysis of protein-protein interactions or protein-nucleic acid interactions. As shown in Panel C (FIG. 32D), a library of PNA-peptide chimeras may be incubated with targets of interest in ligand binding assays. PNA-peptide chimeras bound with specific targets may be identified from the library (FIG. 32D).

The above description of various preferred embodiments has been presented for purposes of illustration and description. It is not intended to be exhaustive or limiting to the precise forms disclosed. Obvious modifications or variations are possible in light of the above teachings. The embodiments discussed were chosen and described to provide illustrations and its practical application to thereby enable one of ordinary skill in the art to utilize the various embodiments and with various modifications as are suited to the particular use contemplated. All such modifications and variations are within the system as determined by the appended claims when interpreted in accordance with the breadth to which they are fairly, legally and equitably entitled.

What is claimed is:

1. A method of detecting a plurality of enzyme activities in a sample, comprising:
   (a) adding a plurality of types of PNA-substrate chimerae to the sample, said PNA-substrate chimerae having a PNA capture portion and a substrate for an enzyme, wherein different types have different substrates capable of reacting with different enzymes but each type has a particular substrate and a selected PNA sequence capture portion;
   (b) allowing the enzymes to react with the substrate portions of the chimera population;
   (c) capturing the reacted PNA-substrate chimerae with different types of oligonucleotides, wherein said different types of oligonucleotides are displayed on differently encoded microparticles, and wherein said capturing is by annealing of a type of oligonucleotide to a selected PNA sequence capture portion; and
   (d) detecting the changes in the substrates of captured reacted PNA-substrate chimerae;
   (e) decoding the encoded microparticles to identify which substrates reacted and thereby identify the presence of particular enzymes in the sample.

2. The method of claim 1, wherein the microparticles are color-encoded.

3. The method of claim 1, wherein the PNA-substrate chimera contains two tags.

4. The method of claim 3, wherein the tags are a fluorescent moiety.

5. The method of claim 1, wherein the substrate portion of the PNA-substrate chimera is a substrate of a caspase.

6. The method of claim 1, wherein the substrate portion of the PNA-substrate chimera is a substrate of a phosphatase.

7. The method of claim 1, wherein the capture portion of the PNA-substrate chimera is a bis-PNA.

* * * * *